(12) United States Patent
Krueger

(10) Patent No.: US 11,490,809 B2
(45) Date of Patent: *Nov. 8, 2022

(54) OCULAR PARAMETER-BASED HEAD IMPACT MEASUREMENT USING A FACE SHIELD

(71) Applicant: Wesley W. O. Krueger, San Antonio, TX (US)

(72) Inventor: Wesley W. O. Krueger, San Antonio, TX (US)

(73) Assignee: Wesley W. O. Krueger, San Antonio, TX (US)

(*) Notice: Subject to any disclaimer, the term of this patent is extended or adjusted under 35 U.S.C. 154(b) by 268 days.

This patent is subject to a terminal disclaimer.

(21) Appl. No.: 16/903,136

(22) Filed: Jun. 16, 2020

(65) Prior Publication Data
US 2020/0305708 A1 Oct. 1, 2020

Related U.S. Application Data

(63) Continuation-in-part of application No. 16/264,242, filed on Jan. 31, 2019, now Pat. No. 10,716,469, (Continued)

(51) Int. Cl.
*A61B 3/113* (2006.01)
*G06F 3/01* (2006.01)

(52) U.S. Cl.
CPC .............. *A61B 3/113* (2013.01); *G06F 3/012* (2013.01); *G06F 3/013* (2013.01); *A61B 2562/02* (2013.01)

(58) Field of Classification Search
CPC ..... A61B 3/113; A61B 2562/02; G06F 3/012; G06F 3/013
(Continued)

(56) References Cited

U.S. PATENT DOCUMENTS 3,616,463 A 11/1971 Theodore et al.
4,817,633 A 4/1989 MoStravick et al.
(Continued)

FOREIGN PATENT DOCUMENTS

WO 2013117727 8/2013

OTHER PUBLICATIONS

Article originally published by Popular Science on the internet at www.popsci.com/science/2012-12/helmet-wars-and-new-helmet-could-protect-us-all (attached).
(Continued)

*Primary Examiner* — Mohammed A Hasan
(74) *Attorney, Agent, or Firm* — Kilpatrick Townsend & Stockton LLP

(57) ABSTRACT

A system and/or method for measuring a human ocular parameter comprises a human-wearable face shield which has an eye sensor, a head orientation sensor, and an electronic circuit, and a face shield. The eye sensor comprises a video camera that measures horizontal eye movement, vertical eye movement, pupillometry, and/or eyelid movement. The head orientation sensor measures pitch and/or yaw of the wearer's face. The electronic circuit is response to the eye sensor and the head orientation sensor and measures an ocular parameter such as vestibulo-ocular reflex, ocular saccades, pupillometry, pursuit tracking during visual pursuit, vergence, eye closure, focused position of the eyes, dynamic visual acuity, kinetic visual acuity, virtual retinal stability, retinal image stability, foveal fixation stability, or nystagmus.

20 Claims, 26 Drawing Sheets

Related U.S. Application Data which is a continuation-in-part of application No. 15/713,418, filed on Sep. 22, 2017, now Pat. No. 10,231,614, which is a continuation-in-part of application No. 15/162,300, filed on May 23, 2016, now Pat. No. 9,788,714, which is a continuation-in-part of application No. 14/326,335, filed on Jul. 8, 2014, now Pat. No. 9,370,302, which is a continuation-in-part of application No. 13/749,873, filed on Jan. 25, 2013, now abandoned.

(58) Field of Classification Search
USPC .......................................................... 351/209
See application file for complete search history.

(56) References Cited

U.S. PATENT DOCUMENTS

| | | | |
|---|---|---|---|
| 5,180,907 A | 1/1993 | Udden et al. | |
| 5,204,998 A | 4/1993 | Liu | |
| 5,550,601 A | 8/1996 | Donaldson | |
| 5,555,895 A | 9/1996 | Ulmer et al. | |
| 5,621,922 A | 4/1997 | Russ | |
| 5,838,420 A | 11/1998 | MacGregor Donaldson | |
| 5,919,149 A | 7/1999 | Allum | |
| 5,942,954 A | 8/1999 | Galiana et al. | |
| 5,953,102 A | 9/1999 | Berry | |
| 5,978,972 A | 11/1999 | Steward et al. | |
| 6,301,718 B1 | 10/2001 | Rigal | |
| 6,796,947 B2 | 9/2004 | Watt et al. | |
| 6,826,509 B2 | 11/2004 | Crisco et al. | |
| 6,931,671 B2 | 8/2005 | Skiba | |
| 7,276,458 B2 | 10/2007 | Wen | |
| 7,380,938 B2 | 6/2008 | Chmielewski et al. | |
| 7,386,401 B2 | 6/2008 | Vock et al. | |
| 7,401,920 B1 | 7/2008 | Kranz et al. | |
| 7,448,751 B2 | 11/2008 | Kiderman et al. | |
| 7,500,752 B2 | 3/2009 | Nashner | |
| 7,509,835 B2 | 3/2009 | Beck | |
| 7,526,389 B2 | 4/2009 | Greenwald et al. | |
| 7,651,224 B2 | 1/2010 | Wood et al. | |
| 7,682,024 B2 | 3/2010 | Plant et al. | |
| 7,727,162 B2 | 6/2010 | Peterka | |
| 7,731,360 B2 | 6/2010 | MacDougall et al. | |
| 7,753,523 B2 | 7/2010 | Kiderman et al. | |
| 7,849,524 B1 | 12/2010 | Williamson et al. | |
| 7,866,818 B2 | 1/2011 | Schroeder et al. | |
| 7,931,370 B2 | 4/2011 | Bartomeu | |
| 7,988,287 B1 | 8/2011 | Butler et al. | |
| 8,232,881 B2 | 7/2012 | Hertz | |
| 8,253,814 B2 | 8/2012 | Zhang et al. | |
| 8,285,416 B2 | 10/2012 | Cho et al. | |
| 8,510,166 B2 | 8/2013 | Neven | |
| 8,529,463 B2 | 9/2013 | Della Santina et al. | |
| 8,578,520 B2 | 11/2013 | Halldin | |
| 8,696,126 B2 | 4/2014 | Yoo et al. | |
| 8,764,193 B2 | 7/2014 | Kiderman et al. | |
| 10,191,294 B2 | 1/2019 | Macnamara | |
| 10,535,151 B2 | 1/2020 | Bleyer et al. | |
| 10,716,469 B2 * | 7/2020 | Krueger | A61B 3/112 |
| 2002/0118339 A1 | 8/2002 | Lowe | |
| 2006/0059606 A1 | 3/2006 | Ferrara | |
| 2006/0098087 A1 | 5/2006 | Brandt et al. | |
| 2006/0270945 A1 | 11/2006 | Ghajar | |
| 2008/0022441 A1 | 1/2008 | Oranchak et al. | |
| 2009/0021695 A1 | 1/2009 | Scarpino | |
| 2010/0036289 A1 | 2/2010 | White et al. | |
| 2010/0092049 A1 | 4/2010 | Schroeder et al. | |
| 2010/0101005 A1 | 4/2010 | Cripton et al. | |
| 2010/0198104 A1 | 8/2010 | Schubert et al. | |
| 2010/0280372 A1 | 11/2010 | Poolman et al. | |
| 2011/0176106 A1 | 7/2011 | Lewkowski | |
| 2011/0209272 A1 | 9/2011 | Drake | |
| 2012/0133892 A1 | 5/2012 | Furman et al. | |
| 2012/0143526 A1 | 6/2012 | Benzel et al. | |
| 2012/0198604 A1 | 8/2012 | Weber et al. | |
| 2012/0204327 A1 | 8/2012 | Faden et al. | |
| 2012/0297526 A1 | 11/2012 | Leon | |
| 2013/0232668 A1 | 9/2013 | Suddaby | |
| 2013/0278899 A1 | 10/2013 | Waldorf et al. | |
| 2014/0111771 A1 | 4/2014 | Liu | |
| 2014/0192326 A1 | 7/2014 | Kiderman et al. | |
| 2014/0327880 A1 | 11/2014 | Kiderman et al. | |
| 2015/0038803 A1 | 2/2015 | Uhlig et al. | |
| 2015/0223683 A1 | 8/2015 | Davidovics et al. | |
| 2015/0243099 A1 | 8/2015 | Schowengerdt | |
| 2015/0245766 A1 | 9/2015 | Rennaker et al. | |
| 2015/0335239 A1 | 11/2015 | Macfougall | |
| 2016/0033750 A1 | 2/2016 | Nunnink et al. | |
| 2016/0062459 A1 | 3/2016 | Publicover et al. | |
| 2016/0081546 A1 | 3/2016 | MacDougall | |
| 2016/0085302 A1 | 3/2016 | Publicover et al. | |
| 2016/0106315 A1 | 4/2016 | Kempinski | |
| 2016/0110920 A1 | 4/2016 | Schowengerdt | |
| 2016/0132726 A1 | 5/2016 | Kempinski et al. | |

OTHER PUBLICATIONS

Allison et al. Combined Head and Eye Tracking System for Dynamic Testing of the Vestibular System. IEEE Transactions on Biomedical Engineering. vol. 43 No. 11, Nov. 1996 (USA).

* cited by examiner

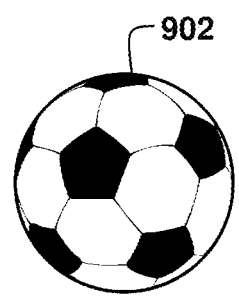
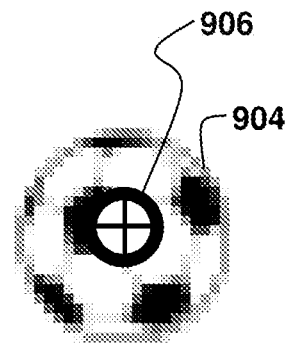
FIG. 19A  FIG. 19B
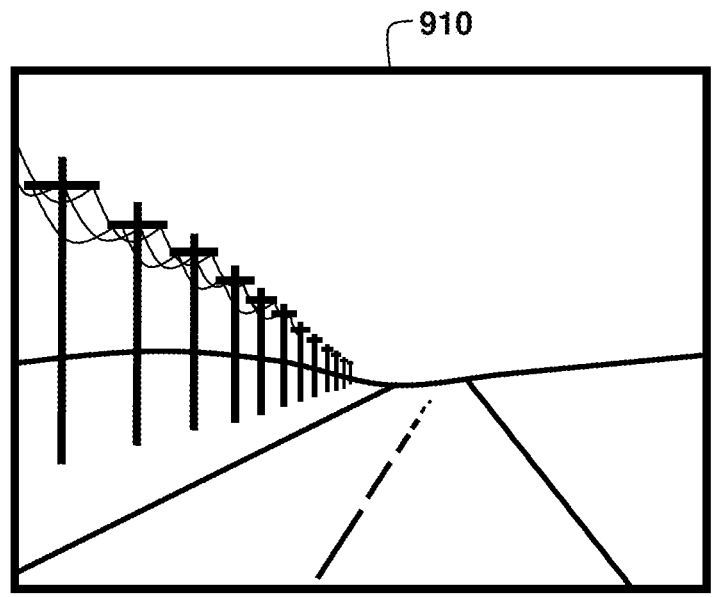
FIG. 20

OCULAR PARAMETER-BASED HEAD IMPACT MEASUREMENT USING A FACE SHIELD

CROSS REFERENCE TO RELATED APPLICATIONS

This application is a continuation-in-part of U.S. patent application Ser. No. 16/264,242 filed 31 Jan. 2019, which is a continuation-in-part of U.S. patent application Ser. No. 15/713,418 filed 22 Sep. 2017, now U.S. Pat. No. 10,231,614, which is a continuation-in-part of U.S. patent application Ser. No. 15/162,300 filed 23 May 2016, now U.S. Pat. No. 9,788,714, which is a continuation-in-part of U.S. patent application Ser. No. 14/326,335 filed 8 Jul. 2015, now U.S. Pat. No. 9,370,302. U.S. patent application Ser. No. 16/264,242 is also a continuation-in-part of U.S. patent application Ser. No. 13/749,873 filed 25 Jan. 2013. The entire disclosures of all of the aforementioned patents and applications are incorporated by reference herein.

FIELD OF INVENTION

Embodiments of the invention(s) disclosed herein relate to systems and methods that use human ocular parameter measurement in a face shield to detect and manage concussions, traumatic brain injury and/or cognitive deficits.

BACKGROUND

Concussions are a type of traumatic brain injury (TBI) that is sometimes called a mild traumatic brain injury or a moderate traumatic brain injury and abbreviated as an MTBI. Concussions and the resultant chronic traumatic encephalopathy (CTE) have reached epidemic proportions in the U.S. The CDC estimates that as many as 3.8 million sports-related concussions occur in the U.S. each year including professional athletes, amateurs of all levels, and children. There are over 250,000 emergency room visits of young people annually for head injuries from sports and recreation activities. Over 50 million Americans participate in team sports and all of them are at some level of risk of experiencing a concussion. Concussions from multiple head blows and the resulting CTE have caused several professional football players to commit suicides. The U.S. National Football League (NFL) and the scientific community recognize that concussions are a major concern for both players and the sport itself. Concussions also occur in college and high school football, in other sports such as ice hockey and cycling, and in military operations. The incidence of concussions and traumatic brain injury has reached epidemic proportions in the military. Blast-related injuries predominate and approximately 60 percent of the injured soldiers have symptoms of traumatic brain injury (TBI).

Concussions happen in the brain's white matter when forces transmitted from a-forceful impact strain nerve cells and their connections, the axons, resulting in changes to the brain such as pruning, synaptic pruning, and myelination. Linear blunt trauma can happen when falling to the ground and hitting the back of the head. The falling motion propels the brain in a straight line downward. Rotational blunt trauma can occur when a player is spun, rolled or turned with the head hitting the object. The base of the skull is rough with many internal protuberances. These ridges can cause trauma to the temporal lobes during rapid deceleration. There is a predicted intracranial pressure wave after a concussive blow with the positive pressure (coup) to negative pressure (contre-coup) occurring across the brain. A high sheer stress occurs in the central core of the brain (e.g., brainstem). Axonal injury occurs with degeneration/disintegration in discrete regions of the brain. Axon retraction and areas of hemorrhage are noted.

Diffuse axonal injury (DAI) occurs from impact forces. The injury to tissue is greatest in areas where the density difference is greatest. For this reason, almost ⅔ of DAI lesions occur at the gray-white matter junction. Location of injury depends on plane of rotation. The magnitude of injury depends on the distance from the center of rotation, arc of rotation, duration and intensity of the force. The occurrence of visual, cognitive and vestibular deficits following a TBI is high. Neuro-ophthalmic symptoms and signs, such as abnormal eye movements, are often the presenting or predominant complaints. There are numerous types of abnormal eye movements resulting from TBI which can be measured with eye tracking. Observed findings with concussions/TBI often include abnormalities with eye fixation, vergence, pupillometry, saccades and difficulty with visual pursuit. Additionally, TBIs cause an insult to the vestibular system, which results in abnormal eye movements and eye reflexes. As a result of difficulty with visual fixation and visual processing, a decline in visual attentiveness, visual memory and cognition occurs. Even uncorrected visual deficits can accelerate cognitive decline. Mild traumatic brain injury (mTBI) frequently leads to disruptions in eye tracking resulting in cognitive deficits, such as difficulty with executive function, even at the lowest levels of injury severity. Importantly, visual/eye movement, vestibular and subsequent cognitive disorders are likely responsible, in part, for subsequent mental health issues. The mechanical insult initiates a complex cascade of metabolic events. Starting from neurotoxicity, energetic metabolism disturbance caused by the initial mitochondrial dysfunction seems to be the main biochemical explanation for most post-concussive signs and symptoms. Furthermore, concussed cells enter a peculiar state of vulnerability, and if a second concussion is sustained while they are in this state, they may be irreversibly damaged by the occurrence of swelling. This condition of concussion-induced brain vulnerability is the basic pathophysiology of the second impact syndrome.

Prior Art Eye Movement Based Concussion Assessment

The ability to track objects in the environment is an important feature for humans to interact with their surroundings. In particular, the ability to recognize the presence of an environmental hazard is directly linked to our ability to fix our gaze on a visualized target of interest, recognize the threat, and implement a plan of action. Therefore, the central nervous system (CNS) is imposed with a series of tasks and time constraints that require a harmonic integration of several neural centers located in multiple regions and linked through an efficient transmission of information. There are central nervous system (CNS) impairments in individuals with mTBIs long after the last traumatic episode. Even a mild TBI (mTBI), also known as a concussion, will result in oculomotor abnormalities and can cause visual problems, including, but not limited to dysfunction with visual fixation on a visual element or visual object of interest and vergence. In addition to glare and photophobia, individuals commonly report problems including blurred vision; squinting; double vision/diplopia; difficulty reading; watching television; using computers; loss of visual acuity; color discrimination; brightness detection; contrast sensitivity; visual field defects; visuospatial attention deficits; slower response to visual cues; visual midline shift syndrome, affecting balance and posture; impaired accommodation and convergence;

nystagmus; visual pursuit disorders; deficits in the saccadic system; extraocular motility problems resulting in strabismus, reduction in stereopsis; reading problems, including losing one's place, skipping lines, and slow reading speed.

The measurement of ocular parameters can greatly enhance the ability to determine whether a traumatic brain injury has occurred. However, technology for accurately measuring ocular parameters portably is not optimized for concussion evaluation.

The EYE-SYNC System, a sideline test, quantifies the predictive timing of dynamic visuo-motor synchronization (DVS) between gaze and target during predictive circular visual tracking. Eye-Sync utilizes a head worn goggles which measures smooth pursuit, while the head remains motionless, which is not as accurate as other measures. It is also not a stand-alone device, but requires an accessory computer attached, and lacks-the ability to measure the vestibular component as well as other ocular parameters. The test takes 1 minute, while the user visualizes a dot moving in a circle.

The Eye-Guide Focus system features an eye-tracking headset and a portable chin mount. Its software runs on an iPad facing the user and the user has to follow a small white circle moving across the screen with their eyes in order to set the baseline of how their eyes normally function. This system lacks complete portability and uses similar technology to Eye-Sync.

Neuro Kinetics I-PAS System is a battery of tests using goggles and measures oculomotor and reaction times to test whether certain neural pathways have been altered or are behaving abnormally. I-Pass test subjects wear a pair of goggles linked to a laptop and allows the tester to measure very small changes in the user's eye muscles while the test is taking place. This testing is performed in a clinical environment, lacks portability and is comprised of multiple pieces of equipment, with medical personnel required to interpret the data obtained.

Oculogica's EyeBOX uses ocular motility to detect cranial nerve function and provides a BOX Score indicative of the presence and severity of brain injury. The EyeBOX requires no pre-test calibration which can omit critical information if the subject being evaluated has indeed suffered a TBI or concussion. This test requires the user to rest their chin and forehead comfortably on the device and watch a video for less than four minutes. This requires laboratory testing and also lacks portability.

The evidence shows that more sophisticated testing is needed which portable, more accurate for concussion detection, and can be used on the field of play, in a military operative environment or in any other environment where a concussion is likely to occur. Specifically, oculomotor parameter measurement as described with this invention using ocular and head sensing elements and transducers have shown high sensitivity and accuracy in identifying athletes who experienced a sport-related concussion. When comparing all these tests, the VOR has the highest percentage for identifying the individual with concussions.

Concussion Mitigation

There are different types of forces, linear and rotational acceleration which act on the brain in any physical trauma. Linear accelerations are straight-line forces that begins at the point of impact. It occurs most acutely during angular impacts. With violent blows to the head there is often a combination of linear and rotational forces. Most of the blows to the head will occur off-center and therefore most of the accelerations in the head are going to be rotational. These rotational forces strain nerve cells and axons more than linear forces resulting in greater neuronal injury.

Current methods for mitigating traumatic brain injuries are limited in their effectiveness. Although helmets typically provide some protection against linear impacts, their protection against rotational impacts is deficient. This is clearly problematic given the severity of head injuries caused by rotational impacts. There is no pharmacologic treatment for any of these injuries. For these and other reasons, new technology and concepts must be implemented to improve helmet construction for impact protection, detecting and managing concussions and protecting the brain.

Studies of head impacts in football show that concussions occur when a person receives one or more hits that induce linear head accelerations of greater than about 80 g or rotational head accelerations of greater than about 5000 rad/sec$^2$. An analysis of the speed at impact shows that a world-class sprinter can run about 10 m/sec (23 miles/hour). A 4-minute mile is equivalent to 6.7 m/sec, which is about ⅔ of the speed of a world-class sprinter. Football helmet test standards use 12 mile/hour impacts, which equals approximately 5 m/sec or half of the speed of a world-class sprinter. The padding on a typical football helmet is less than 1 inch thick. From physics:

$x = (0.5) \, a \, t^2$ $v = a \, t$ (if acceleration is constant)

where: x is displacement, v=velocity, a=acceleration, and t=time

If one solves the above equations for constant deceleration from 5 m/sec to 0 m/sec in 1 inch (1/40$^{th}$ of a meter or 25 millimeters), the result is 500 m/sec$^2$ or approximately 50 g (the acceleration of gravity is approximately 10 m/sec$^2$). This means that padding that perfectly decelerates from 5 m/sec to 0 in 25 mm (1 inch) could theoretically provide a constant deceleration rate of 50 g. However, the padding on a helmet is far from this optimum in that (a) it doesn't provide a full inch of travel in actual use and (b) it doesn't provide the constant resistive force needed for perfect linear deceleration. Furthermore, athletes may sprint at speeds that create an impact having an initial velocity of greater than 12 miles per hour. A calculation of rotational accelerations based on typical current football helmet configurations shows that a one inch of rotation of the outer shell of a 12-inch helmet to stop an initial radial velocity of 12 miles/hour (5 m/sec) at a radius of 6 inches generates an angular acceleration of about 5000 rad/sec$^2$ which is the concussion threshold as the threshold for linear acceleration (or deceleration) of the head. These theoretical calculations are consistent with the medical data that shows that concussions occur frequently in high school, collegiate, and professional football. Helmet manufacturers and the test labs understand the inability for current helmet designs to prevent concussions and place the following warning message on all football helmets sold in the USA: "No helmet can prevent all head and neck injuries a player might receive while participating in football".

Concluding Summary

It is desired to provide a head impact measurement and mitigation system and/or method that is fundamentally superior to the prior art. Specifically, there is a need for self-contained systems and methods that more objectively detect concussions, more effectively mitigate concussions, and measure physiologic parameters affecting human performance.

BRIEF DESCRIPTION OF THE DRAWINGS

The present invention will be better understood on reading the following detailed description of non-limiting embodiments thereof, and on examining the accompanying drawings, in which:

FIG. 19A shows an unaltered visual element;

FIG. 19B shows the visual element of FIG. 11A that has been altered by defocusing the visual element and superimposing a target;

FIG. 20 shows a scene that can be used for optokinetic testing;

Figure 1A:
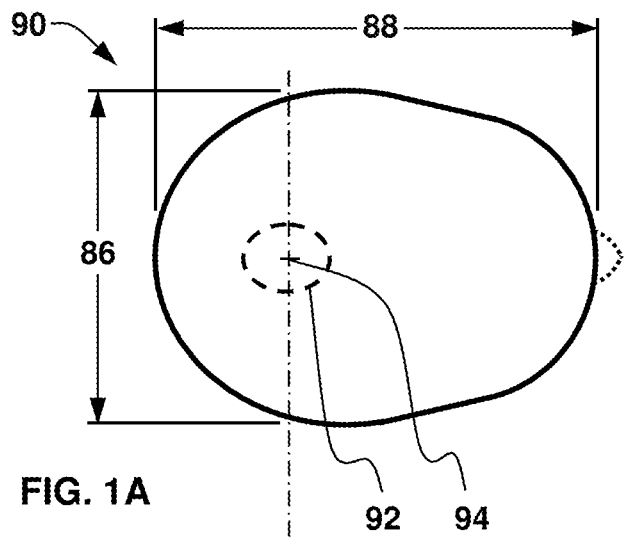
FIG. 1A shows a top view of a typical human skull.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It should be understood that various changes could be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details.

In a preferred embodiment, the present invention comprises head tracking and ocular-based sensors integrated into a face shield. The face shield could be attached to a helmet that is attached to a subject's head or the face shield could be directly attached to a subject's head with no helmet needed for the system. The ocular-based sensors comprise at least one camera that views at least one eye of the subject. The face shield can also comprise an augmented reality display, which projects visual information to the user for assessment of ocular parameters. The information from this eye camera can be combined with sensors that measure head rotation to determine whether human performance has been degraded by a blow to the head. The vestibular ocular reflex, after an impact, is an example of one ocular parameter-measurement that could be made using this system to determine if the wearer has suffered a concussion or similar injury. Other ocular parameter measurements include, but are not limited to: pupillometry, ocular saccades, visual pursuit tracking, nystagmus, vergence, convergence, divergence, eye-lid closure, dynamic visual acuity, kinetic visual acuity, retinal image stability, foveal fixation stability, and focused position of the eyes or visual fixation at any given moment. The system can include other sensors to monitor the physiologic, chemical, and/or biochemical heath of the user in real time during activity.

Definitions

The definitions that follow apply to the terminology used in describing the content and embodiments in this disclosure and the related claims.

Alert Filters are algorithmic tools that take in sensor data, compare that data against a set of rules and thresholds, and output a result that is typically in the form of a binary outcome. The rules and thresholds represent the sensitivity and reporting levels desired for the use case. A representative sample of this type of filter is a Random Forest Ensemble. The result can be robust in the data it contains but should lead to a true/false response to each rule or threshold.

An artificial intelligence system is a computer system that attempts to implement aspects of human-level intelligence, in which a machine can learn and form judgements to improve a recognition rate for information as it is used. Artificial intelligence technologies include a machine learning (deep learning) technology that uses an algorithm that classifies/learns the characteristics of input data by itself and an elemental technology that simulates functions such as recognition, judgment, like the human brain by utilizing a machine learning algorithm. The elemental technology may include any one of the following: a linguistic comprehension technique for recognizing human languages/characters, a visual comprehension technique for recognizing objects as in human vision, a reasoning/predicting technique for judging and logically reasoning and predicting information, a knowledge expression technique for processing human experience information as knowledge data, and an operation control technique for controlling autonomous driving of the vehicle or the motion of a robot.

Angular velocity is defined as speed of a physical object that is moving along a circular path. The angular velocity of an object is the object's angular displacement with respect to time. Angular velocity is the rate of change of the position angle of an object with respect to time, so w=theta/t, where w=angular velocity, theta=position angle, and t=time. Angular velocity, also called rotational velocity, is a quantitative expression of the amount of rotation that a spinning object undergoes per unit time. It is a vector quantity, consisting of an angular speed component and either of two defined directions or senses.

Augmented reality (AR) is a technology that superimposes a computer-generated image on a user's view of the real world, thus providing a composite view. Mixed reality (MR) is a type of augmented reality in which real and virtual worlds are combined to produce new environments and visualizations where physical and digital objects co-exist and interact. In this document, the use of AR and MR are used synonymously as both represent visual systems used in this invention.

Biometrics can be defined as physiological measurements and consist of various sensors that measure the activity in bodily systems in response to things that are experienced through our senses or imagined. This can be direct measurement of the central nervous system (e.g., the brain) or organs that are connected to the peripheral nervous system (e.g., the pupils of the eyes, sweat glands in our skin). The goal of biometrics generally is to measure bodily responses that are more direct indicators of emotional states. There are many possible biometrics, including DNA, odor, gait, height, handwriting, and speech, but vision-based biometrics use image sensors and algorithms derived from machine vision. Applications for biometrics include controlling access to a building (physical access), authenticating a user to allow access to some resource (for example, accessing a secured Web site), and identifying a person from among others.

Blinks are the involuntary act of shutting and opening the eyelids. They are known to reflect changes in attention and thus they are likely to reflect an individual's cognitive effort. In particular, fewer blinks have been associated with increased attention. For example, a study shows that surgeons had a lower number of blinks when performing surgery as compared to when they were engaged in casual conversations. In addition to the number of blinks, the duration of blinks can also indicate cognitive effort. For example, shorter blink durations were associated with increased visual workload during a traffic simulation task. Similarly, comparing blink data during a hard (math problem solving) and easy task (listening to relaxing music), people exhibited shorter blink durations during the hard task. When the eyes are closed during a blink, there is no incoming visual information to process.

A classifier (or machine learning classifier) is an algorithmic computer vision tool that takes an input data frame (a picture for example), processes the pixel-level information against a target, and outputs a result. A classifier attempts to identify a pattern within the pixels and compares that pattern to its target set. Classifiers can be of a machine learning type (representatives of this group include convolutional neural networks or general adversarial networks) or of a static type (representatives of this group include Haar cascades and Local Binary Patterns), but typically require some form of training for optimization.

Cognition refers to pertaining to the mental processes of perception, memory, judgment and reasoning as contrasted with emotional and volitional processes. Cognitive processes can be defined as encompassing all information processing even at the subconscious level or as strictly the ability to think and reason. Some specific processes involved in cognition may be memory, association, language, and attention. Other related cognitive processes are concept formation, pattern recognition, imagery, and problem solving.

A concussion is defined as an immediate and transient loss of consciousness accompanied by a brief period of amnesia after a blow to the head.

Convolutional Neural Network: An AI/Machine Learning algorithm which can take in an input image, assign importance (learnable weights and biases) to various aspects/objects in the image and be able to differentiate one from the other. The architecture of a CNN is analogous to that of the connectivity pattern of neurons in the human brain and was inspired by the organization of the visual cortex. Individual neurons respond to stimuli only in a restricted region of the visual field known as the receptive field. A collection of such fields overlaps to cover the entire visual area.

Corneal reflex is defined as causing both eyes to blink in response to tactile stimulation of the cornea.

Dynamic visual acuity (DVA) can be used interchangeably with kinetic visual acuity (KVA) as they both have the same meaning. In this document, DVA will be used to assess impairments in a person's ability to perceive objects accurately while actively moving the head, or the ability to track a moving object. It is an eye stabilization measurement while the head is in motion. In normal individuals, losses in visual acuity are minimized during head movements by the vestibulo-ocular system that maintains the direction of gaze on an external target by driving the eyes in the opposite direction of the head movement. When the vestibulo-ocular system is impaired, visual acuity degrades during head movements. The DVA is an impairment test that quantifies the impact of the vestibulo-ocular system pathology on a user's ability to maintain visual acuity while moving. Information provided by the DVA is complementary to and not a substitute for physiological tests of the VOR system. The DVA quantifies the combined influences of the underlying vestibulo-ocular pathology and the person's adaptive response to pathology. DVA testing is sometimes obtained for those persons suspected of having an inner ear abnormality. Abnormalities usually correlate with oscillopsia (a visual disturbance in which objects in the visual field appear to oscillate or jump while walking or moving). Currently with DVA testing, worsening of visual acuity by at least three lines on a visual acuity chart (e.g., Snellen chart or Rosenbaum card) during head turning from side to side at 1 Hz or more is reported as being abnormal. In normal individuals, losses in visual acuity are minimized during head movements by the vestibulo-ocular system that maintains the direction of gaze on an external target by driving the eyes in the opposite direction of the head movement When the vestibular system is impaired, visual acuity degrades during head movements. Individuals with such ocular performance deficits can improve their dynamic acuity by performing rapid "catch-up" saccadic eye movements and/or with predictive saccades.

Dynamic visual stability (DVS) and retinal image stability (RIS) can be used interchangeably. In this document, DVS will be used to describe the ability to visualize objects accurately, with foveal fixation, while actively moving the head. When the eye moves over the visual scene, the image of the world moves about on the retina, yet the world or image observed is perceive as being stable. DVS enables a person to prevent perceptual blurring when the body moves actively. The goal of oculomotor compensation is not retinal image stabilization, but rather controlled retinal image motion adjusted to be optimal for visual processing over the full range of natural motions of the body or with head movement. Although we perceive a stable visual world, the visual input to the retina is never stationary. Eye movements continually displace the retinal projection of the scene, even when we attempt to maintain steady fixation. Our visual system actively perceives the world by pointing the fovea, the area of the retina where resolution is best, towards a single part of the scene at a time. Using fixations and saccadic eye movements to sample the environment is an old strategy, in evolutionary terms, but this strategy requires an elaborate system of visual processing to create the rich perceptual experience. One of the most basic feats of the visual system is to correctly discern whether movement on the retina is owing to real motion in the world or rather to self-movement (displacement of our eyes, head or body in space). The retinal image is never particularly stable. This instability is owing to the frequent occurrence of tremors, drifts, microsaccades, blinks and small movements of the head. The perceptual cancellation of ocular drift appears to primarily occur through retinal mechanisms, rather than extra-retinal mechanisms. Attention also plays a role in visual stability, most probably by limiting the number of items that are fully processed and remembered.

Eye Correcting Algorithm (ECA) is an algorithmic computer vision tool. It builds upon a Classifier by attempting to account for movement between the camera itself and the eye being observed. This movement is typically referred to as slippage and the ECA takes the input data frame (the same picture as the classifier), processes the information to determine appropriate offsets, and supplies the offset parameters as its output.

Eye tracking refers to the process of measuring where we look, also known as point of gaze. A light source, such as near-infrared light, is directed towards the center of the eyes (pupil), causing detectable reflections in both the pupil and the cornea (the outer-most optical element of the eye). These resulting reflections, the vector between the cornea and the pupil, are tracked by an infrared camera. This is the optical tracking of corneal reflections, known as pupil center corneal reflection. These measurements are carried out by an eye tracker, a sensor or sensing unit that records the position of the eyes and the movements they make.

A face shield is a device or item of personal protective equipment (PPE), which aims to protect the wearer's entire face (or part of it) from trauma, injury or hazards. In this document and the appended claims, face shields, visors, goggles, and eye shields are used synonymously. These devices can be attached to a helmet or worn separately.

Fixation refers to a collection of relatively stable gaze points that are near in both spatial and temporal proximity. During fixation, the eyes hold steady on an object, and thus fixation reflects attention to a stimulus. A number of studies have associated fixation-related metrics to cognitive effort and the number of fixations has been shown to strongly correlate with task performance. Because task performance is also correlated with effort expenditure, this result suggests a link between fixation frequency and cognitive effort.

Focused position of the eyes is defined as the position or orientation of the eyes to provide a clear image of a visual element, visual object, or target of interest on the fovea.

Foveal Fixation Stability (FFS) refers to the ability to maintain an image on the fovea, which is crucial for the visual extraction of spatial detail. If the target image moves 1° from foveal center, or if random movement of the image on the fovea exceeds 2°/sec, visual acuity degrades substantially. Either of these conditions may occur if deficiencies in oculomotor control compromise the ability to maintain target alignment within these limits. Many aspects of oculomotor function do change with age. For example, smooth pursuit movements slow with age, and the range of voluntary eye movements becomes restricted, especially for upward gaze. DVA, FFS, and the vestibulo-ocular reflex decline with age.

Foveated rendering is a process which renders most of the view into a virtual world at lower resolution except for the exact area directly in front of where the user's eye is pointed. That area in front of the eye—where humans perceive the greatest detail—is rendered at a higher resolution.

Gaze also serves as a reliable indicator of attention and can reflect cognitive effort. Additionally, other major eye movement behaviors, such as fixations, saccades, blinks, and pupillary responses can provide distinct information about cognitive effort in response to task demand.

Global Shutter is defined as an imaging sensor that is capable of simultaneously scanning the entire area of an image. This is contrasted with a rolling shutter where the image area is scanned sequentially, typically from the top to bottom. Some consumer and industrial machine vision and 3D sensing need a global shutter to avoid motion blur, Target applications include facial authentication and eye tracking.

Hologram is defined as a three-dimensional image reproduced from a pattern of interference produced by a split coherent beam of radiation (such as a laser). It represents an image created by a photographic projection of a recording of a light field and appears as a three-dimensional representation on a two-dimensional object.

The definition of inertia is that objects remain in motion or at rest unless acted on by an outside force. A body at rest would stay at rest and a body moving through space would continue moving through space unless an external force (like friction or gravity) caused it to slow down or stop.

Kalman filtering (also known as Linear Quadratic Estimation (LQE)): an algorithm that uses a series of measurements observed over time, containing statistical noise and other inaccuracies, and produces estimates of unknown variables that tend to be more accurate than those based on a single measurement alone, by estimating a joint probability distribution over the variables for each timeframe.

Linear velocity is defined as the speed and direction of a physical object that is moving in a straight line. It is the rate of change of the object's position with respect to time.

Machine Learning is defined as the science of getting computers to learn and act like humans, and improve their learning over time in autonomous fashion, by feeding them data and information in the form of observations and real-world interactions. Machine Learning fundamentally is the practice of using algorithms to parse data, learn from it, and then make a determination or prediction about something in the world. This entails getting computers to act without being explicitly programmed and is based on algorithms that can learn from data without relying on rules-based programming.

Near accommodative triad: The near/accommodative response is a three-component reflex that assist in the redirection of gaze from a distant to a nearby object. It consists of a pupillary accommodation reflex, lens accommodation reflex, and convergence reflex.

Nystagmus is a description of abnormal involuntary or uncontrollable eye movement, characterized by jumping (or back and forth) movement of the eyes, which results in reduced or limited vision. It is often called "dancing eyes". Nystagmus can occur in three directions: (1) side-to-side movements (horizontal nystagmus), (2) up and down movements (vertical nystagmus), or (3) rotation of the eyes as seen when observing the front of the face (rotary or torsional nystagmus).

Ocular Parameters measurable factors that define and determine the components, actions, processes, behavior and functional ability of the eye, eyeball and eyelid. Included in ocular parameters are eye muscle movement responses which can be detected or measured, including the ocular reflexes, ocular saccades, pupillometry, pursuit tracking during visual pursuit, vergence, eye closure, focused position of the eyes, dynamic visual acuity, kinetic visual acuity, retinal image stability, foveal fixation stability, and nystagmus. Reflexes included in the measured ocular parameters or eye muscle movement responses include the vestibular ocular reflex, pupillary light reflex, pupillary dark reflex, near accommodative triad, corneal reflex, palpebral oculogyric reflex (Bell's reflex) and the optokinetic reflex. Measuring movements of eye includes the extraocular muscles (which move/rotate the eye), the levator (which raises the eyelid), the ciliary muscles (which helps to focus by changing the lens shape) and the pupillary muscle (which dilates or constricts the pupil). The use of measuring eye muscle movement responses, with eye tracking, have been shown to have significant value in detecting, measuring and monitoring or managing human health conditions, including but not limited to: concussions, traumatic brain injury, vision impairment, neurologic disorders or the neurologic status, cognition, alertness, fatigue and the situational awareness of humans. Additionally, these eye muscle movement responses can provide methods for detecting, measuring, monitoring and managing physiologic impairments due to alcohol and drugs because of their effect on the brain, brainstem and oculomotor responses.

Ocular reflexes are involuntary responses that are usually associated with protective or regulatory functions' They require a receptor, afferent neuron, efferent neuron, and effector to achieve a desired effect.

Optokinetic nystagmus: The optokinetic reflex, or optokinetic nystagmus, consists of two components that serve to stabilize images on the retina: a slow, pursuit phase and a fast "reflex" or "refixation" phase. The reflex is most often tested with an optokinetic drum or tape with alternating stripes of varying spatial frequencies.

Palpebral oculogyric reflex (Bell's reflex): The palpebral oculogyric reflex, or Bell's reflex, refers to an upward and lateral deviation of the eyes during eyelid closure against resistance, and it is particularly prominent in patients with lower motor neuron facial paralysis and lagophthalmos (i.e., incomplete eyelid closure).

Pupillary light reflex: The pupillary light reflex is an autonomic reflex that constricts the pupil in response to light, thereby adjusting the amount of light that reaches the retina. Pupillary constriction occurs via innervation of the iris sphincter muscle, which is controlled by the parasympathetic system.

Pupillary dark reflex: The dark reflex dilates the pupil in response to dark. It can also occur due to a generalized sympathetic response to physical stimuli and can be enhanced by psychosensory stimuli, such as by a sudden noise or by pinching the back of the neck, or a passive return of the pupil to its relaxed state.

Pupillometry refers to an objective way of measuring pupil size, and more specifically, the diameter of the pupil. Often pupil parameters are measured including: maximum, minimum and final pupil diameter, latency, amplitude and peak and average constriction and dilation velocities under numerous stimulus conditions including: dim pulse, dim step, bright pulse, bright step, bright red step and bright blue step.

Rotation is the movement of a geometric figure about a certain point. It is a transformation in which a plane figure turns around a fixed center point. In other words, one point on the plane, the center of rotation, is fixed and everything else on the plane rotates about that point by a given angle.

Saccades are rapid, ballistic movements of the eyes that abruptly change the point of fixation when gazing from one object to another.

Saccade accuracy refers to the eye's ability to quickly move and accurately shift from one target fixation to another. Saccade adaptation is a process for maintaining saccade accuracy based on evaluating the accuracy of past saccades and appropriately correcting the motor commands for subsequent saccades. An adaptive process is required to maintain saccade accuracy because saccades have too short a duration relative to the long delays in the visual pathways to be corrected while in flight.

Saccade amplitude refers to the size of the eye movement response, usually measured in degrees or minutes of arc. The amplitude determines the saccade accuracy. This is sometimes denoted using "gain". It is also described as the angular distance the eye travels during the movement.

Saccadic Inhibition. Studies of eye movements in continuous tasks, such as reading, have shown that a task-irrelevant visual transient (for example a flash of a portion of the computer display) can interfere with the production of scanning saccades. There is an absence or near-absence of saccades initiated around 80-120 ms following the transient. This inhibitory effect (termed saccadic inhibition SI) is also observed in simple saccade experiments using small visual targets and it has been suggested that SI may be like, or underlie, the remote distractor effect.

Saccade latency is the time taken from the appearance of a target to the beginning of an eye movement in response to that target. Disorders of latency (timing) can be seen with saccades, VOR and visual pursuit.

Saccade velocity is the speed measurement during the eye movement. High peak velocities and the main sequence relationship can also be used to distinguish micro-/saccades from other eye movements like (ocular tremor, ocular drift and smooth pursuit).

Sensor Fusion is an algorithm that combines sensory data or data derived from disparate sources such that the resulting information has less uncertainty than would be possible when these sources were used individually. The sensors can be of the same type (such as cameras for a stereoscopic image) or of differing types (such as combining accelerometer and gyroscopic data in a Kalman Filter). Sensor Fusion combines sensory data or data derived from disparate sources such that the resulting information has less uncertainty than would be possible when these sources were used individually. The term 'uncertainty reduction' in this case can mean more accurate, more complete, or more dependable, or refers to the result of an emerging view, such as stereoscopic vision (calculation of depth information by combining two-dimensional images from two cameras at slightly different viewpoints).

Situational awareness (SA) is defined as being aware of one's surroundings, comprehending the present situation, and being able to predict outcomes. It is a key human skill that, when properly applied, is associated with reducing errors of human performance activities.

Slippage occurs when a camera viewing a subject's eye moves out of phase with the subject's head. The slippage offset is an algorithm that accounts for slippage and computes an appropriate value that can be used to synchronize sensor data.

The smart sensing process can be defined as the input energy or signal which is detected by the sensing element, where the data is measured, and the transducer and associated circuitry transfers the data as output energy or signal to other sensing elements or devices.

Vergence is the simultaneous movement of both eyes to rapidly obtain or maintain single binocular vision or ocular fusion, or singleness, of the object of interest. It is often referred to as convergence or divergence of the eyes, to focus on objects that are closer or further away from the individual. The maintain binocular vision, the eyes must rotate around a vertical axis so that the projection of the image is in the center of the retina in both eyes. Vergence measurements can easily be performed. Normally, changing the focus of the eyes to look at an object at a different distance will automatically cause vergence and accommodation, known as accommodation-convergence reflex. Convergence is the simultaneous inward movement of both eyes toward each other, usually to maintain single binocular vision when viewing an object. Divergence is the simultaneous outward movement of both eyes away from each other, usually in an effort to maintain single binocular vision when viewing an object. Vergence tracking occurs in the horizontal, vertical, and/or cyclorotary dimensions.

Vestibulo-ocular parameters (VOP) in this document refers to the features of the eye muscle movements responses and reflexes which are measured with eye and head tracking sensors. It includes but is not limited to, the vestibulo-ocular reflex, ocular saccades, pupillometry, visual pursuit tracking, vergence, eye-lid closure, focused position of the eyes, dynamic visual acuity, kinetic visual acuity, retinal image stability, foveal fixation stability and nystagmus. Additionally, these parameter measures can provide an analysis of visual attention, fatigue, and cognition.

The Vestibulo-ocular reflex (VOR) is defined as a gaze reflex, by producing an eye movement in the direction opposite to head movement, thus preserving the image on the center of the visual field. It is a short latency reflex system, which generates a rotation of the eye with an amplitude equal and opposite to the direction of a head movement as a result of vestibular stimulation.

Visual pursuit means the movement of the eyes in response to visual signals. Such movements are under voluntary control in the sense that the observer can choose whether or not to track a moving stimulus.

Visual pursuit acceleration—this is the rate of change of the eye velocity. The first approximately 20 milliseconds of pursuit tends to be the same regardless of target parameters. However, for the next 80 milliseconds or so, target speed and position have a large effect on acceleration.

Visual pursuit accuracy is defined by the ability of the eyes to closely follow a moving object. The pursuit of targets moving with velocities of greater than 30°/s tends to require catch-up saccades. Smooth pursuit accuracy represents how closely the percentage of time the smooth pursuit velocity value remains within the target velocity value.

Visual pursuit latency is defined by the time from target appearance to the beginning of pursuit. The difficulty here is defining when pursuit begins. Usually it is measured from traces of eye velocity. It is often calculated by finding the intersection between two regression functions one fitted to velocity about the time of target appearance, and the second fitted over the initial part of the pursuit response.

Visual pursuit movements are much slower tracking movements of the eyes designed to keep the moving stimulus on the fovea. Such movements are under voluntary control in the sense that the observer can choose whether to track a moving stimulus. Although it may appear that our eyes are not moving when we fixate an object, in fact they are in continual small-scale motion, showing irregular drift and tremor, interspersed by miniature saccadic movements (less than 0.5 degrees). These fixational eye movements are essential to prevent our visual percept from fading. Pursuit consists of two phases—initiation and maintenance. Measures of initiation parameters can reveal information about the visual motion processing that is necessary for pursuit.

Visual pursuit tracking can be defined as measuring a person's eye movement ability to match a visual element or visual target of interest movement. Visual pursuit eye movements utilize some of the vestibulo-ocular reflex pathways and require a visual input to the occipital cortex to permit locking of the eyes onto a visual element, visual object or target of interest. Pursuit movements are described to be voluntary, smooth, continuous, conjugate eye movements with velocity and trajectory determined by the moving visual target.

Visual pursuit velocity—After pursuit initiation, speed of the eye movement (velocity) usually rises to a peak and then either declines slightly or oscillates around the target velocity. This peak velocity can be used to derive a value for gain (peak velocity/target velocity). It is usually near the velocity of the target. Instead of using peak velocity, it is also sometimes of interest to use measures of velocity at times relative to either target appearance or pursuit initiation. Eye velocity up to 100 milliseconds after target appearance can be used as a measure of prediction or anticipation. Velocity measured 100 milliseconds after pursuit begins reveals something about the ability of pursuit system in the absence of visual feedback.

Basic Science: Concussion and Traumatic Brain Injury (TBI)

Broadly speaking, a concussion, the most common type of traumatic brain injury, results from impact or impulsive forces to the head, neck or face and typically affects the central nervous system and the peripheral vestibular system. Most concussions meet criteria for mild traumatic brain injury. Mild traumatic brain injury (mTBI) has been defined as loss of consciousness less than 30 minutes and less than 24 hours and no skull fracture. A moderate TBI has a loss of consciousness greater than 30 minutes and less than 24 hours, with or without skull fracture. Severe TBI is characterized by loss of consciousness greater than 24 hours, with contusion, hematoma or skull fracture.

Due to the variability and subtlety of symptoms, concussions may go unrecognized or be ignored, especially with the pressure placed on athletes to return to competition. There is public consensus that undiagnosed, and therefore untreated, concussions represent a significant long-term health risk to players.

Closed head injury can cause several different types of brain injury including coup, contre-coup, acceleration-deceleration trauma, rotational trauma and molecular commotion. Acceleration-deceleration trauma causes discrete lesions which affect only certain areas of the brain. Both rotational trauma and molecular commotion cause diffuse damage that impairs many aspects of brain functioning. Acceleration-deceleration trauma occurs when the head is accelerated and then stopped suddenly, as with players colliding, which can cause discrete, focal lesions to two areas of the brain. The brain will suffer contusions at the point of direct impact and at the site directly opposite the point of impact due to the oscillation movement of the brain within the skull (e.g., coup or site of contact and contrecoup or opposite site of contact respectively). Trauma results from the oscillation (bouncing) of the brain against bony projections on the inside of the skull. Brain injuries may also occur as a result of acceleration-deceleration trauma unaccompanied by impact. The prefrontal areas and the anterior portion of the temporal lobes are the parts of the brain most often affected by acceleration-deceleration trauma. Thus, if the brain is repeatedly propelled against the front part of the skull, there is likely to be major injuries. Rotational trauma occurs when impact causes the brain to move within the cranium at a different velocity than the skull. This results in a shearing of axons within the upper spinal cord, brainstem and midbrain. Because this type of injury damages neural connections rather than gray matter, it can affect a wide array of cerebral functions and should therefore be considered a type of diffuse injury. Molecular commotion is a disruption in the molecular structure of the brain which may cause permanent changes in both white and gray matter. This type of diffuse brain injury may occur in the absence of discrete lesions.

The major effects of trauma on the brain can be divided into two categories: primary and secondary (or late) effects. The primary effects are those that are caused directly by the head trauma and include concussion, contusion, and laceration of the central nervous system.

Concussion is a reversible state of diffuse cerebral dysfunction associated with a transient alteration in consciousness. Most often there is a brief period of loss of consciousness. However, athletes may be only severely stunned or dazed. Typically, there is loss of memory for recent events (retrograde amnesia), and this may extend for some seconds or minutes prior to the injury and, rarely, with more severe impact, for days or more. A variable period of inability to learn new material (anterograde amnesia) typically follows recovery of consciousness and may be dense enough to leave the individual with no memory of early post injury occurrences. Rarely, some players are unable to remember ongoing occurrences. The retrograde amnesia is presumed to be caused by a mechanical distortion of neurons, probably in the temporal lobes, which consolidate the memory trace. The anterograde amnesia is presumed to be the result of distortion of the mesial temporal-limbic circuits known to be necessary for learning.

The underlying pathophysiology of concussion appears to be a shearing effect. Rapid displacement of the head, in either acceleration or deceleration injury, causes a swirling of the cerebrum within the cranium, and shearing forces play most markedly at the junctions between brain tissues of different density and location. Rotational injuries may be particularly damaging, since the brain stem torques while there is a lot of inertia against the rotation of the cerebral cortex. This results in torsion of the nerve fibers in the core of the brain (i.e., the reticular activating system). Another major zone of diffuse axonal injury is the interface between gray and white matter. It is here and in the core of the rostral brain stem that microscopic evidence of ruptured axons can be found pathologically.

Contusions of the brain are bruises usually associated with more severe trauma than necessary for concussion. They are most prominent at the summits of gyri, the cerebral poles (particularly the frontal poles and the anterior temporal lobe), and portions of the brain stem. All these regions lie close to the bony and dural surfaces of the cranial cavity. They may directly underlie the site of the violent blow to the cranium or may be opposite the site of impact (contrecoup). The contusions can usually be seen acutely on CT or MRI scans.

Laceration of the brain usually follows cranial trauma severe enough to cause fracture of the skull and penetrating injury to the brain by skull fragments or foreign objects. However, fracture of the skull need not be associated with laceration or contusion or major concussion. On the other hand, laceration may on occasion occur with severe shearing forces unassociated with fracture. Usually some form of hemorrhage (intracerebral, subdural, epidural) is associated with laceration.

The secondary effects of cranial trauma that may further compromise brain function are edema, hypoxia, hemorrhage, infection and epilepsy. Edema may be the result of diffuse shearing of capillary, glial, and neuronal membranes or may be secondary to local contusion or laceration. Edema can generate local pressure that can compromise both arterial and venous cerebral blood flow, causing ischemia and more edema. This may precipitate a vicious cycle sometimes impossible to reverse. The mass effect of edema, focal or diffuse, can cause rostrocaudal brain stem deterioration (possibly with herniation), a major cause of delayed death from head trauma. Increased intracranial pressure ICP), mostly due to edema but added to by any intracranial bleeding, is a major cause of secondary injury. High pressure decreases the perfusion pressure in brain blood vessels (since the perfusion pressure is the mean arterial pressure minus the intracranial pressure). If this is too low, there will be further damage to neural tissue due to ischemia, which will result in further edema and an even greater increase in pressure.

Intracranial hemorrhage, arterial or venous, intra- or extracerebral, is a frequent sequela of cranial trauma and may be great enough to cause rostrocaudal deterioration of neural function and death if not recognized and attended to immediately. Rostrocaudal deterioration, if rapid, may itself cause hemorrhage by downward stretching and tearing of the paramedian penetrating arteries of the midbrain and pons. Both epidural and subdural hematoma are extracerebral. Acute subdural hematomas are seen less frequently. They are usually associated with head trauma severe enough to cause skull fracture and cerebral contusion or laceration. A subarachnoid hemorrhage (SAH) involves bleeding into the space between the surface of the brain (the pia mater) and the arachnoid, one of three coverings of the brain. The hemorrhage is presumed to arise from angular forces that cause shearing of vessels as acceleration/deceleration movement of the brain occurs with linear/tangential/rotational injuries. The bridging veins tend to shear where they enter the dura after passing through the thin subdural space between the dura and arachnoid. An intracerebral hematoma can have a high mortality and the residual dysfunction of survivors is severe.

Arterial dissection may affect the carotid or vertebral arteries. This is usually associated with a tear in the intimal lining of the artery and an accumulation of blood in the media. Stroke may result from blockage of the artery or its branches or from artery-to-artery emboli arising from the site of vessel damage. The weakened artery may also rupture (often into the subarachnoid space) with potentially catastrophic results. Herniation, the process of squeezing brain tissue from one intracranial compartment into another, is often the terminal occurrence since this produces permanent damage in the region of herniation.

Pathologic Findings in the Brain with Trauma

Impact forces may cause linear, rotational, or angular movements of the brain, and more commonly a combination of these movements. In rotational movement, the head turns around its center of gravity, and in angular movement it turns on an axis not through its center of gravity. The amount of rotational force is thought to be the major component in concussion and its severity. As the angular acceleration increases, the risk of mild traumatic brain injury increases respectively.

It is thought that the forces from the injury disrupt the normal cellular activities in the reticular activating system located in the midbrain and diencephalon, and that this disruption produces the loss of consciousness often seen in concussion. Other areas of the brain that may be affected include the upper part of the brain stem, the fornix, the corpus callosum, the temporal lobe, and the frontal lobe. Severe centrifugal forces exert tremendous shearing pressures on the brainstem and upper spinal cord. A form of neurodegeneration reported in professional football players is "Chronic Traumatic Encephalopathy" (CTE). In addition to football players, CTE has been reported in other athletes involved in violent blows to the head, in traumatic military activities and in a few non-athletes with a history of TBI.

The syndrome of CTE begins insidiously, usually many years after the individuals have stopped playing sports or their other activities, with inattention, mood and behavior disturbances, confusion, and memory loss, and progresses inexorably over many years to a stage of full-blown dementia and parkinsonism. The brain, in CTE, shows atrophy, dilatation of the lateral and third ventricles, and thinning of the corpus callosum. Microscopic examination reveals hyperphosphorylated tau (p-tau) deposition in neurons, astrocytes, and cell processes around small vessels. These changes are patchy and affect the deeper parts of cerebral sulci. Other neurodegenerative pathologies, including beta amyloid deposition in the form of diffuse or neuritic plaques, amyloid angiopathy, TDP-43-inclusions may co-exist with p-tau deposition. Tau deposition is the key cellular change in CTE. The cause of CTE is thought to be TBI, especially repeated cerebral concussions and sub-concussive trauma. In the acute phase of a concussion, especially following side-to-side hits to the head, diffuse axonal injury (DAI) can occur and triggers the release of tau and beta amyloid in the brain. This, along with cerebral hypoxia, excitotoxicity and inflammatory mediators, set in motion a progressive destructive cascade that causes neurodegeneration many years later.

Diffuse axonal injury (DAI) is a special traumatic lesion, which occurs following blows to the unsupported head. During such injuries, the cerebrum goes into a back and forth gliding motion, pivoting around the brainstem. The brainstem, together with the cerebellum, is held firmly fixed by the tentorium, and the falx prevents side-to-side motion. Axons are stretched but do not snap from this injury. Their sudden deformation causes changes in the axonal cytoskeleton (compaction of neurofilaments, fracture of microtubules) that lead to an arrest of the fast axoplasmic flow. Components of this flow, including mitochondria and other organelles, accumulate proximal to the lesion and cause axonal swellings (spheroids). Some axons with mild lesions probably recover but many eventually rupture. It takes several hours from trauma to axonal rupture. Influx of calcium through the stretched axolemma probably initiates the process that leads to the formation of spheroids. Mitochondrial dysfunction and neuroinflammation contribute to the local tissue injury. Ruptured axons undergo Wallerian degeneration leading to loss of neurological function. Loss of axons may lead to dying back of neurons. Thus, DAI is a multifaceted process that evolves over time. The swellings are located at nodes of Ranvier where the axolemma is more liable to deform because there is no myelin. Brain damage is most severe along midline structures (corpus callosum, brainstem) where the shear forces are greatest, and at the cortex-white matter junction because of the change in the consistency of brain tissue. Cerebral concussion is thought to be a mild form of DAI without permanent pathology. The loss of consciousness in concussion is probably due to a functional disturbance of the reticular activating substance of the brainstem. This is part of the central nervous system that is subjected to the highest twisting force during sagittal rotation of the hemispheres.

Illustrations of Anatomy and Biophysics for Impact Mitigation

Traumatic brain injury (TBI) results from impacts to the head, neck or face and affects the central nervous system, peripheral vestibular system or both. The center of rotation of a human's head is not at the same location as the center of the gravity of the brain. The center of rotation of a human head is at bottom of the skull, specifically above the region of the foramen magnum through which nervous tissue and support cells of the upper spinal cord ascend to meet the brain stem at the medulla oblongata. The pivot point around which the brain rotates upon receiving a rotational head impact is felt to be located in the region of the upper spinal cord and brainstem junction, (e.g., region of the obex). This area is located just above the center of the foramen magnum. Because the position of the foramen magnum is more posteriorly located in the skull base, it is functionally imperative to align the center of the helmet proximate over the center of rotation or the pivot point of the brain and specifically in this region of the upper spinal cord and brainstem junction which lies just above the foramen magnum. With a tangential impact to the head, the least concussive effect can be achieved by this proximate alignment of the rotational center of a circular helmet with the center of rotation of a human's head.

For reference, FIG. 1A shows a top view of a typical human skull at 90. The shape of a normal human skull, as seen in a horizontal planar view from the top, is elliptical, not spherical. More specifically, it is egg-shaped in that it comprises a roughly circular (or spheroid in three dimensions) back side that is joined to a longer prolate circle (or prolate spheroid in 3D) front side. A human skull has a ratio of breadth, shown at 86, to length, shown at 88, that is not 1:1 and is typically 3:4 when viewed in the horizontal (also known as axial or transverse plane) plane (i.e., the horizontal midplane of a spherical helmet). The shape and size of the human skull will vary depending on race, gender, and other factors. Various measurements are used to determine head size differences. For example, the distance from the glabella (smooth part of the forehead above and between the eyebrows) to the back of the head may vary in men from 18.3 to 21.7 cm with the average being 20.0 cm. Often the skull measurement is referred to as the Cephalic index, which is the ratio of head width expressed as a percentage of head length. The normal range is 76-80.9%. Head length is measured between the glabella (the most prominent point on the frontal bone above the root of the nose) and the most prominent part of the occiput in the midline. Long headed skulls (Dolichocephalic) have a cephalic index of 70-74.9, average skulls (Mesaticephalic) are in the range of 75-79.9 and more rounded shaped skulls (Brachycephalic) are 80 or greater.

Figure 1B:
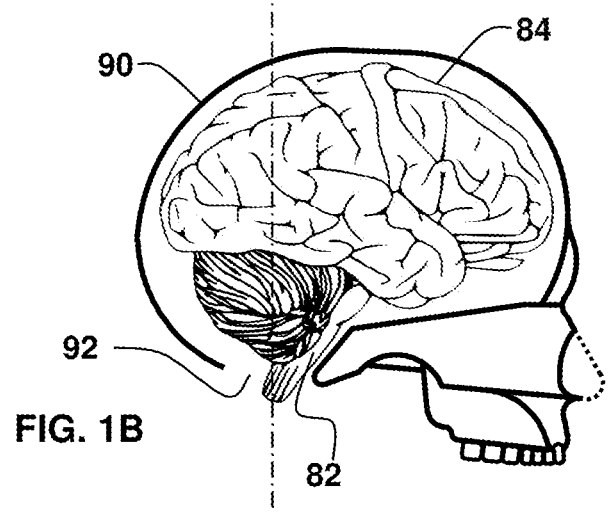
FIG. 1B shows a sagittal section view of the skull of FIG. 1A.

FIG. 1B shows a vertical side section view of the skull 90 of FIG. 1A, as well as parts of the brain. Within the bony skull 90, the cerebral cortex, 84, is the largest region of the cerebrum in the human brain and plays a key role in memory, attention, perception, cognition, awareness, thought, language, and consciousness. The cerebral cortex 84, is the most anterior (rostral) brain region and consists of an outer zone of neural tissue called gray matter, which contains neuronal cell bodies. Sitting between the cerebral cortex and the brain stem 82, is another segment of the brain, called the diencephalon, which combines the functions of the brain stem with the cerebral cortex. It is the posterior part of the forebrain that connects the midbrain with the cerebral hemispheres, encloses the third ventricle, and contains the thalamus and hypothalamus. The brainstem 82, is the region of the brain that connects the cerebrum with the spinal cord. It consists of the midbrain (superiorly located), the pons and medulla oblongata (inferiorly located). Motor and sensory neurons travel through the brainstem 82, allowing for the relay of signals between the brain and spinal cord. The cranial nerves are found in the brainstem 82. The brainstem 82, controls motor control signals sent from the brain to the body. This brain region also controls life supporting autonomic functions for the peripheral nervous system. The fourth cerebral ventricle located also in the brainstem, posterior to the pons and medulla oblongata. This cerebrospinal fluid-filled ventricle is continuous with the cerebral aqueduct and the central canal of the spinal cord. The spinal cord is the most important structure between the body and the brain. The spinal cord extends from the foramen magnum where it is continuous with the medulla to the level of the first or second lumbar vertebrae. It is a vital link between the brain and the body, and from the body to the brain. The spinal cord is 40 to 50 cm long and 1 cm to 1.5 cm in diameter. Two consecutive rows of nerve roots emerge on each of its sides. These nerve roots join distally to form 31 pairs of spinal nerves.

Figure 1C:
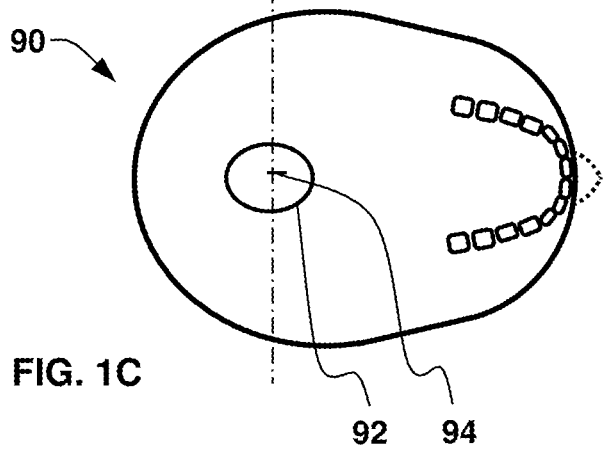
FIG. 1C shows a bottom view of the skull of FIG. 1A.

For reference, FIG. 1C shows a bottom view of the skull 90 of FIG. 1A. The foramen magnum 92, is located at the base of the skull in a posterior position. It is the largest foramen (bone aperture) in the skull base and the passage through which the spinal cord exits the cranial vault. The foramen magnum 92, is situated posteriorly in the occipital bone, and forms around the base of the brainstem (the medulla oblongata), separating the brain above from the spinal cord below. It is somewhat ovoid in shape and can vary in size and position in the posterior fossa, depending on race and sex. The foramen magnum 92, has also been identified by hidden (dotted) lines in FIG. 1A. The center of the foramen magnum 92, when seen from below, is in a plane just posterior to the mastoid tips on each side of the foramen. When viewed laterally, in the mid-sagittal plane, the center of rotation of a person's head occurs just posterior to the plane between the mastoid tips and medially at the center of the foramen magnum 92, i.e., at the point labeled 94 in FIG. 1A and FIG. 1B. FIG. 1A, FIG. 1B, and FIG. 1C have all been aligned so this center of rotation of the head falls on the same centerline. The mid-sagittal plane is equivalent to the horizontal midplane at the level of the foramen magnum 92. Seen laterally, the mid-sagittal plane is equivalent to the midplane of a spherical helmet when worn normally by a person.

In FIG. 1B, the foramen magnum 92, can be seen in the lowest part of the posterior fossa of the skull. It is just above the foramen magnum area, 92, where the lower portion of the brainstem 82, (e.g., medulla oblongata) meets the upper spinal cord. The upper part of the spinal cord and medulla oblongata end on ventral wall of the 4$^{th}$ ventricle. The obex is the point in the human brain at which the fourth ventricle narrows to become the central canal of the spinal cord. It occurs above the level of the foramen magnum 82, and is therefore considered the point where the medulla becomes the spinal cord.

Referring to FIG. 1A, FIG. 1B, and FIG. 1C, the center of rotation of a human's head 94, occurs at bottom of the skull 90, specifically above the region of the foramen magnum 92, through which nervous tissue and support cells of the upper spinal cord ascends to meet the brain stem 82, at the medulla oblongata. It is in this area (e.g., above the center of the foramen magnum 92, or in the region of the obex), defined as the pivot point 94, around which the brain rotates upon receiving a head impact. Because the position of the foramen magnum, 92, is more posteriorly located in the skull base, it is functionally beneficial align the center of the helmet or head worn protection system proximate over the center of rotation or the pivot point of the brain, specifically in the region of the upper spinal cord and brainstem junction (e.g., in the region of the obex), above the foramen magnum. The least concussive effect can be achieved by this proximate alignment of the rotational center of a circular helmet with the center of rotation of a human's head. Specifically, the magnitude of a tangential impact is minimized by using a spherical shaped helmet (which has a circular shell when looked at in a horizontal mid-plane section) and aligning the center of the circular shell with the center of rotation of the head. The center of rotation of a human's head is not at the same location as the center of the gravity of the brain.

As will be discussed further, head impacts can be linear or tangential, but most often are comprised of both. It has been established that the greatest injuries to the head, resulting in concussions and CTE, are from the tangential component of impacts, which creates a rotational acceleration. Tangential speed and rotational velocity have been shown to have a stronger correlation with relative brain motion than any other kinematic parameter. Relative brain motion is directly proportional to the rotational acceleration. Rotational acceleration is directly proportional to the magnitude of a tangential impact multiplied by the distance from the rotational center of the head. The greater the tangential speed prior to impact, the greater the tangential impact and the greater the rotational acceleration. As the rotational acceleration increases, the probability of injury and incidence of a concussive impact also increases dramatically. Also, higher rotational accelerations create worse concussions. Decreasing the rotational acceleration decreases the concussion incidence. The functionality of an impact mitigation device, system, or method can be significantly improved by aligning the center of rotation of the impact mitigation device, system, or method with the center of rotation of the wearer's head. This proximate alignment centering feature functionally reduces rotational acceleration. As noted, it is not done as a design choice, nor is it done for aesthetic reasons. In fact, this functional alignment solution may even look aesthetically unbalanced, but science shows that this solution works. By mitigating the rotational acceleration, an impact mitigation device such as a helmet, will decrease concussions and/or other pathologic brain injuries.

Description of Helmet-Based Impact Mitigation Illustrations

Figure 2A:
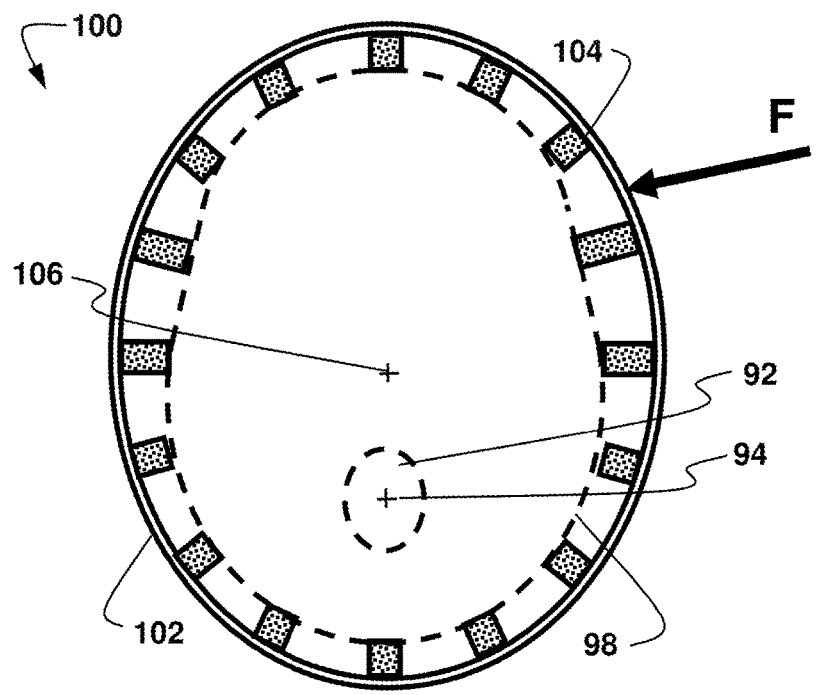
FIG. 2A is a horizontal section of a prior art helmet on a person's head.

Referring to the impact mitigation device drawings, FIG. 2A shows a horizontal section of a prior art helmet 100 on a person's head 98. The foramen magnum is shown at 92. The rotational center of the head is shown at 94. The prior art helmet 100 comprises a hard shell 102 and a set of pads 104 that conform to fit the person's head 98. Because the foramen magnum 92, center of head rotation 94, and spinal cord are located to the back of the person's head 98 and the pads 104 provide an approximately constant spacing between the person's head 98 and the hard shell 102, the center of the prior art helmet shell 106 is quite a distance from the rotational center of the head 94. A typical impact, shown at F, when applied to a prior art helmet generates a high rotational moment as will be further described below.

Figure 2B:
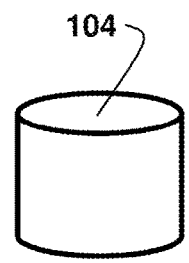
FIG. 2B is an isometric view of a prior art helmet pad.
Figure 2C:
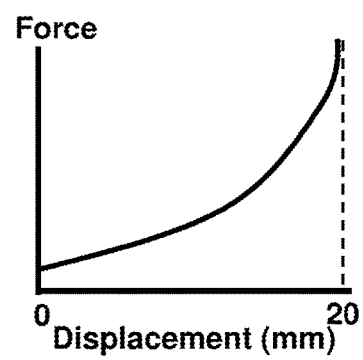
FIG. 2C is a force-displacement curve for a prior art helmet pad.

FIG. 2B shows an isometric view of the pad 104. FIG. 2C depicts the force-displacement relationship of the pad 104 in actual use. A typical prior art helmet pad 104 has a displacement of less than 20 mm in actual use before the pad is completely compressed. The force-displacement curve has a positive slope throughout its entire range. There is an initial force required before any displacement occurs because the pad is pre-loaded against the person's head (98 in FIG. 2A). This preload is shown by the y-axis intercept at 0 mm of displacement in FIG. 2C. The force rises steeply as displacement increases and the rate of increase per unit of displacement increases (i.e., the slope of the curve increases) until the displacement approaches the maximum displacement of the pad, at which point, the slope becomes asymptotically vertical because the pad 104 is fully compressed. This asymptotic line is shown at a value of 20 mm in FIG. 2C. The shape and characteristics of the force-displacement curve shown in FIG. 2C is typical of that for prior art helmets.

Figure 2D:
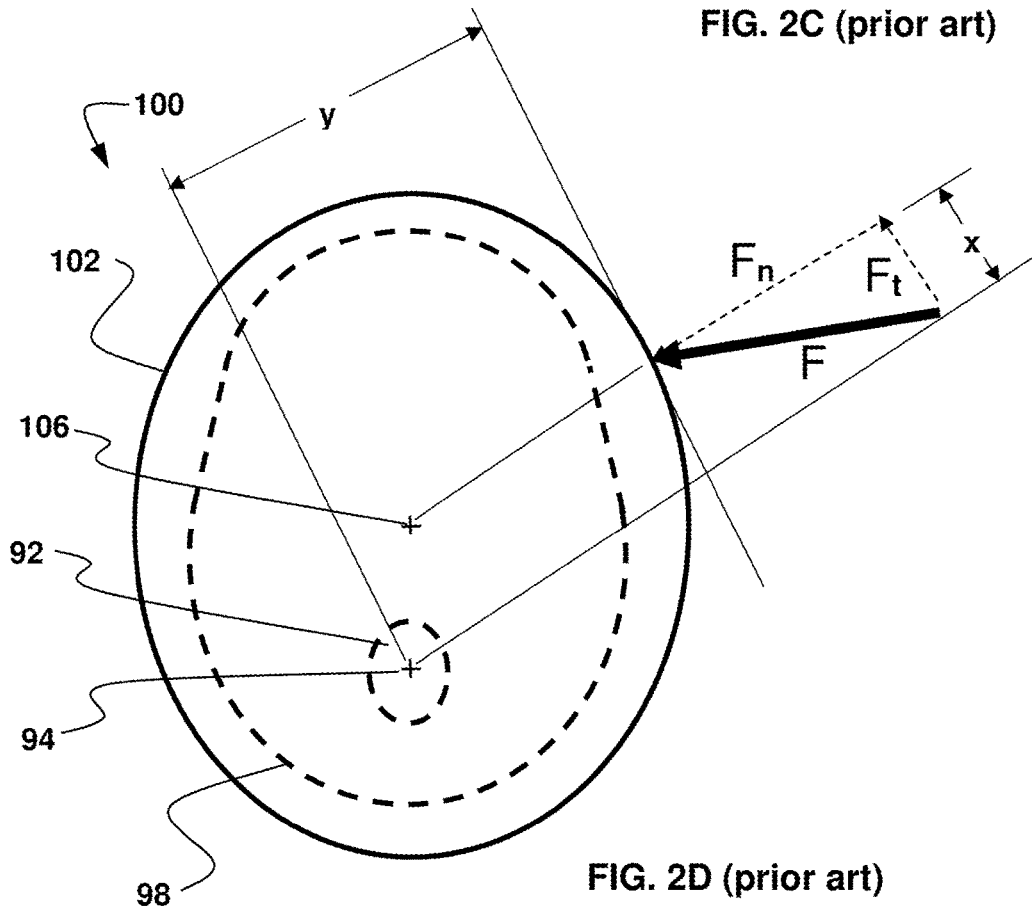
FIG. 2D shows the theory of operation of the prior art a helmet when subjected to an impact force at an arbitrary point.
Figure 3:
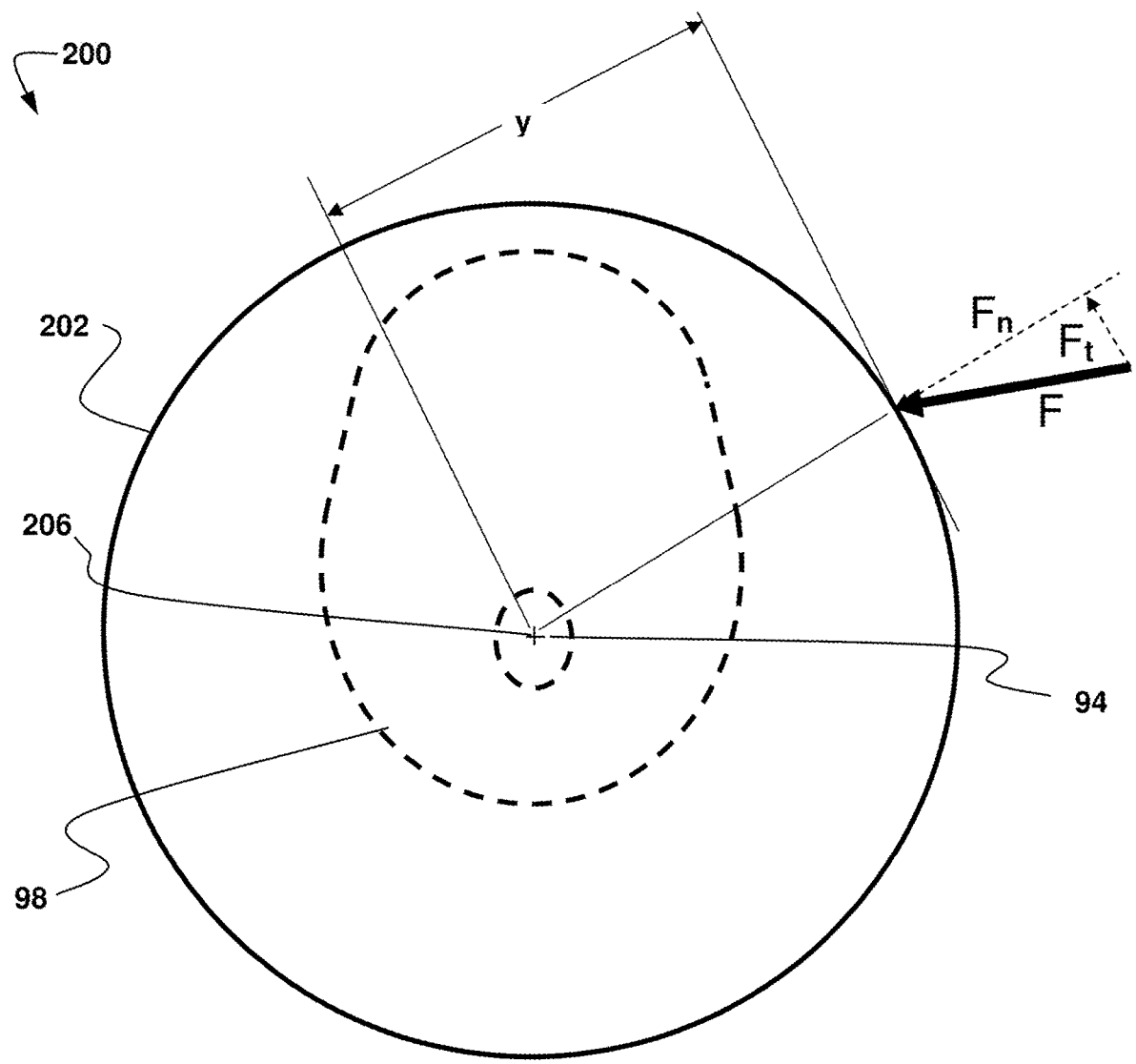
FIG. 3 shows the theory of operation of the top view of a spherical helmet that has been aligned with the center of rotation of the head.

FIG. 2D provides a 2-dimensional view of the theory of operation of a helmet by showing the same prior art helmet, 100 as in FIG. 2A, on a player's head 98. The foramen magnum 92, rotational center of the head 94, hard shell 102, and center of prior art helmet shell 106 are also shown. The force F is shown impacting the hard shell 102 at an arbitrary point. In actual use, impacts F can occur in any location and any direction on the exterior of a helmet. The impact F can be decomposed into: a force Ft that is tangential to the curvature of the exterior of the helmet at the point of impact and a force Fn that is normal to the exterior of the helmet at the point of impact. The tangential component of force Ft generates a rotational moment on the helmet 100 and hence on the brain stem and spinal cord transition located in the foramen magnum 92. The magnitude of this rotational moment depends on: (a) the coefficient of friction between the helmet exterior (in this case the hard shell 102) and the body that produced force F; (b) the perpendicular distance between the point of impact and the rotational center of the head 94, a distance shown at y; and (c) whether the collision is elastic, inelastic, or partially elastic. The tangential component of force Ft can also generate an axial force on the hard shell 102 and hence on the region of the foramen magnum 92. The magnitude of this axial force depends on (a) the coefficient of friction between the helmet exterior (in this case the hard shell 102) and the body that produced impact F and (b) whether the collision was elastic, inelastic, or partially elastic. Based on the preceding and as shown in FIG. 2D, one can minimize the effect of the tangential component of force Ft on the foramen magnum 92 region by minimizing the coefficient of friction between the helmet exterior and the body that produced force F and by making the center of curvature of the helmet exterior at the point of impact align as closely as possible with the rotational center of the head 94. More specifically the tangential component of force Ft will produce no force on the foramen magnum, 92, region if (a) there is a zero coefficient of friction between the helmet exterior and the body that produced impact F or (b) if the center of curvature of the helmet exterior at the point of impact is in the same location as the rotational center of the head 94, and the helmet exterior is coupled to the rest of the helmet in a way that allows the helmet exterior to rotate freely around the other elements of the helmet. In order for the center of curvature of the helmet exterior to be in the same location as the head rotational center for all tangential forces at all locations on the helmet, the helmet exterior must be spherical and the spherical helmet center must be at the same location as the center of the rotation of the person's head 94. This idealized configuration is shown in FIG. 3. Referring to FIG. 3, the rotational center of the head 94, has been aligned with the inertial center of an improved outer shell 202 having an inertial center 206 that is co-located with the rotational center of the head 94.

Further referring to FIG. 2D, the normal force Fn creates an axial force on the foramen magnum region 92. The normal force Fn can also create a bending moment (i.e., rotational force) at the rotational center of the head 94, if the center of the radius of curvature of the helmet exterior at the point of impact is not aligned with the rotational center of the head 94. For the geometry shown, a line drawn perpendicular to the tangent line the point of impact will intersect the center of prior art helmet shell 106. Therefore, for the geometry and impact shown, the size of bending moment created by Fn equals the offset between the center of the prior art helmet shell 106 (illustrated as x in FIG. 2D) multiplied by the magnitude of the normal force Fn. Note that if there is friction between the impact source and the hard shell 102 and the shell 102 is not free to rotate about the person's head 98, then the tangential force Ft will produce an additional bending moment equal to Ft multiplied by the perpendicular distance between a line tangent to the point of impact on the hard shell 102 and a parallel line that intersects the rotational center of the head 94. This perpendicular distance is shown at y in FIG. 2D. Referring to FIG. 3, the normal force Fn produces no bending moment if the radius of curvature of the helmet exterior at the point of impact (i.e., the center of the helmet shell if the shell is spherical) is aligned with the rotational center of the head 94. By comparing FIG. 2D with FIG. 3, one can see that there is no "x" dimension in FIG. 3.

Figure 4A:
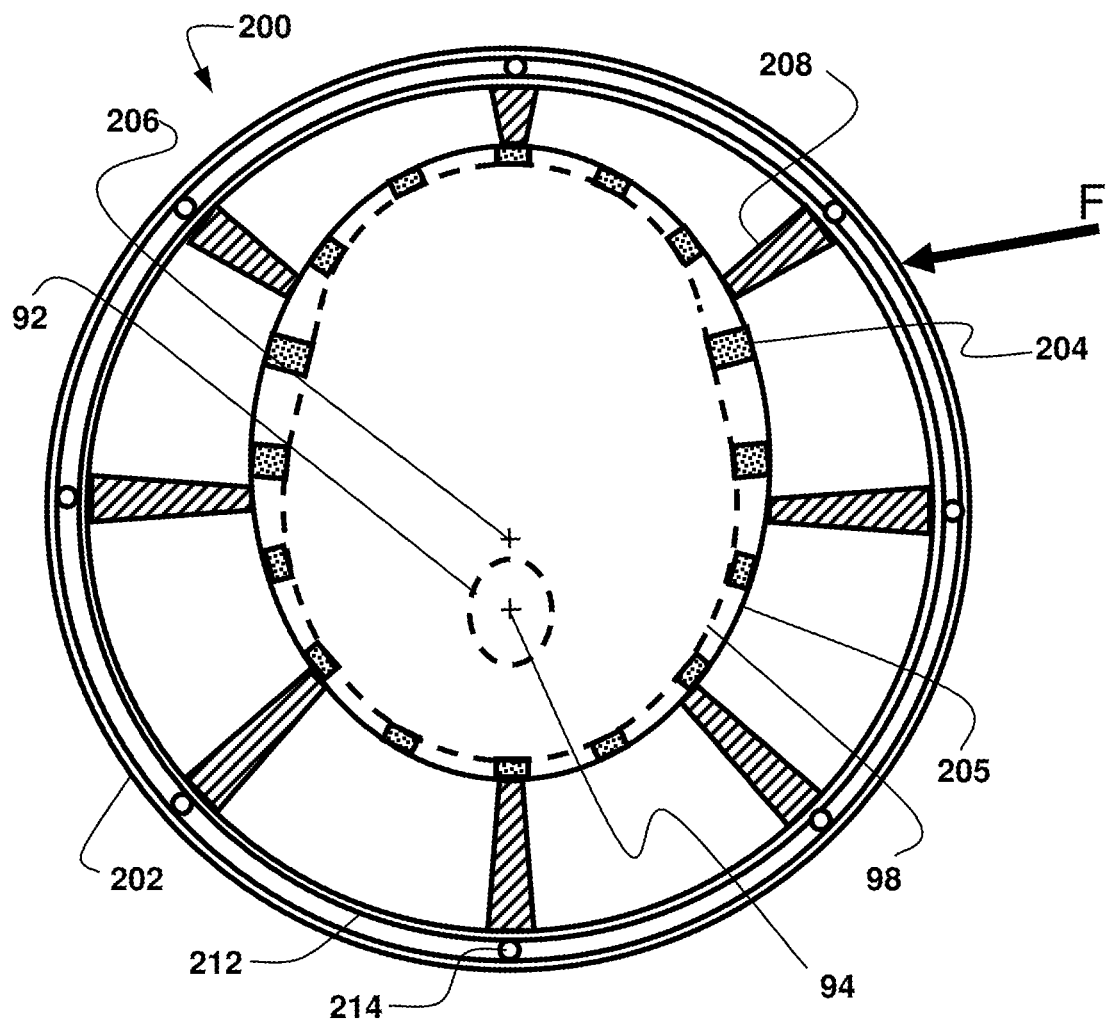
FIG. 4A is a horizontal section of the spherical helmet of FIG. 3.

FIG. 4A shows a horizontal section view of a rotationally centered impact reduction helmet 200 on a person's head. Like in FIG. 2A, the person's head is shown at 98, the foramen magnum is shown at 92, and the rotational center of the head is shown at 94. The embodiment of the impact reduction helmet 200 in FIG. 4A has several improvements over the prior art helmet 100 of FIG. 2A. A first improvement, shown in FIG. 4A, is that the head-conforming pads 204 are thinner. The head-conforming pads 204 are customized and configured to fit inside of a pad frame (or inner frame) 205 and press against the person's head, 98. In the improved helmet 200, the pad frame 205 is separate from the hard shell, shown at 202. The pad frame 205 is sized and shaped to conform as closely as possibly to the person's head 98, and custom fitted to each user. The pad frame 205 can be sized and shaped independently of the size and shape of the hard shell 202. By having a pad frame 205 that conforms as closely as possible to a person's head 98, the head-conforming pads 204 can be thinner than the pads 104 in the prior art design (FIG. 2A). In the prior art helmet (shown in FIG. 2A) the prior art pads 104 were configured to perform two functions: (a) to provide a comfortable fit on the person's head 98 and (b) to provide shock absorption. In the improved helmet, 200 FIG. 4A, shock absorption elements shown at 208 have been added to the system and these shock absorption elements 208 can be independent of the head-conforming pads 204. In the prior art shown in FIG. 2A, the pads 104 needed to be relatively thick to provide sufficient compliance to fit both big heads and small heads into the same shell 202. The improved helmet 200 of FIG. 4A allows a closer fitting of a pad frame 205 to a person's head 98. One of the ways to accomplish this closer fitting is to make the pad frame 205 from material that is initially flexible to fit the person's head 98 and subsequently hardened once the fit has been determined. Another technique for producing a custom pad frame 205 is to make a 3-dimensional scan of the person's head 98 and then to manufacture the custom pad frame 205 using a 3-dimensional printer. The methods for making this custom pad frame 205 can be any method or technique capable of being understood by anyone skilled in the art. The pad frame 205 can be rigid with the properties of being lightweight and strong. The pad frame (or inner frame) 205 could be made of materials such as carbon fiber, carbon fiber composites, graphene, ultra-high-molecular-weight polyethylene, boron nitride, lonsdaleite, linear acetylencic carbon, and/or other allotropes of carbon or carborundum.

Further referring to FIG. 4A, the shell 202 of the rotationally centered impact reduction helmet 200 is spherical. The use of a spherical shell 202 makes it is possible to minimize or completely eliminate the relationship between a tangential components of impact force (Ft shown in FIG. 2D) and any resulting rotational forces at the rotational center of the head 94. Rotational forces at the rotational center of the head 94, can be minimized or eliminated by either (a) minimizing friction between the source of impact and the spherical shell 202 or (b) allowing the spherical shell, 202, to rotate relative to an inner frame member, shown at 212.

The coefficient of friction between the source of impact and the spherical shell, 202, can be minimized by making the spherical shell out of a material that is "slippery" when relative to the materials used for the source of impact. Materials such as PTFE (polytetrafluoroethylene), PEEK (polyether ether ketone), polyimide, polyphenylene sulfide, nylon, acetal, and polyester are examples of materials that have a low coefficient of friction in most environments.

The spherical shell, 202, can be allowed to rotate relative to an inner frame member, 212, through the use of rotational couplers, shown at 214. This rotational friction reduction could also be accomplished through the choice of materials that provide a low coefficient sliding contact, such as the materials such as PTFE that were mentioned in the previous paragraph with regard to the spherical shell.

Note that the improvements shown in FIG. 4A can either be used with a spherical shell, which can allow rotation about two perpendicular axes or with a shell that has a circular geometry in one axis, but is non-circular about an axis perpendicular to this axis. In the latter case, the helmet could rotate freely about an axis aligned with the rotation of the upper spinal cord, but would not rotate about an axis perpendicular to this spinal rotation axis.

Further referring to FIG. 4A, the rotational center of the shell 202, is shown at the point labeled 206. This rotational center 206, is brought much closer to the rotational center of the head 94, than in the prior art shown in FIG. 2A and FIG. 2D. This repositioning of the rotational center 206, backwards on the person's head 98, further reduces the rotational forces as explained previously when describing the theory of operation and FIG. 4A. In an ideal case, the rotational center 206, would be the same as the rotational center of the head 94. Note that the center of the radius of curvature of a circle is the same as the center of the circle, and the same applies to a sphere. Thus, the center of curvature for a shell having a circular geometry will be the same as the rotational center 206. It is also the case that the center of the moment of inertia of a circle, or anything having a circular geometry will be the rotational center of that circle or item having a circular or spherical geometry. To summarize, the magnitude of a tangential impact can be minimized using a spherical shaped helmet (which has a circular shell when looked at in a horizontal section) when aligning the center of the circular shell with the center of rotation of the head. As the horizontally viewed center of a circular shell becomes more closely aligned with the rotational center or pivot point of a human head (e.g., in the region of the upper spinal cord and brainstem junction, (in the region of the foramen magnum), the tangential impact on the human can be decreased.

Further referring to FIG. 4A the customized pad frame 205, and inner shell 212 (or inner frame member) are connected through shock absorption elements 208. In the embodiment shown in FIG. 4A, the shock absorption elements 208, are fixed at one end to the pad frame 205, and at the other end to a shell 212, that is coupled to the outer shell 202. The shock absorption elements 208, shown in FIG. 4A can be sized to provide greater spacing between the customized pad frame 205, and the inner frame member 212, at the sides and the rear of the rotationally centered impact reduction helmet 200, than at the front of the improved helmet 200, to (a) allow a spherical shell 202, to fit onto a head that is oval and (b) allow the helmet rotational center 206, to be located proximate to the rotational center of the head 94—ideally the two centers of rotation would be at the same point.

Figure 4B:
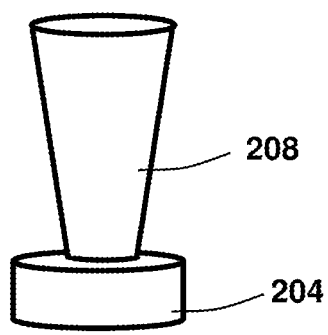
FIG. 4B is an isometric view of a head conforming pad and a shock absorption element in series.

Referring to FIG. 4B the head-conforming pads 204, and the shock absorption elements 208, operate in series in response to an impact. In the embodiment show in FIG. 4A, the shock absorption elements 208, are sized to provide a significantly greater displacement of the shell 202, relative to the person's head 98 than in the prior art design shown in FIG. 2A. The total displacement for even the shortest impact absorption elements 208, located near the front of the improved helmet 200, in FIG. 4A can be greater than the displacement of the largest pad 104, in the prior art design FIG. 2A. The higher displacement is needed to provide the distance required to decelerate from the typical speeds of impact in football while minimizing the risk of exceeding the accelerations that cause concussions.

The head conforming pads 204, and/or the customized shock absorption elements 208, can further comprise sensors and/or transducers to detect, measure and transmit biomedical and/or physical information related to the protective structure, in the form of visual, haptic or auditory signals to the user or to another device remotely, which can be viewed by others. These sensors/transducers could be self-adjusting, could interact with other sensors and can respond by changing form or characteristics when sensing elements/transducers on the outer rigid shell detect an impending violent blow which may require greater resistance to deformation.

In another embodiment, the head conforming pads 204, can comprise sensing elements and/or transducers to detect, measure and transmit biometric or abnormal physiologic and/or biochemical information related to health of the user, in the form of a visual, haptic or auditory signal to the user, to the protective structure worn, or to another device remotely, which can be viewed by others.

The head contains 28 bones and 17 named fusions where the bones are joined. The cranium or cranial vault is the portion of the skull which encloses and protects the brain (e.g., the braincase) and is comprised of 8 bones. Each of these different bones have different areas of thickness. For example, the temporal bone, on the side of the cranium, is the thinnest bone of the skull. The occipital bone is the thickest skull bone, and the frontal bone is the second thickest bone of the skull. The bones of skull have a limited amount of elasticity. If the limits of elasticity are not exceeded, the bone will recoil to its normal shape and fracture will not occur. Fractures due to general deformation are usually fissured and they can occur in parts of the skull distant from the site of application of the force. Because some bones are thick, they are likely to be stiff and deform little when loaded. The majority of bones varied in thickness from 5 to 7 mm except temporal and parietal bones, which can vary from 3-4 mm. Also, the skull bones are not uniform plates and have great variations in thickness and shape at different points, depending on age, sex, culture and hereditary factors. The pericranium is a dense membranous outer periosteum of the calvarium. It covers the external surfaces of the frontal, parietal, and occipital bones deep to the subgaleal areolar tissue and extends as far laterally as the superior temporal line on each side. The pericranium also varies in thickness from individual to individual and from region to region. Generally, however, the pericranium is thicker frontally than at the vertex. The temporal bone has little pericranium and can offer little resistance to bending. It is a simple fact that a thin plate of bone will break first because of the poor resistance when compared to thick bone. The importance of these anatomic features such as the varying skull bone thickness and thinness can be correlated with skull fractures sites and intracranial damage. These anatomical features of the skull can be correlated with specific placement needs of the head conforming pads 204, as seen in FIGS. 4A, 4B, 5A and 7A, and/or the customized shock absorption elements 208, 306, 304, as seen in 4A, 4B, 5A. 6A, 6B, 6C, 6D, 6E and 6F, having different thickness, construction, shapes, resiliency, elasticity, rebound rates, different impact mitigation elements, different purposes and force displacement characteristics. Specifically, in embodiments of the invention, different types of head conforming pads and/or shock absorption elements can be selected and specifically placed, based on the anatomical features discussed, such as thickness or thinness of the cranial vault or the area near the most likely part of the brain for injury or for a specific purpose of measurement. As an example, shock absorption elements having different elastomeric properties, shape, size, rebound rate, or force displacement characteristics may be placed in the temporal area compared to the impact material selected and placed in the occipital region. The head conforming pads 204, are not just for comfort and adjustment of the helmet to prevent slippage and accommodate different sizes of heads. These pads as indicated, can have additional purpose of impact mitigation and for selected areas of the head, the properties of such pads can vary, depending on the area in which they are placed as mentioned above. They can also be used to assist other biochemical and/or physiologic measurement functions, with the use of attached or adherent sensors, which would be in contact with the skin in those anatomically chosen locations for the purpose the sensors were designed.

The head conforming pads 204, and/or the shock absorption elements 208, can be adjustable to maintain proper relationship of the outer shell 202, and the inner frame 212, both of which can be centered over the upper spinal cord in the region of the foramen magnum. The conforming pads/ cushions, 204 and 208, can be inflatable. Sensors and/or transducers in any of these elements can be specific to that component for the measurement of a specific function and can be anatomically and strategically positioned for more precise measurement for which the specific sensors and/or transducers are designed.

Figure 4C:
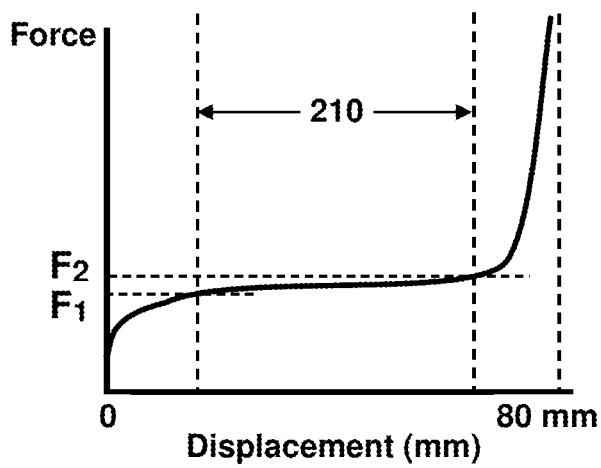
FIG. 4C is a force-displacement curve for a head confirming pad helmet pad and a shock absorption element in series.

FIG. 4C illustrates a force deflection characteristic for the head-conforming pads 204, and shock absorption elements 208, of the improved helmet 200, of FIG. 4A and FIG. 4B. To decelerate as much as possible without exceeding an unsafe (concussion-risky) G-force it is desirable to decelerate as linearly as possible. Since force equals mass times acceleration, this means that the resistance force of the shock absorption elements should be as linear as possible. As shown by the force displacement curve in FIG. 4C, and based on the calculations shown earlier, we would like to have a displacement of at least 60 millimeters in which the resistance force of the shock absorption elements 208, is as flat (i.e., constant) as possible. The table below illustrates the relationship between speed of impact, displacement in the linear region (shown at 210, in FIG. 4C and 354, in FIG. 7B), slope of the linear region (defined and calculated as [F2-F1]/F2), and maximum acceleration if this section of the force-displacement curve is responsible for dissipating the entire impact. The values in the table below for a slope of 1 were generated by assuming that jerk (the rate of change of acceleration as a function of time) is a constant. This generates the following simultaneous equations to be solved:

$$v=(1/2)j\ t^2 \text{ (if jerk is constant)}$$

$$x=(1/6)j\ t^3 \text{ (if jerk is constant)}$$

$$a=j\ t \text{ (if jerk is constant)}$$

where: x is displacement, v=velocity, a=acceleration, j=jerk, and t=time

| Impact speed | Slope | Displacement | Time | Maximum Acceleration |
|---|---|---|---|---|
| 10 meters/sec | 0 | 25 mm | 5 msec | 2000 m/sec² (200 g) |
| 5 meters/sec | 0 | 25 mm | 10 msec | 500 m/sec² (50 g) |
| 10 meters/sec | 0 | 50 mm | 10 msec | 500 m/sec² (50 g) |
| 5 meters/sec | 0 | 50 mm | 20 msec | 125 m/sec² (12.5 g) |
| 10 meters/sec | 1 | 25 mm | 7.5 msec | 2667/sec² (267 g) |
| 5 meters/sec | 1 | 25 mm | 15 msec | 667/sec² (67 g) |
| 10 meters/sec | 1 | 50 mm | 15 msec | 667/sec² (67 g) |
| 5 meters/sec | 1 | 50 mm | 30 msec | 167/sec² (16.7 g) |

Figure 5A:
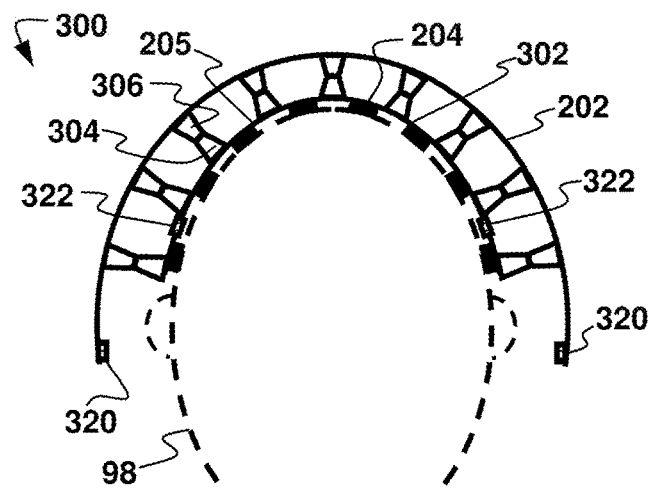
FIG. 5A shows a vertical section of an alternate embodiment helmet.

FIG. 5A shows a cross-section front view (i.e., a coronal view) of an alternate embodiment improved helmet 300, on a person's head 98. The alternate embodiment 300, is similar to the improved helmet 200, in FIG. 4A in that the alternate embodiment 300 comprises a plurality of head conforming pads 204 located closest to the person's head 98 and mounted in a pad frame 205. The alternate embodiment 300, is different from the improved helmet 200, of FIG. 4A in that the alternate embodiment 300, does not have an inner frame (212 in FIG. 4A) that can be rotationally coupled to the shell 202, in FIG. 4A. Instead, the alternate embodiment 300, has a plurality of customized compound shock absorption elements, each of which comprises a first elastically resilient impression, shown at 304, and a second elastically resilient impression, shown at 306. In the alternate embodiment 300, the second elastically resilient impression 306, is connected directly to the spherical shell 202 and the first elastically resilient impression 304, is connected to the pad frame 205.

Referring generally to the embodiments shown in FIG. 4A and FIG. 5A, one skilled in the art can imagine further combinations of the elements and configurations shown in these two figures. For example, another possible embodiment of the improved helmet could comprise compound shock absorption elements of the type shown at 304, and 306, in FIG. 5A with these elements attached on their outside to an inner shell like that shown at 212, in FIG. 4A. A further possible embodiment could be to have compound or non-compound shock absorption elements like those shown at 208, in FIG. 4A that attach directly to the shell of the type shown at 202, in FIG. 5A.

Referring further to FIG. 5A, the elastically resilient impressions 304, and 306, can be made of a variety of materials, including carbon fiber or nanometer-scale carbon nanotubes. They can also have a variety of shapes, resiliency, elasticity, rebound rates, different impact mitigation elements and force displacement characteristics. These elastically resilient impressions can be fluid (gas or liquid) filled sealed units. They can be plastic or rubber dimples. They can be metal or non-metal springs, such as leaf springs or coil springs. They can be dimples made from a material such as polyethylene or some other plastic, metal, rubber material, or any other material having at least some elasticity. They can be made of any other materials or implemented in any other configurations capable of being understood by anyone skilled in the art.

Further referring to FIG. 5A, the configuration of the helmet 300 can include sensors, shown at 320 and 322. The sensors shown at 320, are attached to the shell 202. The sensors shown at 322 are proximate to the user's head 98. These sensors 320, and 322, could also be attached to the wearer's body. The sensors 320 and 322, could be shielded from the wearer's body for safety reasons. The sensors 320, could be used to detect a variety of parameters, examples of which can include:

- detecting a rotational or angular acceleration, which might be useful in determining characteristics such as, the timing of an impact, the magnitude of an impact, the direction of an impact, or the effectiveness of the impact reduction system in reducing the severity of the impact;
- detecting an orientation, which might be useful in determining a characteristic such as the position of a person's body part at the time of an impact;
- detecting a velocity, which might useful in determining a characteristic such as the velocity at which an impact occurred;
- detecting a parameter of another object in the vicinity, an example might be detecting the location and velocity of other impact pads (such as helmets) being worn by other persons in the vicinity, which might be useful in identifying an impending impact;
- detecting a signal from another object in the vicinity, an example might be detecting an alarm signal coming from a device on another soldier in the vicinity;
- detecting other sensors such as those on other helmets in the vicinity or detecting some parameter or sensor associated with the person wearing the helmet, a feature that can allow the helmet to identify and/or respond to of the person wearing the helmet; and/or
- the sensors 322, could be used to detect a variety of parameters, examples of which can include detecting a biometric, physiologic and/or biochemical parameter associated with the wearer of the helmet. These sensors would be specifically anatomically located depending on the purpose for which the measurement is designed.

Examples of biometric, physiologic and/or biochemical parameters can include blood pressure, pulse, body temperature, oxygen saturation, electro-cardio activity, brain activity, neural activity, chemical levels in the sweat, such as sugars, electrolytes and/or cortisol.

The sensors shown in FIG. 5A can be connected to a processor that is part of the impact reduction system. This processor can include a memory element to store sensor data. This stored sensor data can be used for data logging, which can facilitate evidence-driven management of the sensing and data collection process, whereby data derived from the sensors could be used to repair, modify, or alter the responsiveness of a sensor or to alter the responsiveness of a sensor and/or alter the data being recorded from a sensor or to alter the frequency at which data is being recorded from a sensor. The sensor data can also be transmitted and this transmission can be in the form of a wireless protocol such as WiFi, Bluetooth, Zigbee (and related IEEE 802.15.4 and XBee), a cellphone signal, or any other wireless protocol capable of being understood by someone skilled in the art and using sensing elements/transducer materials which promote wireless connectivity. An example can be the use of materials for flexible electronics with faster transistors and semiconductors such as Graphene and Cyrene (dihydrolevogucosenone), which can provide higher concentrations and conductivity of graphene ink for wireless connectivity to the IoT as well as provide RF energy harvesting for low power electronics.

The sensor data can also be used to produce an alarm signal capable of being understood by a human, examples of which might include an audio alarm, a visual flashing red light, or a vibration or other tactile signal. The sensors 320 and 322 can be powered by a battery, by a generator, or by an external power source that sends its power over a wired or wireless method. Other power sources could include: a rechargeable lithium-ion battery, solar power, mechanical power, liquid-free and cobalt free battery, battery using waste graphite, 3-D battery, salt water battery, flexible nickel-metal hydride battery, ZIF-derived bifunctional air electrodes, knittable zinc-air batteries, combinations of graphene, hybrids of Magnesium Oxide, flexible nanowire networks harvesting energy from biological systems (moisture enabled electricity generation, flexible supercapacitor comprised of layers of flexible, 3D porous foam formed from graphene and silver electrodes, lead zirconate titanate coated with flexible metal foil, ultracapacitors or various other power supply materials or non-battery power sources and types known in the art. The sensors can be self-adjusting sensors that learn from data being received to better tune themselves to signals and discriminate these useful signals from other signals and background noise.

Figure 5B:
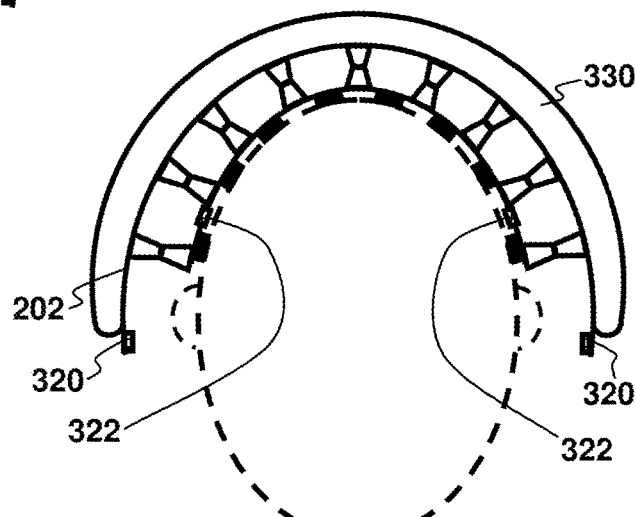
FIG. 5B shows the helmet of FIG. 5A further comprising an external airbag.

The sensors 320 and 322, shown in FIG. 5A can also be connected to an impact mitigation device such as an air bag (330 in FIG. 5B). This air bag 330 could be located anywhere outside of the shell 202. Thus, an impact-detecting or impact-anticipating sensor could issue a signal to the airbag system that causes the airbag to deploy, cushioning the impact and thereby reducing the magnitude of the impact and bodily damage to the person wearing the impact reduction system.

Figure 5C:
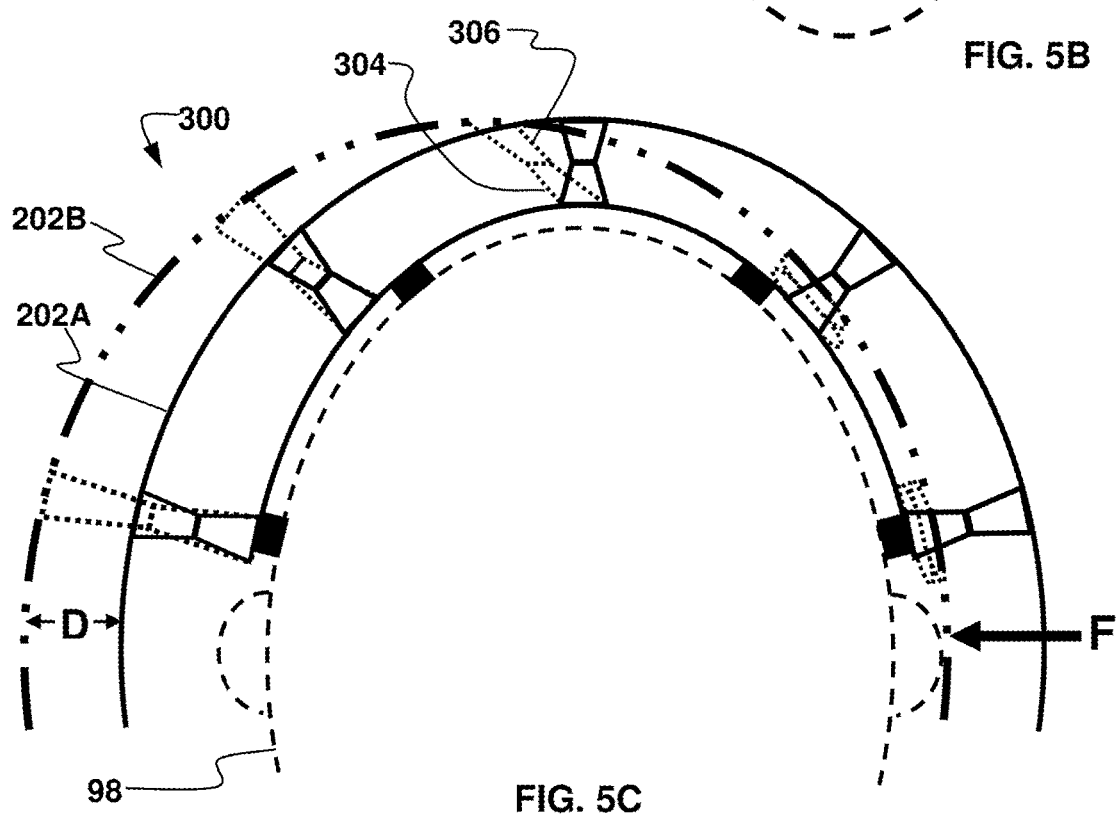
FIG. 5C shows the displacement of the helmet of FIG. 5A when subjected to a lateral force.

FIG. 5C shows the result of a side impact F on the helmet embodiment 300, that was also shown in FIG. 5A. More specifically, this shows the movement of the helmet shell from an initial position 202A to a final position 202B, on the opposite side, as a result of the applied force F. This applied force F causes a lateral displacement shown as dimension D in FIG. 5C. Examples of the displacement of the impact pads that were shown at 304 and 306, in FIG. 5A can be seen by dotted lines in FIG. 5C.

Figure 6A:
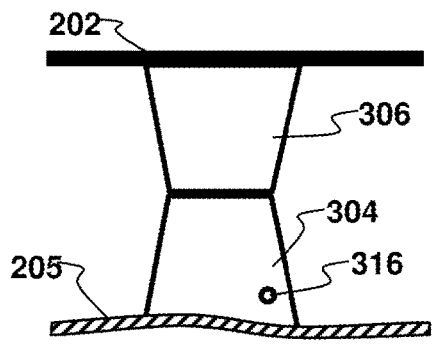
FIGS. 6A, 6B, and 6C are detailed views of two layers of elastically-resilient impressions in a serial configuration for use in a helmet.
Figure 6D:
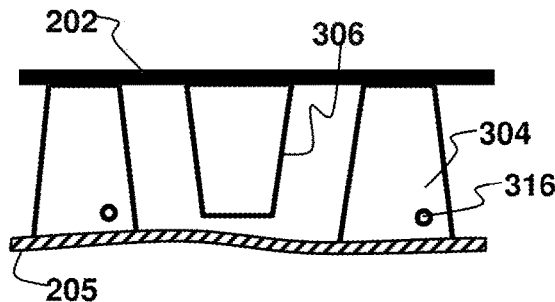
FIGS. 6D, 6E, and 6F are detailed views of elastically-resilient impressions in a parallel configuration for use in a helmet.
Figure 6B:
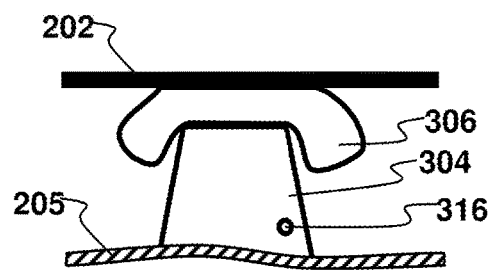
Figure 6E:
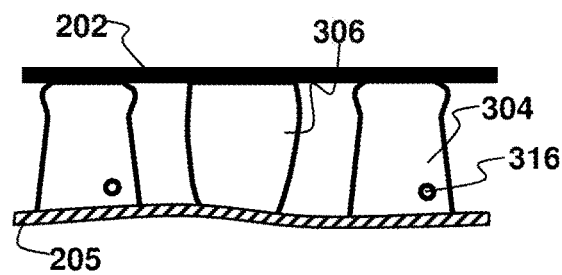
Figure 6C:
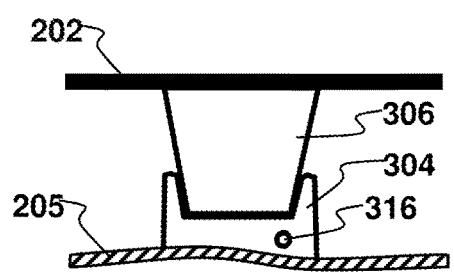

Referring to FIGS. 6A, 6B, and 6C, detailed views of elements of the alternate embodiment (300 in FIG. 5A) are shown. Among the elements from FIG. 5A that are shown in FIG. 6A, FIG. 6B, and FIG. 6C are the pad frame 205, a first elastically-resilient impression 304, a second elastically-resilient impression 306, and a shell 202. These elements (pad frame 205, first elastically-resilient impression 304, second elastically-resilient impression 306, and a shell 202) can be described as a four-layer impact reduction system. In the embodiments shown in FIGS. 6A, 6B, and 6C, the two layers with dimples 304 and 306, are in a series relationship (i.e., an aligned contact) in that the same force that passes through the first elastic impression, 304, is transmitted to the second elastic impression 306 and the total compression is the sum of the compression of the first elastic impression layer 304 and the compression of the second impression layer 306. In the embodiment shown in FIGS. 6A, 6B, and 6C the second elastic impression 306, comprises a sealed air chamber and the first elastic impression 304 comprises an orifice 316, that allows air (or any other gas or liquid) to bleed out of the impression, providing a damping or "shock absorber" feature whose resistance to compression (or tension) is velocity sensitive. Note that the sealed air chamber shown in the second impression 306, could be implemented in a variety of ways examples of which include using a permanently sealed chamber, using a bladder that can be filled or emptied as desired through a closeable valve, and/or using a closed cell foam. Note also that the elements with damping in them can have a single orifice 316, or multiple orifices, and at an extreme the damping could comprise open-cell foam. FIG. 6A shows the system in a relaxed state in which there is no force compressing the shell 202, towards the pad frame 205. FIG. 6B shows an exaggerated example what happens as a result of a high-speed acceleration of the shell 202, towards the pad frame 205, as the bulk of the deflection is taken by the sealed second elastically resilient impressions 306, because there is not enough time to bleed the air through the orifice 316, in the first elastically resilient impressions 304. FIG. 6C shows an exaggerated example of what happens as a result of a low speed acceleration of the shell 202, towards the pad frame 205, as the bulk of the deflection is taken by the unsealed first elastically resilient impressions 304, because there is time to bleed the air through the orifice 316, and the second elastically resilient impressions 306, are deformed less because the bulk of the deflection occurs as a result of air bleeding through the orifice 316, from the first elastically-resilient impressions 304.

Figure 6F:
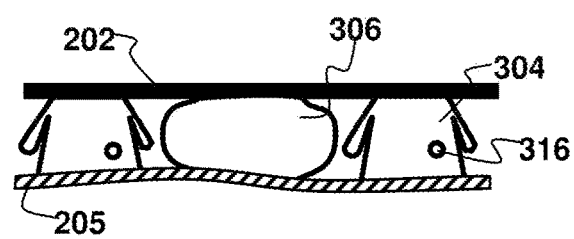

Referring to FIGS. 6D, 6E, and 6F, detailed views of elements of another embodiment of a helmet similar to the alternate embodiment 300, FIG. 5A are shown, including the pad frame 205, a first elastically-resilient impression 304, a second elastically-resilient impression 306, and a shell 202. In the embodiments shown in FIGS. 6D, 6E, and 6F, the first elastically-resilient impressions 304 and the second elastically-resilient impressions 306, are in a parallel relationship (i.e., an offset contact) in that an equivalent deflection occurs in both the first impressions 304. and the second impressions 306. and the total compressive force being transmitted is the sum of the force in the first impressions 304, and the force in the second impressions 306. In the embodiment shown in FIGS. 6D, 6E, and 6F the second impressions 306, comprise sealed air chambers and the first impressions 304, comprise orifices 316, that allow air to bleed out of these impressions, providing a damping feature. FIG. 6D shows the system in a relaxed state in which there is no force compressing the shell 202 towards the pad frame 205. FIG. 6E shows an exaggerated example what happens as a result of a high-speed acceleration shell 202 towards the pad frame 205, as the bulk of the compression is resisted by the first impressions 304, because there is not enough time to bleed the air through the orifices 316. FIG. 6F shows an exaggerated example of what happens as a result of a low speed acceleration of the shell 202, towards the pad frame 205, as the bulk of the compressive force is resisted by the sealed second impression 306, because there is time to bleed the air through the orifices 316, of the first impressions 304.

Further referring to FIG. 5A and FIG. 6A to FIG. 6F, the first elastically resilient impressions 304, and second elastically resilient impressions 306, can be designed to have different resistance to deflection in a direction perpendicular to the surfaces of the pad frame 205, and the shell 202, than their resistance to deflection parallel to the surfaces of the pad frame 205, and shell 202, whereby the rotational resistance of the helmet shown as 300, in FIG. 4 might be different than the resistance to impacts perpendicular to the shell of the helmet 300, in FIG. 5A. Note also that the force deflection characteristics can be different for different resilient impressions in the helmet 300. Thus, the helmet can comprise shock absorption elements that have force-displacement relationships that vary:
- as a function of direction;
- as a function of speed;
- as a function of position;
- as a function of location; and/or
- as a function of rotation versus translation.

Figure 7A:
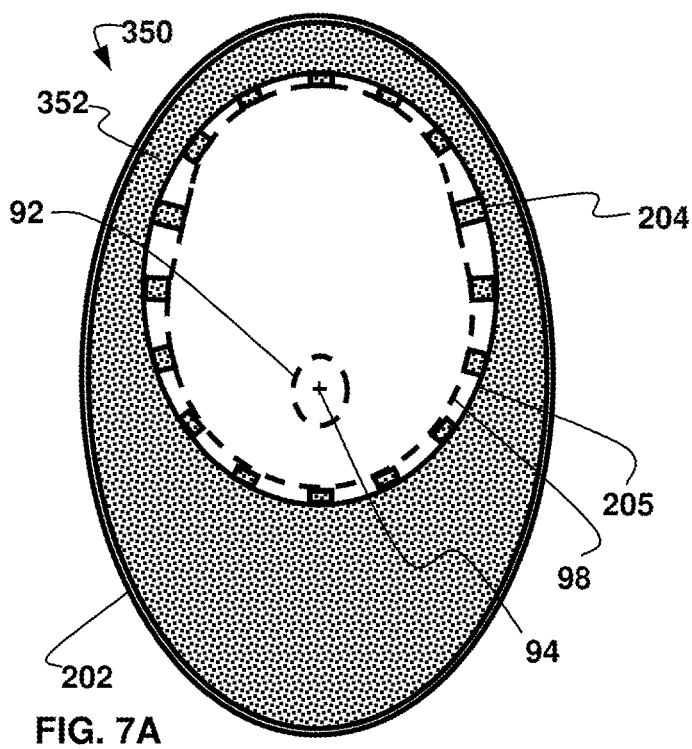
FIG. 7A shows a configuration of an embodiment of an improved helmet that incorporates a single-use impact reduction material.
Figure 7B:
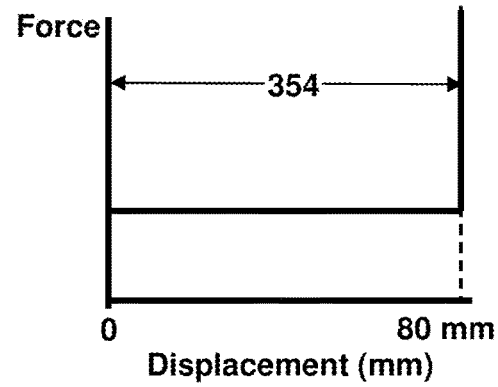
FIG. 7B is a force-displacement curve for a single-use constant force impact reduction material.

Referring to FIG. 7A yet another embodiment of an impact reduction helmet is shown at 350. More specifically, this is a single-use impact reduction helmet 350, that incorporates a single-use impact material 352. One example of a single-use impact material 352, is metal foam. The advantage of this type of a material is that after an accident the size of the impact can be directly seen from the amount of material that has been permanently deformed. FIG. 7B shows the force-displacement relationship for the single-use impact material 354. As one can see, the force is totally constant for the entire range of displacement until all of the material has been crushed. Note that this single use helmet 350, can also incorporate a change in the gap between the front of the helmet and the rear of the helmet. In this case, the oval shape of the helmet is retained to reduce wind resistance, but the center of rotation and the center of curvature have been moved back to the rotational center 94, which is the center of the upper spinal cord in the region of the foramen magnum 92.

Figure 7C:
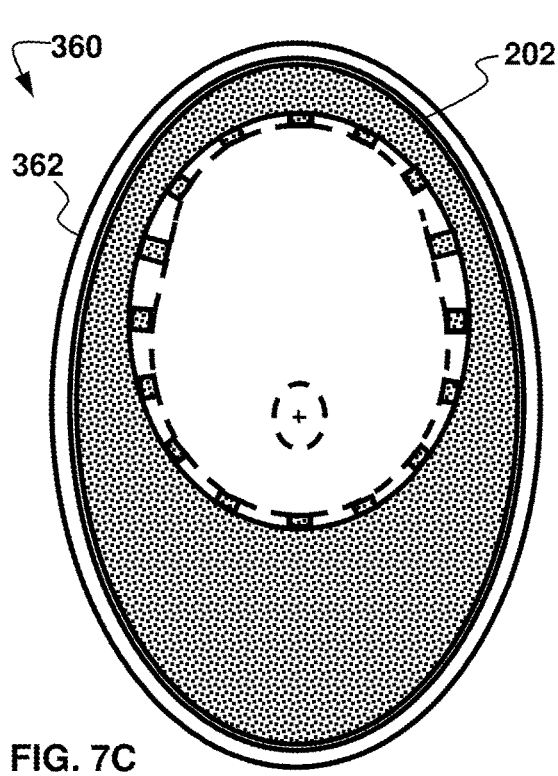
FIG. 7C is an oval helmet with a rotationally compliant cover.
Figure 7D:
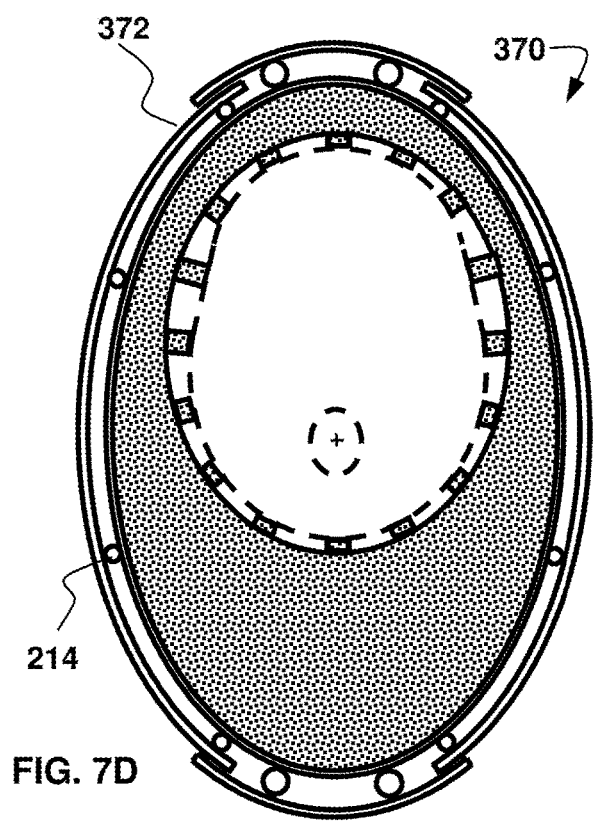
FIG. 7D is an oval helmet with a multi-element rotationally compliant cover.

Referring to FIG. 7C an oval helmet similar to that of FIG. 7A has been illustrated. The oval helmet, shown at 360, incorporates a rotationally compliant cover, shown at 362. The cover 362, that is shown could be made out of a soft material, such as a knit fabric that has a very low coefficient of friction relative to the shell 202, that is below it, making it easy to prevent tangential forces on the shell 202, from creating a load on the wearer of the helmet. Referring to FIG. 7D, it is also possible to place multiple rigid segments of elements on the outside of the helmet and allow those to be rotationally compliant as shown by the helmet 370, having rigid shell elements 372, that attach to the rest of the helmet through rotational couplers 214.

Further improvements that can be made to any of the embodiments described above can include:

1. The addition of sensors to warn of an impending collision, similar to the sensors being used on driverless vehicles. These collision-detection sensors can be used to deploy additional padding such as air bags outside of the outer shell.
2. The use of inertial sensors in the helmet. These sensors can measure impact. They can additionally record these impacts and/or transmit impact information using a wireless protocol. Transmission can be in the ultra-high frequency band, which is from 300 Mhz to 3 Ghz, the super high frequency band, which is from 3 Ghz to 30 Ghz, or the extremely high frequency band, which is from 30 Ghz to 300 Ghz. These sensed impacts can also generate alarms that can be auditory, visual, tactic, or communicated to the helmet wearer or another person at another location. The sensors may be self-adjusting based on a measurement of background noise or based on calibration to a specific user and use profile. The sensors may change an alarm in response to past history. The sensors may provide feedback to the shock absorption elements in the helmet to help tune these shock absorption elements.
3. In one embodiment, the sensors could be responsive to remote assistance that allows a remote device or person to evaluate, correct, repair, or switch from sensor to sensor. Similarly, another person (remotely) can evaluate individual sensors and use data logging and evidence-driven information to make changes to the sensors.
4. In one embodiment, the sensors may provide active streaming of the person's biometric/physiologic or biochemical information. The biometric information can include parameters such as pulse, oxygen saturation, blood pressure, change in neural activity such as an EEG, and body temperature. These biometric sensors could be located closest to the person's skin surface. Sensors further from the wearer's body can measure an impending impact, the type of impact (i.e., whether it is a projectile or a blunt object), and impact speed, and impact direction. Sensors in the helmet may also provide information about the wearer's identity. These sensors could be located on the outer shell or could be located closer to the person's body.
5. Making the shell (shown as 202, in FIG. 4A) can be made of multiple elements that have the ability to move relative to one another and have energy absorption between them. For example, a face mask (not shown) or face shield could be attached to other parts of the outer shell through an energy-absorbing coupling.
6. The shell (shown at 202 in FIG. 4A) could be specifically designed to be smooth and completely free of non-spherical obstructions, such a protrusions, ridges, or indentations. Non-spherical obstructions can make it more difficult for a helmet to "bounce" off of another helmet or other impacting device or material surface. The spherical shell could have multiple openings for ventilation, or to reduce weight. Prior art helmets typically have ridges or indentations on the shell that can be grabbed or catch on things or surfaces and increase the forces on the helmet, especially rotational forces.

It should be noted that the embodiments shown in this invention could be made of a material that aids in the effectiveness of the helmet. Such specialized materials can include: silicon carbide; boron carbide; amorphous boron; hafnium carbine; tantalum carbide; tungsten carbide; magnesium diboride; carbon nanotubes; glassy carbon; diamond-like carbon; single-crystal tungsten; boron nitride; titanium diboride; hafnium diboride; lanthanum hexaboride; cerium hexaboride; molybdenum carbide; tungsten disulfide; polyethylene; polyurethane; polyvinyl; nylon; an aramid material such as Kevlar; or any organic or inorganic material. In various embodiments, shear responsive materials may be incorporated into various components of the outer shell, pad frame, inner frame and/or liner components, including materials that stiffen and/or harden in response to impact forces such as PORON XRD urethane.

It should be noted that the embodiments shown in this invention could have sensors made of a variety of materials including nanotubes of pure carbon, graphene made of pure carbon, single electron transistors (SETs), organic molecular materials, magnetoelectronic materials (spintronics), organic or plastic electronics, or any other material capable of being understood by someone skilled in the art. Sensors can also be comprised soft mesh and flexible (of materials such as gold-coated silver nanowires mixed with a type of rubber, called polystrene-butadiene-styrene. Among electrochemical transducing elements, organic electrochemical transistors (OECTs) can be used for bioelectronics due to their exceptional ability to interface electronics with biology.

Ocular Parameter-Based Head Impact Measurement

Figure 8:
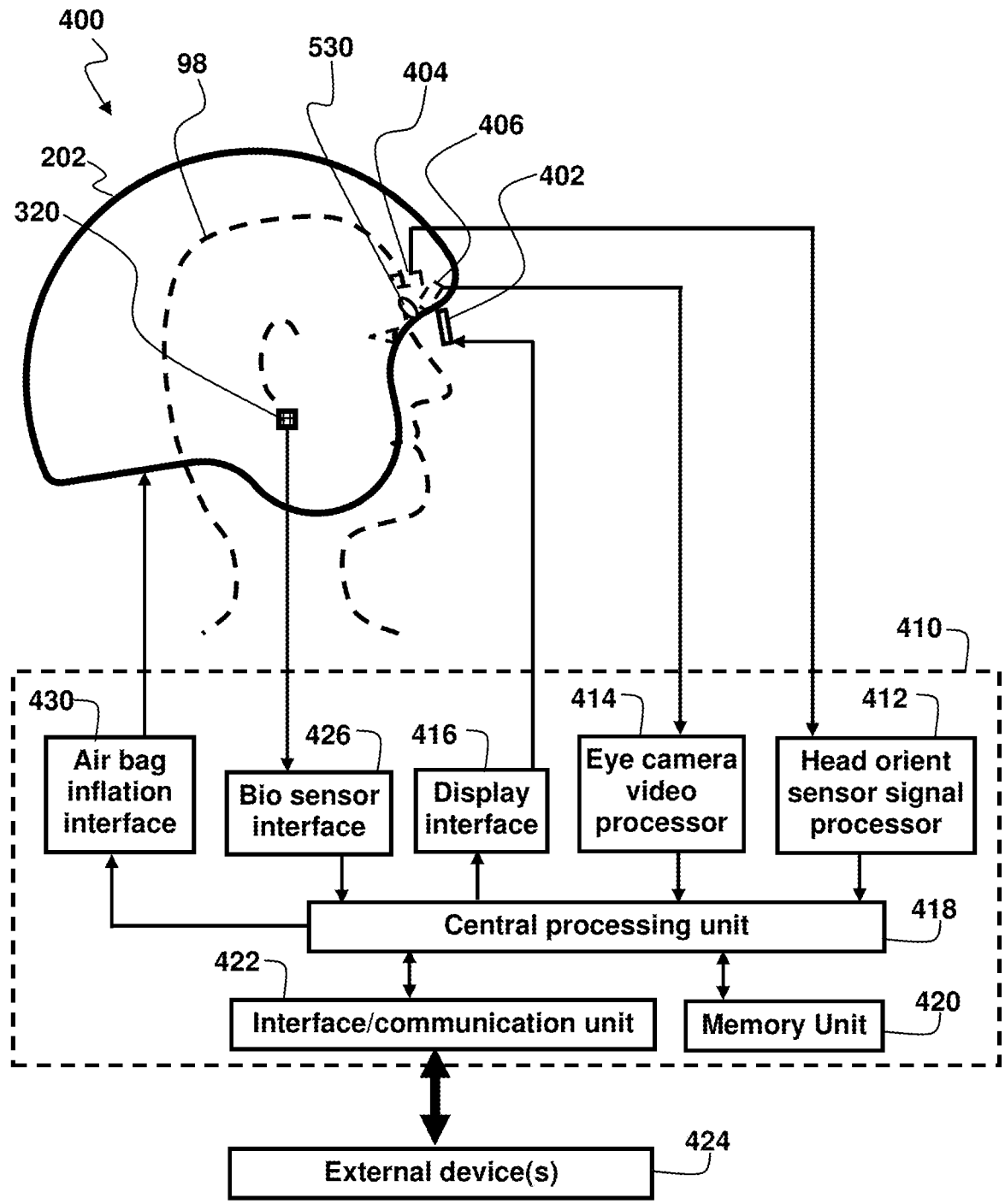
FIG. 8 shows a centered spherical helmet that comprises an ocular parameter measuring system.

Referring now to the figures that describe ocular performance-based head impact measurement, FIG. 8 shows a helmet, similar to the ones illustrated and described with reference to FIG. 3 through FIG. 7D, that further comprises an ocular performance-based measuring system. Referring in more detail to FIG. 8, the rotationally centered impact reduction helmet comprising an ocular performance measuring system 400 is shown on the head 98, of a person. The centered ocular performance measuring helmet 400, can comprise a spherical shell 202, a see-through display 402, a head orientation sensor 404, an eye measuring sensor 406, and an illumination source 530. The centered ocular performance measuring helmet 400, is designed to fit snugly on the head of the person 98 so that all changes in head orientation result in equal changes in orientation of the centered ocular performance measuring helmet 400. The head orientation sensor 404, is rigidly attached to the centered ocular performance measuring helmet 400. In at least one embodiment, the head orientation sensor 404, senses (is responsive to) pitch, roll, and/or yaw. Pitch can be described as upward or downward movement of the face. Roll can be described as rotation of the face when viewed from the front. Yaw can be described as leftward and rightward movement of the face when viewed from the front. The head orientation sensor 404, can be constructed from one or more elements or it can be monolithic. The head orientation sensor 404, can use one or more accelerometers, gyroscopes, magnetometers, or any other relative or absolute position, velocity, or acceleration sensing device capable of being understood by anyone skilled in the art. In one embodiment, the orientation sensor comprises a micro-electro-mechanical system (MEMS) integrated circuit.

Further referring to FIG. 8, in one embodiment, the eye sensor 406, is more specifically an eye tracking digital video camera that is pointed at the eyes of the person. The eye sensor 406, can be responsive to any eye position, including vertical movement of the eyes (which represents pitch), rotation of the eyes (which represents roll), and horizontal movement of eyes (which represents yaw). It can also be responsive to eyelid position. There can be one eye sensor camera 406, that monitors only one eye, one eye sensor camera 406, with a wide angle, that can monitor both eyes, or two cameras, one to monitor each eye. There can also be multiple cameras, to monitor different areas of each eye (e.g., eye response sensors tracking pupil features and corneal reflection surfaces). The eye sensor video camera 406, can be positioned anywhere around the eye, and can utilize visible or invisible light. In one embodiment, the system shown at 400 further comprises an illumination source 530 to help illuminate the eyes of the person. This illumination source 530 could project infrared light, near infrared light, or visible light in the direction of the person's eyes to help improve the sensitivity of the eye sensor 406 and make it less sensitive of other light sources, which may produce noise and/or glint.

In the embodiment shown in FIG. 8, the see-through display 402, head orientation sensor 404, and eye tracking camera 406, are connected to an electronic module 410. The electronic module 410, comprises a head orientation sensor signal pre-processor 412, that is connected to the head orientation sensor 404, an eye camera video processor 414, that is connected to an eye tracking camera (406), and a display interface 416, that is connected to the display 402. Inside the electronic module 410, the head orientation sensor signal preprocessor 412, the eye measuring camera video processor 414, and the display interface 416, are connected to a central processing unit 418. Also connected to the central processing unit 418, is a memory unit 420, and an interface and/or communications unit 422. The memory unit 420, can store multiple readings and results, which can be used for data logging, tracking of multiple users, and tracking of performance at various times. The interface and/or communications unit 422, can be connected to an external device 424. Transmission of signals between the communications unit 422, and the external device can be through a wired connection or a wireless connection using any connection method and/or protocol capable of being understood by anyone skilled in the art, including, but not limited to a serial protocol (such as USB), an ethernet protocol (such as TCP/IP), and a cellphone protocol (such as LTE). Additional elements that are not shown but might be included in the electronic module 410 can be a battery, a battery charge level indicator, and a power management module. The battery in the electronic module could be wirelessly charged. The worn device can contain a dual-purpose charging/connection port and this port could comprise a USB-C or a USB-Micro B connection. The connector on the other side of the charging cable could be a standard rectangular USB connector. The connection could be USB 3.0 or better. Communication between the electronic module 410, and the head worn unit can be through a wired connection or a wireless connection using any connection method and/or protocol including, but not limited to those described for the connection between the interface/communication unit 422, and the external device 424.

Note that the embodiment of the helmet shown at 400 in FIG. 8 could also comprise additional sensors 320 and 322, such as those described previously with reference to FIG. 5A. These additional sensors 320 and 322, could detect biometric, physiologic and/or biochemical parameters of the wearer of the helmet. The sensors could be connected to the electronic module 410, and more specifically to a bio-sensor interface 426, that communicates with the central processing unit 418, and the other parts of the system described herein.

The embodiment of the helmet shown at 400 in FIG. 8 could further comprise an airbag, such as the airbag shown at 330 in FIG. 5B. FIG. 8 does not specifically show an airbag (in order to keep this illustration simpler), but it can be understood that such an airbag would typically be located outside of the shell 202, which is shown in FIG. 8. The airbag would require an inflation interface, which is shown at 430 in FIG. 8. The inflation source is responsive to the central processing unit 418. The airbag inflation interface 430 could inflate the airbag in response to the detection of an impact by the head orientation sensor processor 412, or in response to device configured for sensing an impact before it occurs, such as a proximity detector, video camera, or information from the helmets of other players on a sports field.

Figure 9:
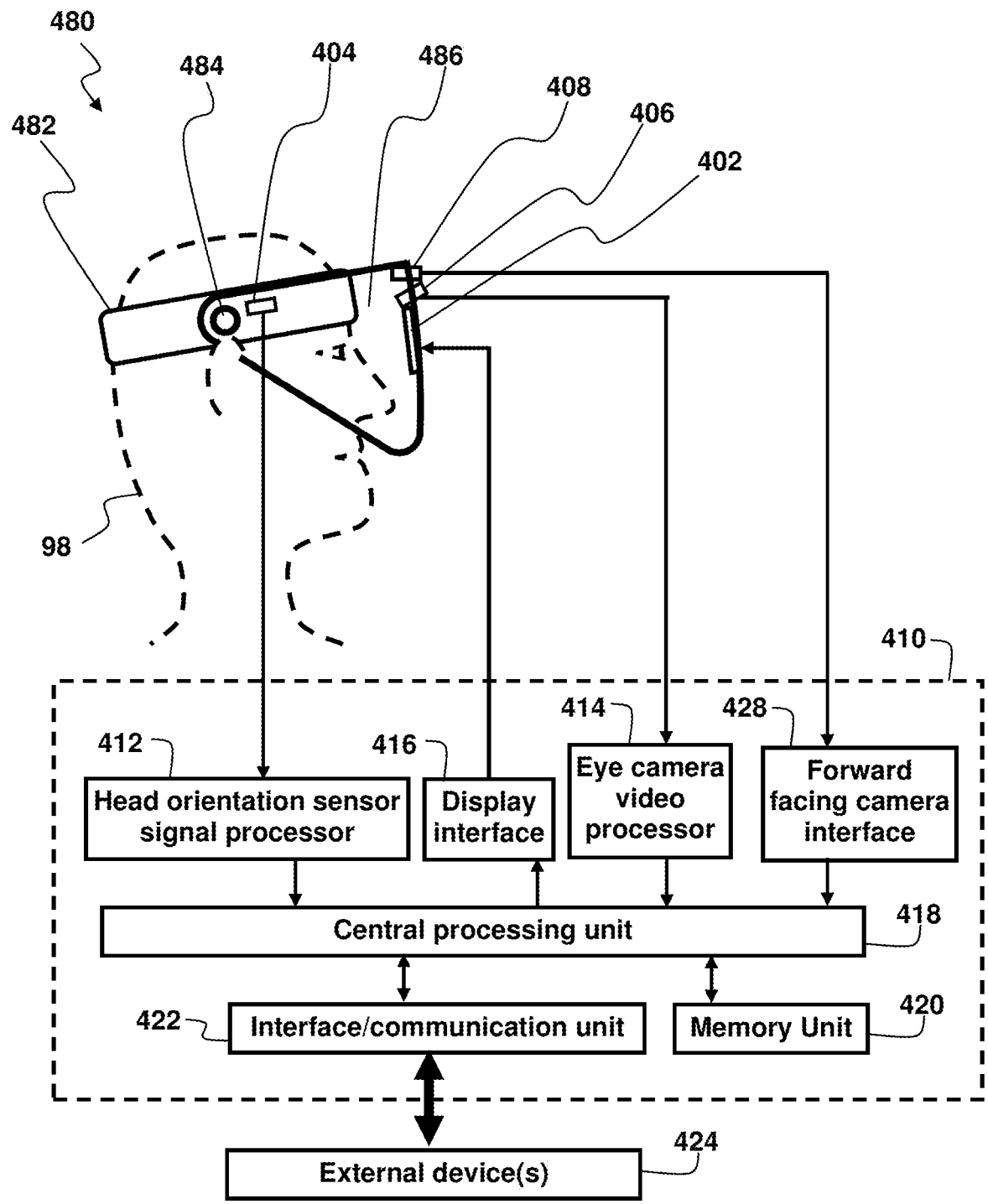
FIG. 9 shows face shield-based ocular parameter measuring system.

Features of the system and methods described herein could also be used in a face shield-based embodiment, such as the face shield system shown at 480 in FIG. 9. In this embodiment, a head attachment member for the face shield is shown at 482. The head attachment member 482 could be rigid. The head attachment member 482 can be attached to a see-through shield 486 using pivotable linkages 484 on each side of the head attachment member 482 to allow the shield 486 to be rotated up out of the line of sight. The see-through shield 486, could comprise transparent or translucent materials. The face shield system 480 can comprise eye sensing elements and/or transducers for detecting and measuring eye movements and a head orientation sensing element/transducer and circuitry to the electronic elements such as:

the head orientation sensor shown at 404, connected to the orientation sensor signal processor 412;

the eye-tracking digital video camera 406, connected to the eye camera video processor 414; and the central processing unit 418, memory unit 420, and interface/communication unit 422 for communicating with an external device 424.

The face shield-based system 480, of FIG. 9 could have other sensors (320 in FIG. 8) interfaced with the electronic module 410, in the same way as was described for the helmet-based system in FIG. 8. In another embodiment, the face shield-based system 480, could have a display 402 and display interface 416 implemented in the same way as was described for the helmet-based system of FIG. 8. The display, could be a see-through display and could be used for augmented reality. However, a display might be difficult for the person to use when active. As an alternative, the face shield-based system 480, of FIG. 9 might have a forward-facing camera 408, that communicates with a forward-facing camera interface 428, in the electronic module 410. The eye sensors 406 can be responsive to the forward-facing camera 408 to measure the ocular performance. In this case, the central processing unit 418, or the external device 424, could combine the information from the head orientation sensors 404, the eye-tracking digital video camera 406, and the forward-facing camera 408, to determine one of the ocular performance parameters described herein. The face shield-based system could also comprise an illumination source similar to the illumination source shown and described with reference to 530 in FIG. 10B. This illumination source could project infrared light, near infrared light, or visible light in the direction of the person's eyes to help improve the sensitivity of the eye sensor 406 and make it less sensitive of other light sources, which may produce noise and/or glint.

Figure 10A:
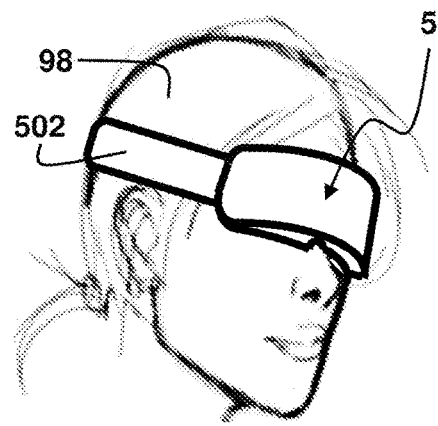
FIG. 10A shows a goggles embodiment of a head-worn virtual reality unit.
Figure 10B:
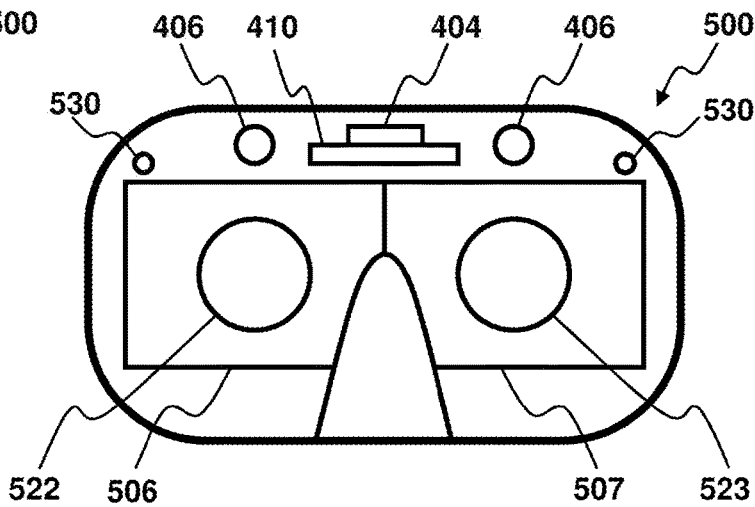
FIG. 10B shows the virtual reality unit of FIG. 10A when viewed from the inside of the goggles looking outward.

FIG. 10A and FIG. 10B show an augmented and/or virtual reality (VR) goggles embodiment of a head-worn device for measuring human ocular parameters. FIG. 10A shows the head-worn augmented, or VR device 500, attached to a person's head 98, with a strap or headband 502. In the augmented device shown in FIG. 8, the display (402) was a see-through display and it only covered one eye or part of an eye. In the AR/VR-device of FIG. 10A and FIG. 10B, shown at 500, the left virtual reality display, shown at 506 and right virtual reality display 507, are opaque and the person is typically completely immersed in the scene being displayed. Other than the difference in displays, the VR goggles embodiment in FIG. 10B, can have many of the same elements and configurations that were described with respect to FIG. 8 and FIG. 9, including but not limited to the head orientation sensor 404, the eye tracking video camera(s) 406 (of which there can be one for the left eye and one for the right eye), and the electronic module 410. In order for the person's eyes to be able to focus on the displays (506 and 507), there are typically two lenses 522 (left eye lens) and 523 (right eye lens) between the person's eyes and the displays, 506 and 507, when the VR device 500, is worn normally by the person. Because the interior of the VR device 500 is not exposed to external light, there can be one or more illumination source(s) 530, to provide light that can be used by the video camera(s) 406 to sense ocular parameters such as eye or eyelid position or eye motion or any of the other ocular parameters described in other parts of this document. The illumination source or sources 530, can use infrared, near infrared, or visible light.

Referring specifically to the left and right eye tracking digital video cameras 406 in FIG. 10B, these cameras (more generally eye sensors) can be used for more than just the tracking of eye position in response to head movement. The eye sensors 406 can also be used to perform the following functions:

(a) The eye sensors could be used to provide control information. For example, the position of one or both of the eyes (or the orientation or movement of the eyes or eyelids) could be used to determine which of a plurality of choices a user has selected in a menu of options presented on a display. This selection could be to change the scene being displayed to the user. This selection could be used to turn something on or off.

(b) The eye sensors could be used to image one or both retinas of the person, to capture anatomic features of a retina, to capture motion and/or orientation of a retina, and/or to determine retinal image stability and/or foveal fixation.

Embodiments of the present invention could also be implemented with eye trackers (also described herein as eye sensors), shown for example at 406 in FIG. 8, FIG. 9, and FIG. 10B, which are not video cameras. Examples of non-video camera eye trackers can include electromyography trackers and electromagnetic trackers. Embodiments of the present invention could also be implemented with the use of a virtual retinal display providing an image directly on the retina of the user's eye.

Figure 10C:
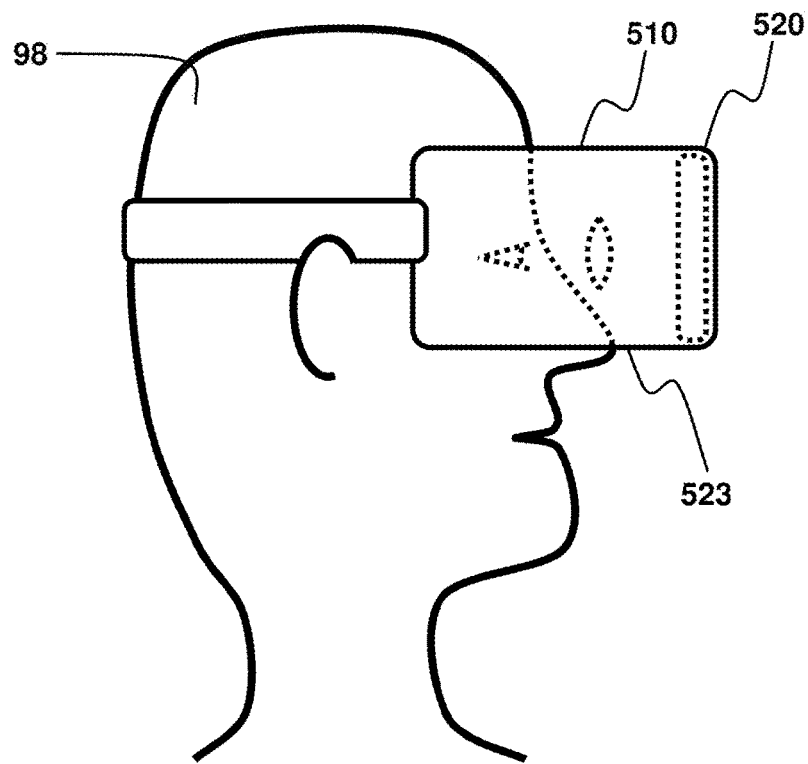
FIG. 10C shows head-worn virtual reality goggles comprising a smartphone.

FIG. 10C shows head-worn virtual reality goggles 510, comprising a smartphone 520. These goggles 510, use the smartphone 520, to provide the display, the eye tracking digital video camera, and the head tracker functionality, and doing many, or all, of the functions of the electronic module. To help the person's eyes focus on the display of the smartphone 520, these virtual reality goggles further comprise one or two lenses 522 and/or 523, that sit between the eyes of the person's head 98, and the smartphone 520. In the embodiment shown in FIG. 10C, the smartphone 520 can contain embedded software to perform all of the necessary functions of measuring all eye movements and/or ocular functions as well as measuring head movements. Alternatively, in another embodiment, the smart phone or smart device can be hand-held and the head and eye measurements for each eye discussed herein can be made from embedded software. As an example, head tracking and eye movements can be detected and measured to perform VOR testing. Instructional signals, such as when to rotate the head while looking a visual target, can be random to prevent the subject from anticipating the timing, in the form of visual cues, auditory signals or a haptic signal. Such signals could be provided through the smart phone. Calibration and other specific ocular parameters test measures can similarly be performed with the smart phone application. Data obtained can be logged and transmitted wirelessly to another smart device.

Figure 11:
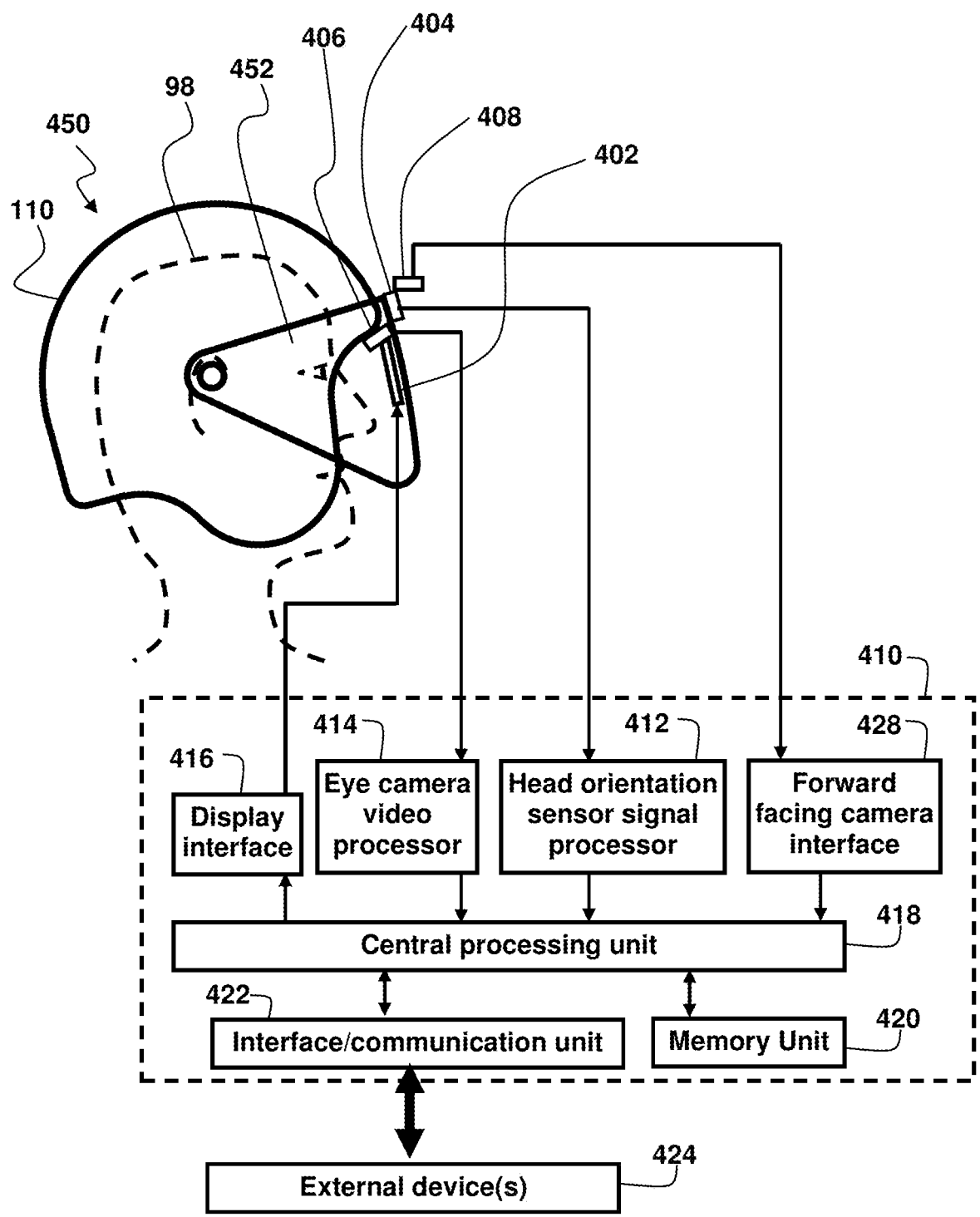
FIG. 11 shows a face shield that comprises an ocular performance measuring system.

FIG. 11 shows a face shield or visor embodiment of an ocular performance measuring system head-worn augmented reality unit 450. The face shield system 450, shown in FIG. 11 is similar to the helmet system, 400 in FIG. 8, and the face-shield system, 402 in FIG. 11 and could have any of the features and attributes of these other embodiments. The face shield system 450, could be electronically coupled to the electronic module 410, and this electronic module 410, could be part of the face shield system 450, or the electronic module 410, could be external to the face shield system 450, and communicate through a wired or wireless connection.

Figure 12A:
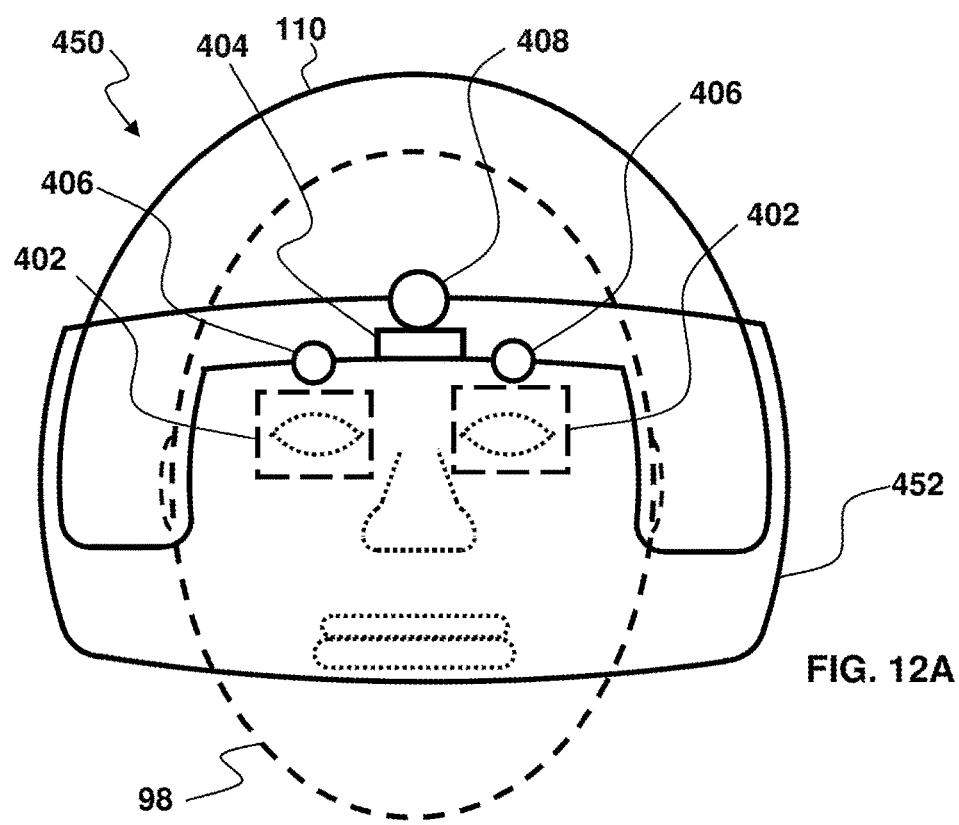
FIG. 12A shows a face shield comprising two micro light emitting diode see-through display panels.

FIG. 12A shows a front view of the face shield system 450 of FIG. 11, without the electronic module. The face shield system 450 in FIG. 11 and FIG. 12A, could be used for measurement of any human ocular performance parameter described herein. The face shield system 450 shown in FIG. 11 and FIG. 12A is configured to be worn on a person's head 98. The face shield system 450 can comprise: a see-through display 402; a head orientation sensor (head tracker) 404; an eye tracker 406, which could more specifically be an eye-tracking digital video camera; a forward-facing camera 408; a face shield or visor 452; and a helmet 110. The helmet 110 in FIG. 11 and FIG. 12A could be a prior art helmet (such as 100 in FIG. 2A and FIG. 2D). The helmet 110 in FIG. 11 and FIG. 12A could be a helmet of the embodiments shown at 200 in FIG. 3 and FIG. 4A, 300 in FIG. 5A and FIG. 5C, 350 in FIG. 7A, 360 in FIG. 7C, and/or 370 in FIG. 7D. The helmet 110 in FIG. 11 and FIG. 12A could be any other helmet (hard or soft) capable of being understood by anyone skilled in the art.

The electronic module 410 shown in FIG. 11 can comprise a display interface 416, an eye camera video processor 414, a head orientation signal processor 412, a forward-facing camera 428, a central processing unit 418, a memory unit 420, and an interface and/or communication unit 422 as shown and configured in FIG. 11. The electronic module 410 can be configured to communicate with an external device (or devices) 424 using any of the methods and systems described herein.

Figure 12B:
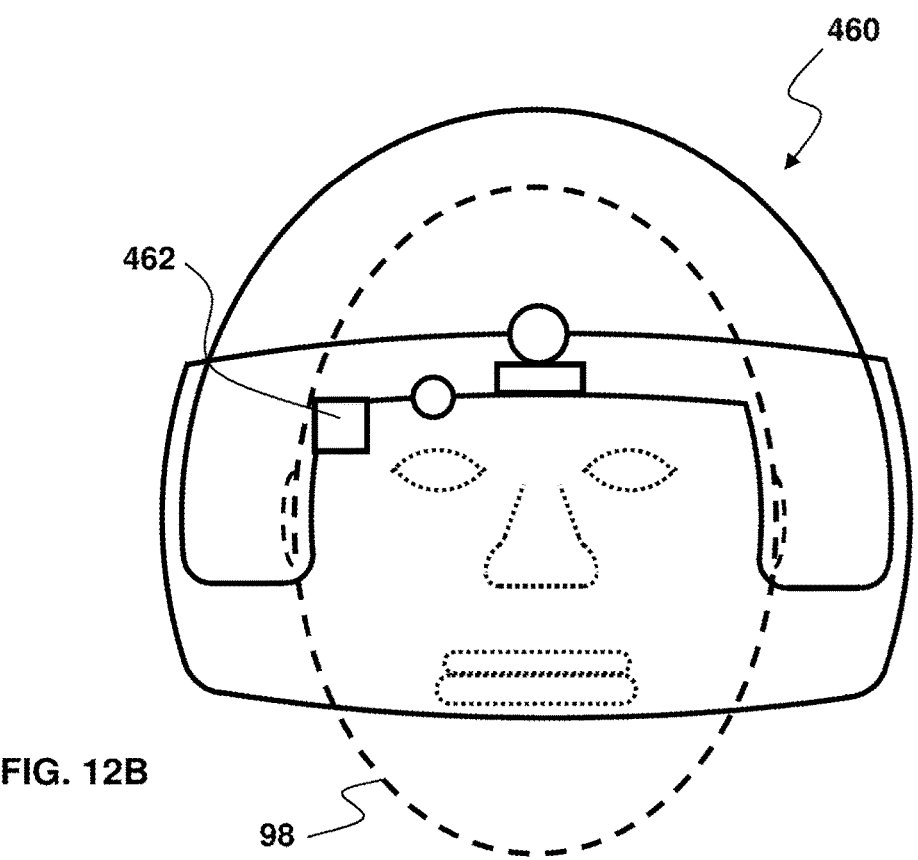
FIG. 12B shows a face shield comprising an augmented reality see-through prism.

FIG. 12B shows an alternate embodiment of the system shown in FIG. 11 and FIG. 12A. This alternate embodiment could more specifically be called a face shield based augmented peripheral vision ocular performance measuring system 460. The augmented peripheral vision system 460 in FIG. 12B differs from the see-through-display-based system 450 in FIG. 12A by having a peripheral vision display element 462 in FIG. 12B instead of the see-through display (or augmented reality display) 402 in FIG. 12A. The peripheral vision display element 462 can be implemented in any way capable of being understood by anyone skilled in the art, including the use of any optical elements described in U.S. Pat. No. 9,075,249 (Google Glass). The advantage of a peripheral vision display element 462 is that, because it is in a person's peripheral vision, the display element does not need to be see-through.

It is possible to have other embodiments of ocular performance-based head impact measurement systems and methods that use some of the elements shown in FIG. 11, FIG. 12A, and FIG. 12B. An example of such an alternate embodiment would be an ocular performance-based head impact measurement system (or method) that uses a virtual retinal display, as described in U.S. Pat. No. 5,659,327, instead of the see-through display (402 in FIG. 11 and FIG. 12A) or the peripheral vision display element (462 in FIG. 12B). Such an alternate embodiment could further include having an augmented reality display or displays in any configuration capable of being understood by anyone skilled in the art, such as the augmented reality virtual retinal displays described in U.S. Patent Application Publications 2015/0016777 and 2018/0160956 (Magic Leap).

Figure 13A:
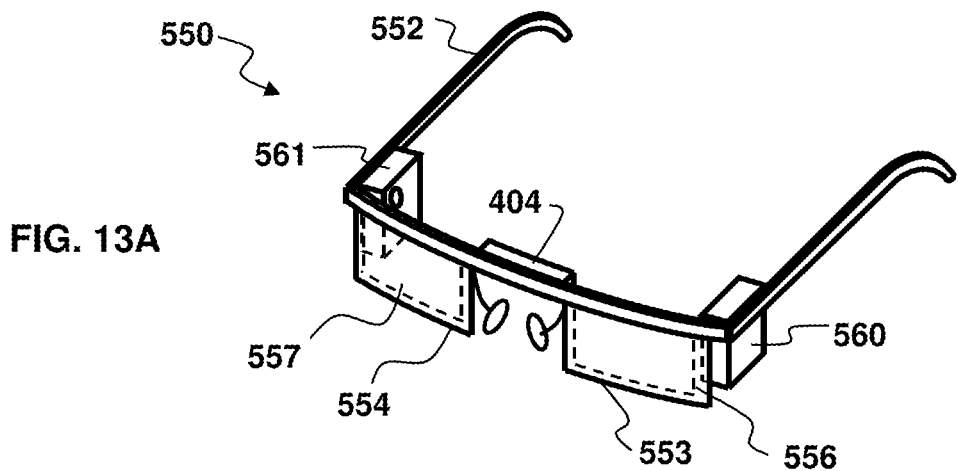
FIG. 13A shows an eyeglasses embodiment of a head-worn augmented reality unit.

FIG. 13A shows an eyeglasses embodiment of a head-worn device for measuring human ocular performance 550. The eyeglasses unit 550, shown in FIG. 13A is similar to the helmet-based unit 400. shown in FIG. 8, the goggles-based unit in FIG. 10B, and the face shield unit 450 in FIG. 11 and could have any of the features and attributes described and shown with these other embodiments. The eyeglasses unit 550 in FIG. 13A, could be electronically coupled to an electronic module 410, and this electronic module 410 could be part of the eyeglasses unit 550, or the electronic module 410, could be external to the eyeglasses unit 550, and communicate through a wired or wireless connection. The eyeglasses unit 550, could be used for measurement of any human ocular performance parameter. The eyeglasses unit 550, comprises a spectacles frame 552, which is attaches the eyeglasses unit 550 to a person's head. The eyeglasses unit 550 also comprises a left eyeglass 553, and a right eyeglass 554. The left and/or right eyeglasses could be lenses, they could be clear windows, or they could be translucent windows. Also shown are a left display 556, and a right display 557. In the embodiment shown in FIG. 13A, the displays, 556, and 557, are see-through displays that are located between the left and right eyeglass, 553, and 554, and the eyes of the person. When the displays, 556, and 557, are in this location, it is not as obvious to an outsider that the unit 550 is a head-worn system for measuring ocular performance. The displays, 556, and 557, could also be external to the left and right eyeglasses 553, and 554. In another embodiment, the displays, 556, and 557, could be located within the eyeglass unit, 554, and 555. There could be only one display, 556, or 557. The display could be off-bore and only visible in a person's peripheral vision, such as the embodiments shown in U.S. Pat. No. 9,075,249.

Further referring to FIG. 13A, the eyeglasses unit also comprises a head orientation sensor located in the bridge 404, a left eye tracking digital video camera 560, and a right eye tracking digital video camera 561. All of these components can be connected similarly and, in any configuration, and combination to other embodiments described herein. The embodiments shown in FIG. 8, FIG. 11, FIG. 12A, FIG. 12B, and FIG. 13A can be considered augmented reality implementations. In these augmented reality units, the display could be see-through or opaque. If it is opaque, it could cover part or all of the field of view. If it is see-through or opaque and covers only part of the field of view, it could be in one eye or both eyes. If it is opaque and covers the entire field of view, it can only be in one eye. The augmented reality display(s) in these embodiments can provide an image of interest or a target for the user to focus on. This image of interest (or target) could be a circular object, such as a pool ball. This image of interest or target could be static (not moving) in the field or view or it could be dynamic (i.e., moving in the field of view).

Figure 13B:
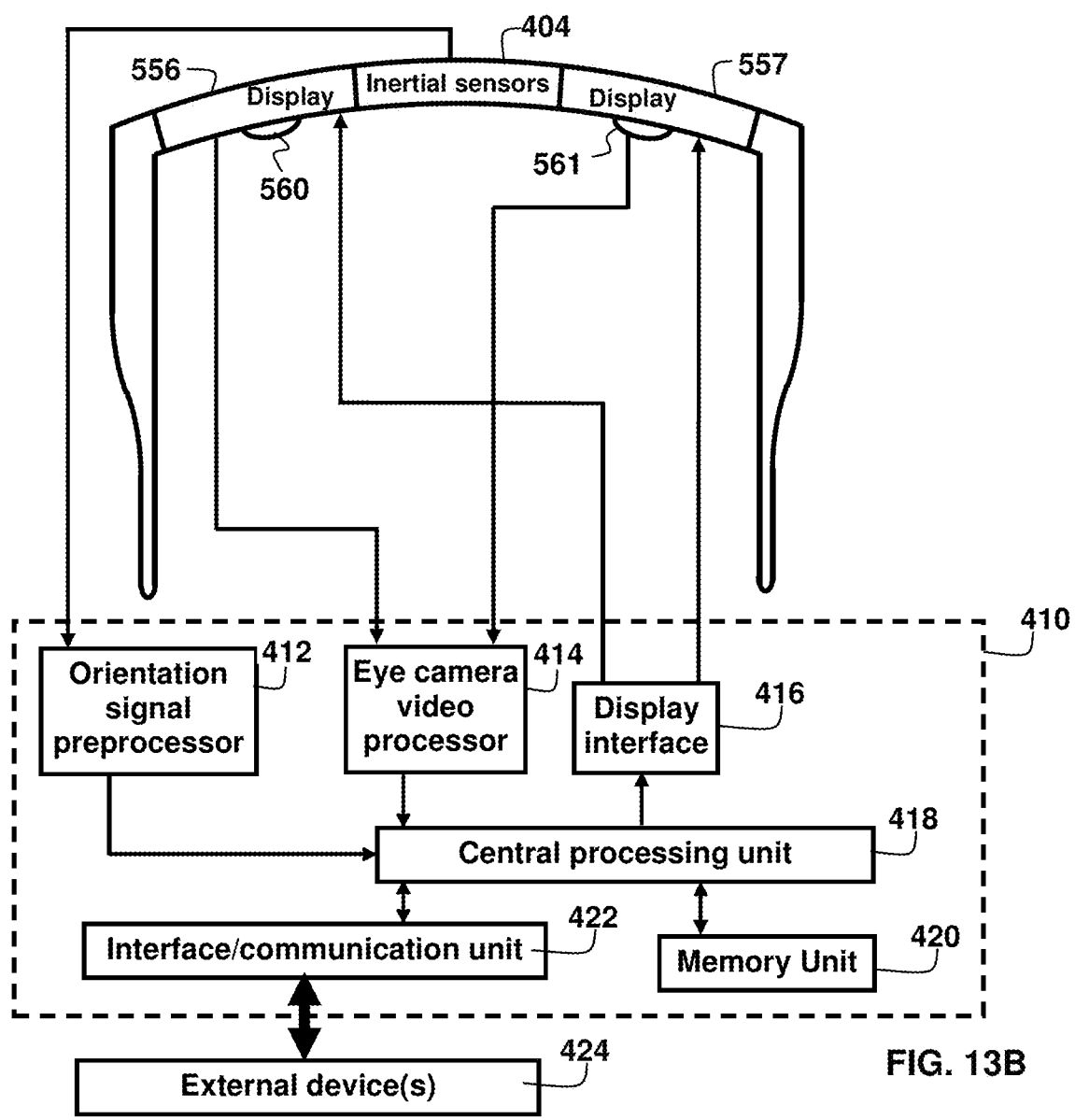
FIG. 13B shows a top view of an augmented reality or virtual reality system.

FIG. 13B shows a top view of an augmented reality or virtual reality system that also includes the main elements that were shown in the systems of FIG. 10A to FIG. 13A, including a head orientation sensor 404, a left display 556, a right display 557, a left eye tracking digital video camera 560, a right eye tracking digital video camera 561, an electronic module 410, an orientation signal processor 412, an eye camera video processor 414, a display interface 416, a central processing unit 418, a memory unit 420, an interface/communication unit 422, and an external device 424. An alternate embodiment can include a forward-facing camera 408, like that previously described in FIG. 9, that communicates with a forward-facing camera interface 428, in the electronic module 410. The forward-facing camera 408, can be responsive to the eye sensors to measure the ocular performance.

It should be noted that the AR and VR embodiments of the inventions disclosed herein can also be implemented using computer-generated 3-dimensional synthetic information instead of the monoscopic or stereoscopic "reality" information used for the augmented reality (AR) and virtual reality embodiments discussed herein.

Figure 14:
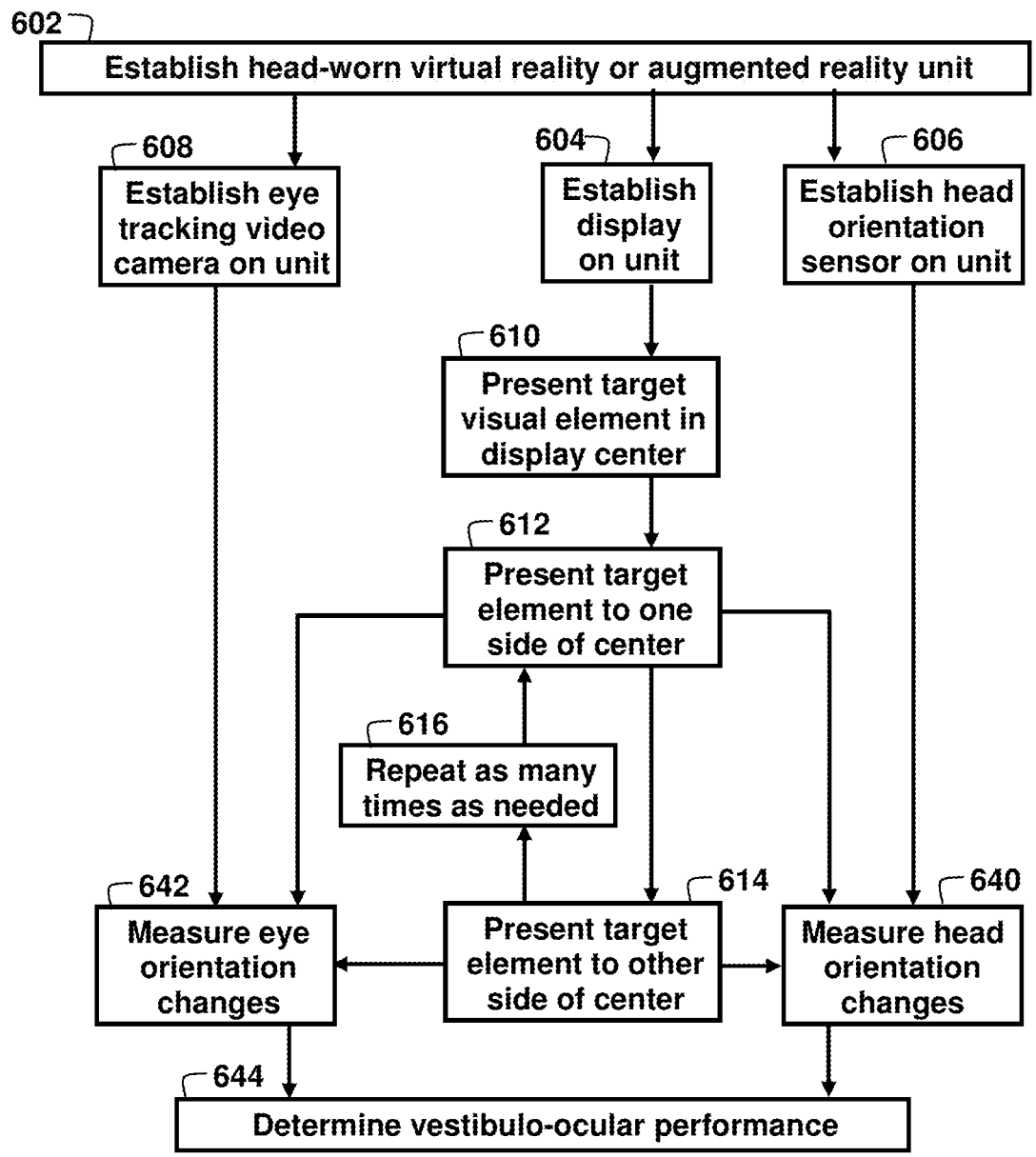
FIG. 14 shows an ocular performance calibration test method.

FIG. 14 shows an example of a vestibulo-ocular performance calibration test that can be implemented using a head-worn AR/VR unit. This test comprises the following configuration and steps:

The AR/VR unit 602, comprises a display 604, a head orientation sensor 606, and an eye tracking video camera 608.

Head: In this test, the subject is asked to keep his/her head motionless or the head is constrained to keep it motionless. The head orientation sensor 606, is used to verify that the head is stationary.

Eyes: The subject is asked to track a visual target element of interest by moving his/her eyes. The eye sensor (typically a video camera) measures the subject's eye movement 642, as visual elements are displayed.

Display: The display background is subdued, plain, solid, and/or non-distracting. In this test, the display background is similar to the background that has been used in prior art VOR testing in which the subject is asked to look at a solid colored wall which has a bright white circular dot (the target visual element of interest) projected on it. In the AR/VR embodiment of this test, the display background on the head-worn device is similar to the wall of the prior art test. The display also presents a target visual element of interest that can be similar the projected white circular dot of the prior art clinical test or it can be visually enhanced for better image or target eye fixation. The target visual element of interest then behaves in the following way:
1. The target visual element is initially displayed centrally 610.
2. It is then displayed off center on a first side (left or right) of the display center as the central image is dimmed, as shown at 612. This is typically about 20-25 degrees off center.
3. It is then displayed off center on the opposite (or second) side of the display center as the previous image to the first side is dimmed, as shown at 614. This is also typically about 20-25 degrees off center.
4. This process of dimming or removing the target visual element of interest on one side and displaying it on the opposite side is repeated as many times as needed, as shown at 616.
5. This test can be conducted in the vertical, as well as the horizontal direction.

Processor: The processor in the AR/VR system then compares eye movement to timing and appearance/disappearance of visual elements on display, and the location of these visual elements to determine vestibulo-ocular performance 644. Performance could be measured as accuracy, gain, phase, symmetry, velocity, saccades, and/or visual acuity.

Figure 15:
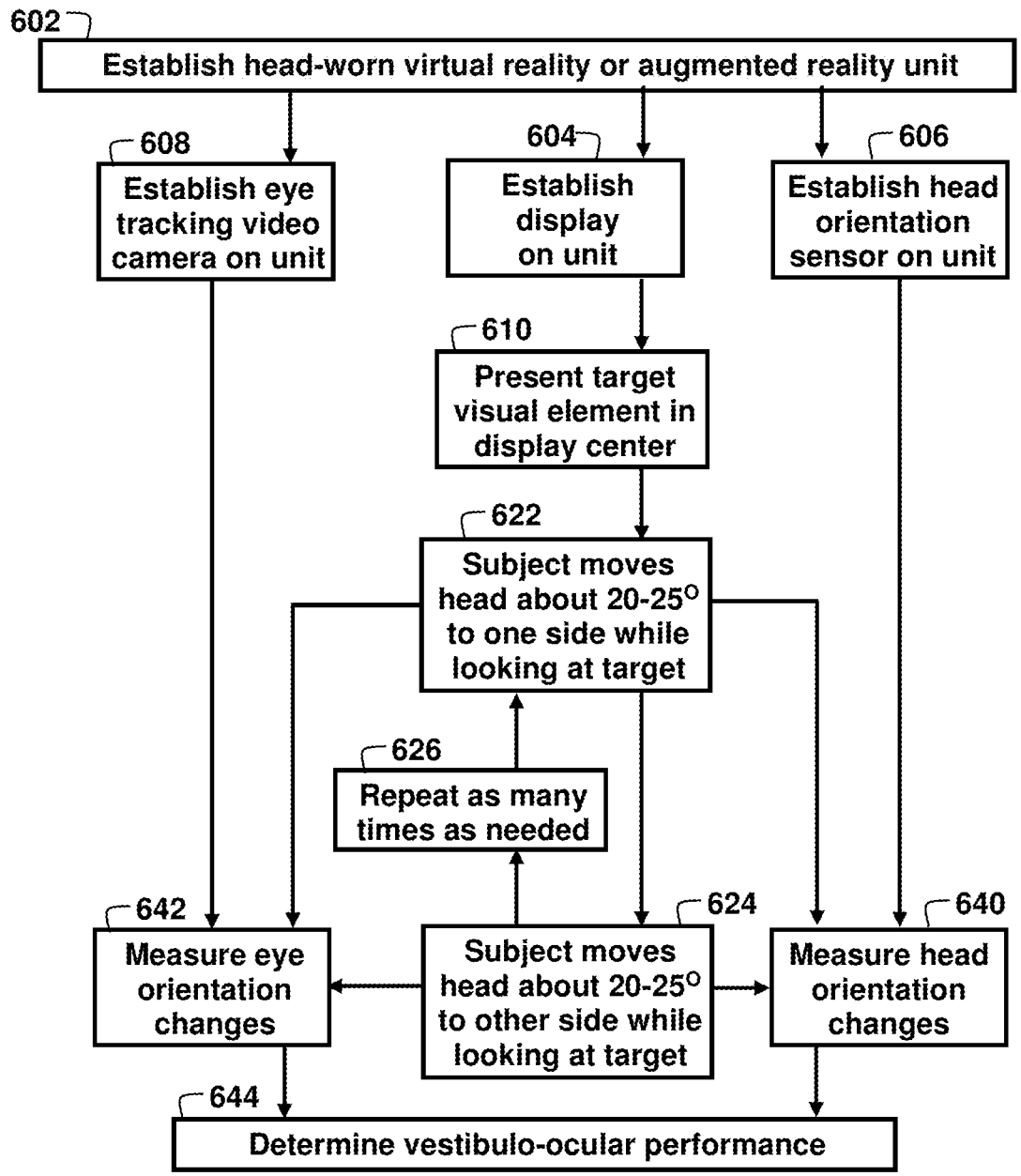
FIG. 15 shows a static active ocular performance test method.

FIG. 15 shows an example of static active vestibulo-ocular performance testing that can be implemented in a head-worn AR or VR unit. This test comprises the following configuration and steps:

The head-worn AR/VR unit 602 comprises a display 604, a head orientation sensor 606, and an eye tracking video camera 608.

Display: In this test, the display is static—neither the background nor the target visual element of interest moves or changes in any way. The display comprises a subdued background and a centered white circular dot or visually enhanced target element 610, similar to what was described with reference to the test shown in FIG. 14.

Head: In this test, the subject is asked to actively move his/her head each time he/she is given a cue signal. The head should typically move about 20-25 degrees off center about a vertical axis (i.e., left or right). The head orientation sensor measures changes in head pitch, roll, and/or yaw 640.

Eyes: The subject is instructed to keep his/her eyes focused on the target visual element as the head moves. The eye sensor (typically a video camera) measures eye movement 642, relative to head movement 640.

Cues are provided to tell the subject when to move the head. These cues can be audio cues. The cues could be haptic (i.e., vibration on the side of the person's head). The cues could be visual (i.e., change of color or intensity of the visual target element of interest). The cues are typically timed randomly so the subject doesn't try to anticipate the timing.

The test sequence is as follows:
1. The subject is instructed to move the head about 20-25 degrees in one direction when a first cue is given, and to hold the head in this new position 622.
2. The subject is instructed to move the head back about 20-25 degrees when the second cue is given 624.
3. The subject is instructed to move the head in the first direction a second time when the third cue is given.
4. The process is repeated as many times as needed 626.
5. This test can be conducted in the vertical, as well as the horizontal direction.

Processor: The processor in the AR/VR system then compares eye movement to timing and appearance/disappearance of visual elements on display, and the location of these visual elements to determine vestibulo-ocular performance 644. Performance could be measured as accuracy, gain, phase, symmetry, velocity, saccades, and/or dynamic visual acuity.

Figure 16:
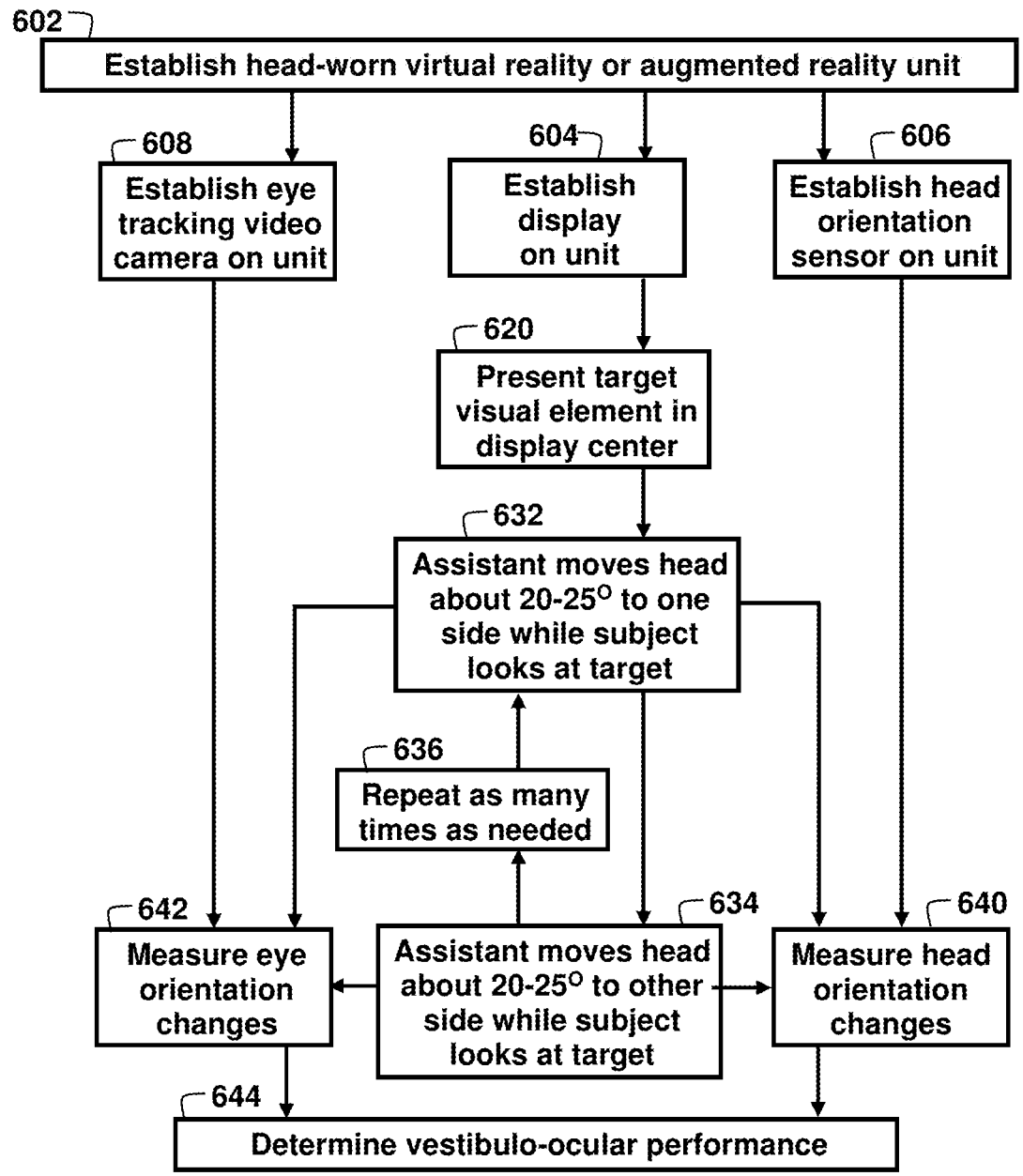
FIG. 16 shows a static passive ocular performance test method.

FIG. 16 shows a static passive vestibulo-ocular performance test that can be implemented in a head-worn AR or VR unit. This test comprises the following configuration and steps:

The head-worn AR/VR unit 602, comprises a display 604, a head orientation sensor 606, and an eye tracking video camera 608.

Display: In this test, the display is the same as for the test described with reference to FIG. 14 and FIG. 15, with a target visual element presented in the center 610.

Head: In this test, the assistant holds the subject's head and moves it about 20-25 degrees each time 632. The head orientation sensor measures changes in head pitch, roll, and/or yaw 640.

Eyes: The subject is instructed to keep his/her eyes focused on the target visual element as the head moves. The eye sensor (typically a video camera) measures eye movement relative to head movement 642.

The test sequence is as follows:
1. The assistant moves the subject's head about 20-25 degrees in one direction and then holds it in this new position 632.
2. The assistant then moves the head back in the opposite direction, 20-25 degrees and holds it 634.
3. The assistant moves the head in the first direction a second time.
4. The process is repeated as many times as needed 636.
5. This test can be conducted in the vertical, as well as the horizontal direction.

Processor: The processor in the AR/VR system then compares head movement and eye movement to determine vestibulo-ocular performance 644. Performance could be measured as accuracy, gain, phase, symmetry, velocity, saccades, and/or dynamic visual acuity.

There can be many additional embodiments of the ocular performance tests described with reference to FIG. 14, FIG. 15, and FIG. 16. Some of these embodiments can include combinations of the variations listed here:

a. The visual target element (an example of which would be a white dot or a visually enhanced target element) can be any other shape, size, or coloring or have any other features capable of being understood by anyone skilled in the art. Examples of these variations in the target visual element could include:
   A different shape (such as a shape comprising a cross hair);
   Different contrast, either more or less;
   Different intensity;
   Different size;
   Different focus, either more in-focus or out of focus;
   Having one or more features in the visual element that move relative to the rest of the visual element;
   Different depths;
   The appearance of a natural object (such as a baseball, a basketball, or a bird); and/or;
   Any combination of any of the above.

b. The test shown in FIG. 15 and/or FIG. 16 could be run with the target visual element not being stationary. This would make the overall test more similar to a natural environment in which the head, the eyes, and the visual world are all moving relative to one another and relative to a stationary reference frame at all times. When implemented on a display in an AR/VR environment, this would mean that the target visual element could:
   Move with the head movement;
   Move contrary to the head movement;
   Move perpendicular to head movement; and/or
   Move in any random pattern not associated with head movement c. The background (traditionally subdued, plain, solid, and/or non-distracting) could be presented on the display of the AR/VR system as any other background understood by anyone skilled in the art. Examples of variations of the background can include embodiments in which the background is more natural and similar to actual scene and/or any of the variations in the following list:
   The background can be completely static;
   The background can have moving and/or flashing elements;
   The background can be enhanced with auditory distractions consistent with the imagery being displayed;
   The background can be in or out of focus;
   The background can be low intensity/contrast or high intensity/contrast relative to target of interest;
   The object of interest or image can utilize foveated rendering, in which only the target of interest which the user is visualizing is seen clearly, where the fovea is focused, and the remainder of the adjacent region is less detailed.

Visual acuity, visual fixation ability, DVA (dynamic visual acuity) and FVS (foveal visual stability) can be tested using a system and method similar to the vestibulo-ocular parameter (VOP) test shown in FIG. 15 and/or FIG. 16. The following are the main elements of a DVA or FVS test performed in this way using a VR or AR environment:

Step 1. Perform a routine vision test by presenting a Snellen chart, or something similar, using the display of the AR/VR unit. This is needed to establish a baseline visual acuity in a static environment. This static test does not necessarily need to be done with a Snellen chart (the standard chart used by optometrists and ophthalmologists), it could also be done by asking the subject to identify characters of various sizes, positions, and/or locations.

Step 2. The subject is presented a visual element (such as a number or letter) in the display center in a manner similar to step 610 of FIG. 15, but in the case of a DVA or FVS test, the target visual element also comprises a character that the subject must identify.

Step 3. The size and character of the target visual element in the display center changes at random times while the subject is performing the steps described at 622, and 624, in FIG. 15 and/or 632 and 634 in FIG. 16.

Step 4. The subject speaks out the character observed each time it changes.

A VR/AR environment can also be used for positional testing. For example, VR AR goggles can be configured to display a background that has illumination, but no definable image that might provide orientation information to the subject. The subject, could then be asked to turn the head left, right, lie supine, while supine head turns right, head turns left, then turn the body (roll) right and turn the body (roll) left. During each positional change, the eyes are tracked using the AR/VR system to look for abnormal eye movements. If a target visual element was visible during this testing the nystagmus would be suppressed. However, elements with poor contrast can be displayed to provide a more immersive test environment. Visual elements in this instance should not have defining characteristics that might enable eye fixation.

A subject can be tested for BPPV using the method shown in FIG. 16 with the assistant moving the head in a specific pattern that allows the individual semicircular canals to be tested. Note that this means the head is not moved the 20 degrees side-to-side, but is instead moved based on standard protocol for the specific semicircular canal being tested.

Figure 17A:
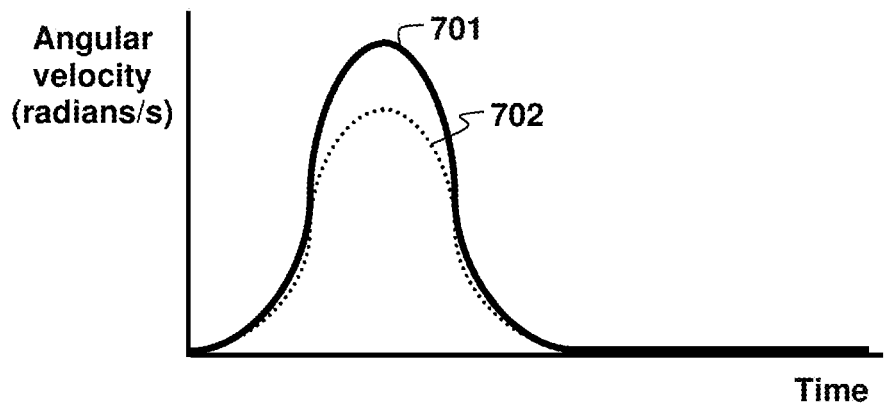
FIG. 17A shows a vestibulo-ocular gain measurement.
Figure 17B:
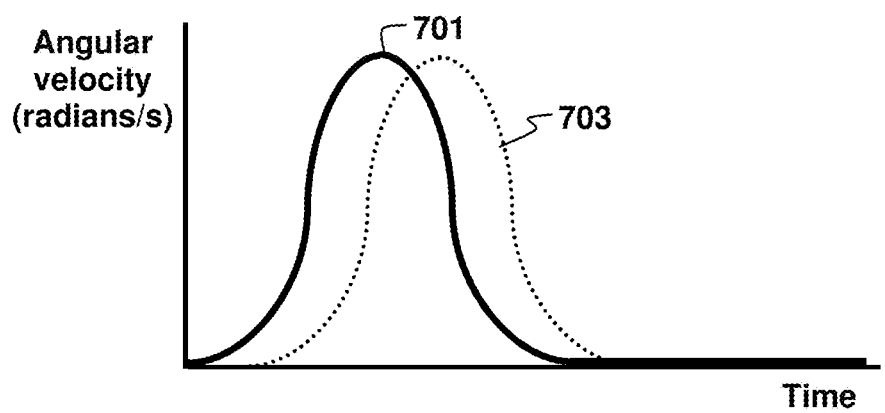
FIG. 17B shows a vestibulo-ocular phase measurement.
Figure 17C:
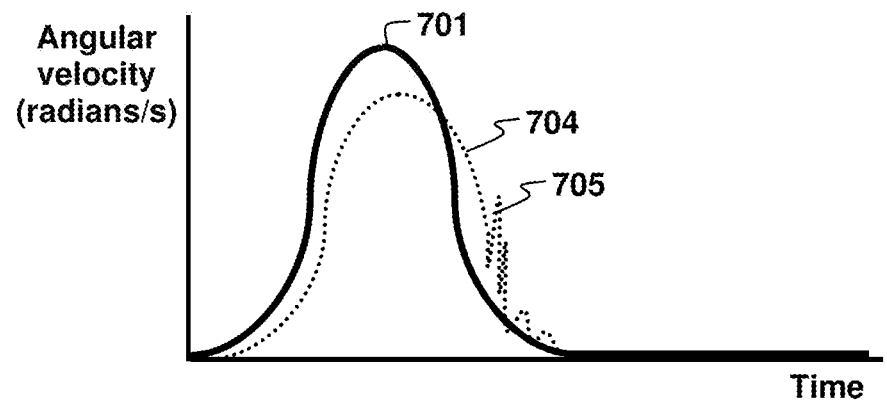
FIG. 17C shows ocular saccades.

FIG. 17A, FIG. 17B, and FIG. 17C provide graphs of time versus angular velocity that show how ocular response to a vestibular input can be measured. In these figures, the input is a rotation of the head, which is shown as the solid line at 701. This head rotation information would typically be measured using the head orientation sensor 404, that has been shown in FIG. 8, FIG. 9, FIG. 10B, FIG. 11, FIG. 12A, and FIG. 13B. The output is the eye response to the head rotation, which is shown as the dotted line at 702, 703, and 704, and would typically be measured using the eye sensor, which is typically an eye tracking digital video camera 406, such as that shown in FIG. 8, FIG. 9, FIG. 10B, and FIG. 11. The actual eye response is in the direction opposite of the head rotation, 701, but it has been plotted in the same direction to make it easier to compare the input and output of a person's vestibulo-ocular system. In FIG. 17A, the velocity of the eyes is slower than that of the head, which results in a gain of less than 1.0 (i.e., a loss of amplitude 702). In FIG. 17B there is a delay between the rotation of the head and the rotation of the eyes, which results in a phase lag, 703. In FIG. 17C, the eye rotation also lags the head rotation as shown at 704, but is caught up by saccades 705 near the end of the rotation.

Figure 18A:
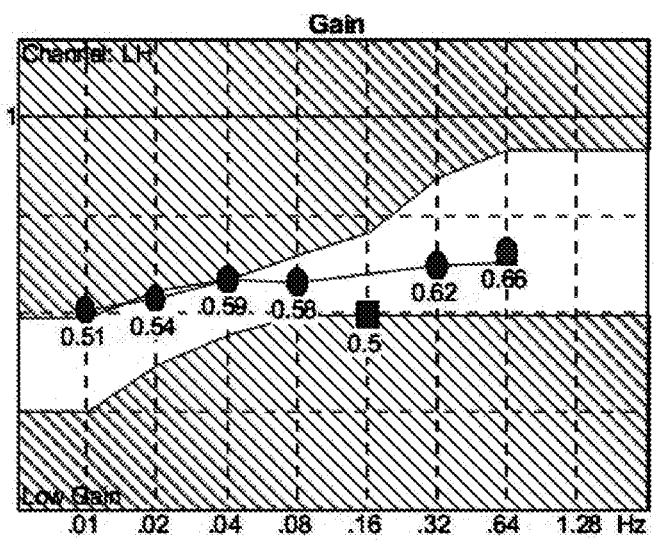
FIG. 18A illustrates an example of the left eye gain of a healthy person's vestibulo-ocular response to motion between 0.1 Hertz and 1.28 Hertz.
Figure 18B:
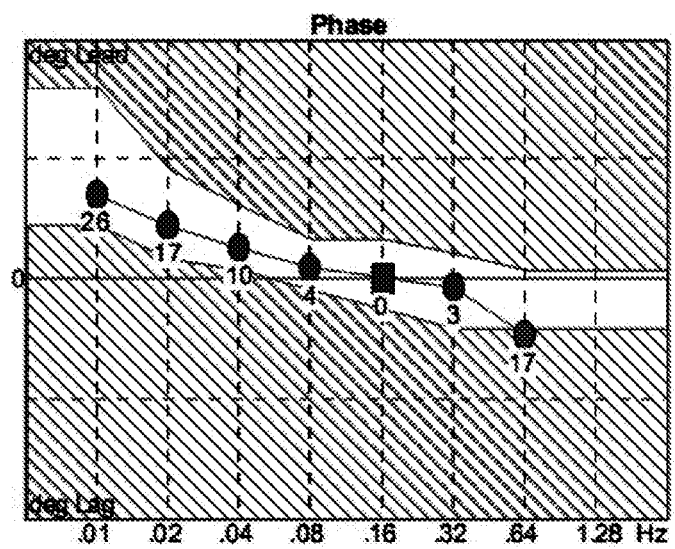
FIG. 18B illustrates an example of the phase lead and lag for a health healthy person's vestibulo-ocular response to motion between 0.1 Hertz and 1.28 Hertz.
Figure 18C:
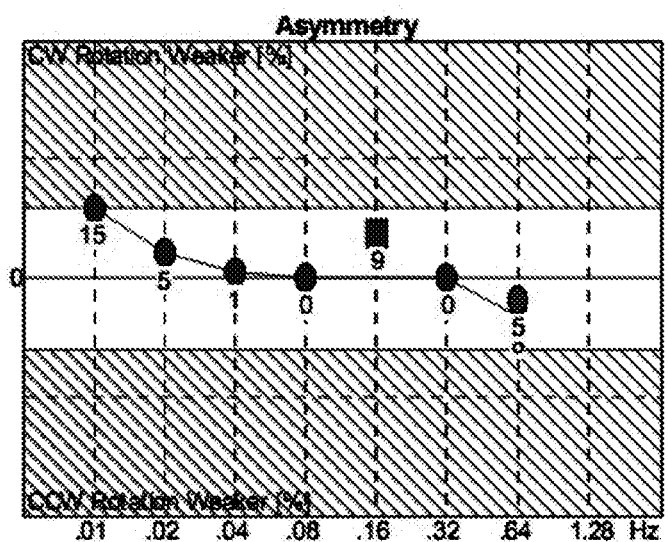
FIG. 18C illustrates an example of the asymmetry readings between counterclockwise and clockwise horizontal rotation of a healthy person's vestibulo-ocular response to motion between 0.1 Hertz and 1.28 Hertz.

The measures shown in FIG. 17A, FIG. 17B, and FIG. 17C, can be plotted at different frequencies and compared between the left eye and the right eye to create the plots shown in FIG. 18A, FIG. 18B, and FIG. 18C, which illustrate some typical eye responses to oscillation of a healthy person's head (e.g., vestibulo-ocular responses) in a horizontal plane at frequencies ranging from 0.1 Hertz (1 cycle every 10 seconds) to 1.28 Hertz (approximately 5 cycles every 4 seconds). More specifically, FIG. 18A shows the gain at these frequencies, FIG. 18B shows the phase lead and lag at these frequencies, and FIG. 18C shows the relative symmetry (or asymmetry) between clockwise and counter-clockwise oscillations. It should be noted that 0.1 Hertz to 1.28 Hertz is typical for the range of frequencies being used by prior art VOR testing systems. The embodiments described in this disclosure can include any frequency in the range of 0.01 Hertz (1 cycle every 100 seconds) to 15 Hertz (approximately 15 cycles every second).

FIG. 19A, FIG. 19B, FIG. 20, FIG. 21, FIG. 22, and FIG. 23 relate to targets or visual elements that could be projected without the use of VR or AR displays or presented on an a VR or AR display to facilitate measurement and/or improve ocular performance parameters such as vestibulo-ocular reflex function, visual pursuit, vergence, DVA, or other ocular parameters discussed herein. These targets or visual elements can be designed to enhance the eye fixation on the displayed image when the head is motionless and the visual element is in motion. These targets or visual elements could also be designed for when the head is in motion and the visual element is motionless or when both the head and the visual element are in motion. In embodiments of the invention, projection of visual elements without the use of VR or AR displays or when using either VR or AR display systems, the displayed targets or visual elements can be static in a position or location or the displayed targets or visual elements can be dynamically changing in position, depending on the specific test being performed or rehabilitation method being used. The targets or visual elements, upon which the eyes are attempting to focus, can be of a variety of colors, sizes, shapes, and forms. They can change in color, size, shape, and form. They can contrast with other items being displayed to be more or less dominant in order to provide visual weight to enable fixation. These targets or visual elements can use specific colors with more saturation and can change in scale and proportion, all in an effort to draw the fovea toward a specific point of fixation on the target or visual element. With stereoscopic or 3-dimensional viewing, foveated rendering can also allow the image of interest to be seen in detail seen clearly and the remaining adjacent region is less detailed. Without using such enhancements to what is displayed, when performing VOR, DVA, or other ocular performance testing, the eyes tend to wander and have more microsaccades, which decrease the fixation ability and lessens the attentiveness of the person performing the test and the accuracy of testing. Generally, it is important to have some small point of focus on the visual element to lessen the microsaccades and enhance the fixation ability. These same targets or visual elements can be used for any oculomotor or ocular performance testing including VOR re-training when a VOR abnormality exists.

The ideas expressed in the previous paragraph can best be explained by looking at some examples. FIG. 19A shows an example of a target or visual element in the form of a soccer ball 902. This soccer ball could be part of an existing scene viewed on a VR or an AR display or viewed through an AR display or the soccer ball could have been added to the scene. The soccer ball could be spinning, which might make the pattern on the ball distracting. FIG. 19B shows the visual element (soccer ball) of FIG. 19A that has been altered by defocusing the ball 904, and superimposing a target in the form of a cross-hair 906, that is more precise for the eyes to focus on. It would be more accurate fixation for the eyes to focus on the center of the cross-hair element shown in FIG. 19B than the element shown in 19A due to the shape, size, contrast, and suppression of the pattern on the ball. Although this example has been done using a black and white image, color and color contrast can be more effective. For example, the visual element seen in the VR or AR platform display could be a red colored ball and within the center of the ball or a dark cross-hair surrounded by a lighter yellow circle could be placed. This strongly contrasted central focal point could help the eye focus on a specific point and lessen the "eye scanning" while undergoing any ocular performance measurement such as VOR testing or VOR re-training. In another example, the element being viewed can be in the shape of a familiar object, such as a basketball, football, helmet or object used in one's occupation. It can also have a centered focal point, created by high contrast and high color saturation compared to the surrounding background to maintain the foveal fixation duration attractiveness and lessen microsaccades.

FIG. 20 shows a scene that can be used for optokinetic testing in a virtual or augmented environment. In traditional optokinetic testing, a person's head is motionless while seated inside a moving drum with alternating black and white vertical lines or alternatively, a hand-held drum, with alternating black and white vertical lines, is placed in front of the person. The drum is slowly rotated. The alternating lines induce nystagmus and cause visually induced motion sickness. The movement of the eyes is measured as the drum rotates left and then right. Measurements can be at different drum speeds. This same test can be performed using an AR or VR platform by creating a visual image that includes elements that work just like the vertical lines in the drum. Examples of natural scenes that are similar to the drum with lines can include examples such as being seated in a car and watching a train go by or driving and watching the telephone poles move by, such as the scene 910 shown in FIG. 12. Similarly flying objects can be visualized as moving across the visual field or along another plane of motion beside the person. These visual elements can also change in size, color or other dimensions, as the person gets closer to the virtual object or further from the visual element. Motion can occur in any direction or depth relative to the person, as the eye movement is being assessed and measured.

Figure 21:
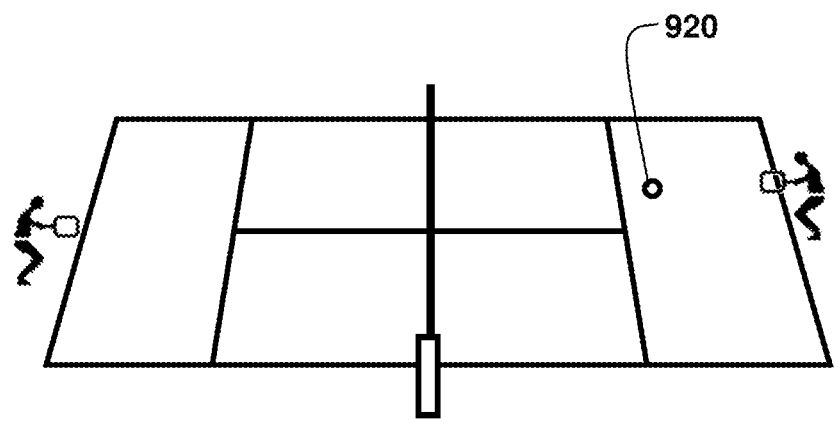
FIG. 21 shows a scene that can be used for testing eye-tracking performance.
Figure 22:
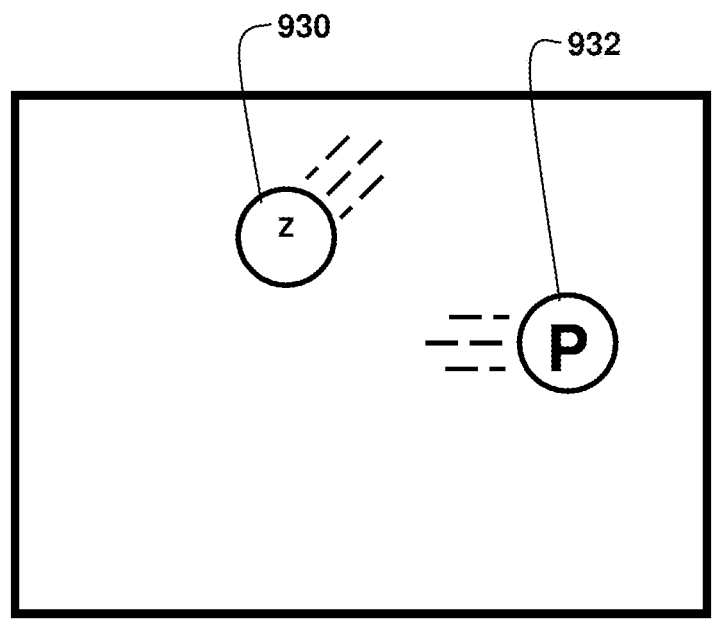
FIG. 22 shows a scene that can be used for dynamic visual acuity testing.
Figure 23:
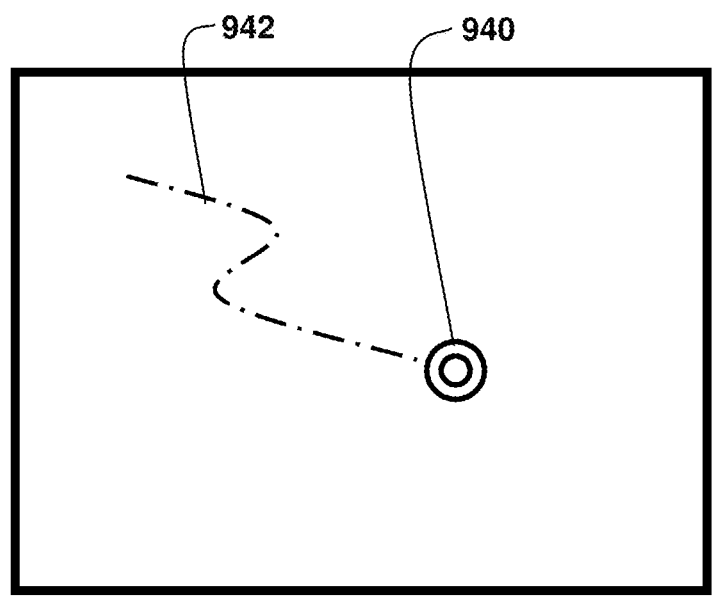
FIG. 23 shows a scene that can be used for scan path tracking.

FIG. 21, FIG. 22, and FIG. 23 illustrate other AR/VR/synthetic 3D display scenes that can be used for ocular performance testing such as VOR, DVA, visual pursuit, and/or fixation ability testing. These scenes can include a test environment comprising natural background features combined with a visual element or target whose shape, color, size, motion, depth, or other attributes have been selected or added to facilitate testing of vestibulo-ocular performance. FIG. 21 shows an example of a scene which illustrates what this type of ocular performance testing, such as with visual pursuit, DVA and/or VOR might look like. In the example shown in FIG. 21, the static scene can be a tennis court and the moving target is the tennis ball 920. The visual element (e.g., tennis) can remain motionless in the center, surrounded by a static court with 2 players on each side. The individual being tested would rotate his/her head in the horizontal and vertical plane while focusing on the visual element. Alternatively, as the person focuses on the static visual element in front of the player on one side of the court, it can suddenly become dimmed and re-appear on the other side of the court. The individual being tested is required to rotate the head each time the visual element reappears. This action can occur in a back and forth manner until the measurement is complete. For more complex testing, the surrounding courtside scene can be filled with fans who are in motion. As another example, if the VOR is being tested on a basketball player, the dynamic background features may be a basketball court surrounded by fans, who are yelling and moving and the visual element (e.g., basketball) may suddenly appear in the hands of a player on one side, then dimmed or removed, and then alternatively appear in the hands of another player on the other side, requiring the individual being tested to move the head in a horizontal manner. Visual pursuit can also be virtually measured using the basketball as the visual element to be tracked as it is in motion from player to player and being thrown upwards to the basketball hoop. This can be a more realistic method of assessing ocular performance with VOR and visual pursuit measurement. DVA measurement can also be performed with dynamic changes of the target or visual element of interest, requiring the person to identify characteristics of the element while it is in motion and the person is in motion and comparing this to the SVA prior to the onset of the DVA test. FIG. 22 shows letters that could be superimposed onto the moving element (such as the tennis ball in FIG. 21) to test DVA. The target visual element 920 in FIGS. 21, 930 and 932 in FIG. 22, or 940 in FIG. 23 could move in different trajectories, in different depths, the letters could be of different sizes, and the ball could move at different speeds and accelerations to provide a meaningful test as shown by comparing visual element 930 with visual element 932. The targets can be static or rapidly moving is a specific plane or scan path for (such as watching a tennis ball move across the court or with tracking tests that have a rotating target visual element) depending on the ocular parameter being tested.

DVA testing could be performed with lettered optotypes and as the head rotates back and forth, the letters can rotate in position. Alternatively, numbers can be used as well as other familiar images of objects. The images can also be native or natural to the background environment displayed. As the head rotates back and forth, the target or visual element is more difficult to visualize. If there is a VOR abnormality, for example the eyes will not be able to focus on the target or visual element of interest and will subsequently have less fixation and more errors in identifying a visual element. Measurement can also be performed with the visual element stationary and the head in motion or both the visual element and head in motion, which would be more realistic with everyday experiences. Static visual testing (SVT) can be performed to obtain a normal visual test. The visual acuity can be obtained, while the head and the visual element, or optotype being displayed are both motionless. Similar to a standard eye exam, an AR/VR platform can enable a person's static visual acuity (SVA), a component of DVA testing, by asking a person to identify a multitude of images or optotypes (letters, symbols, characters, figures of different sizes, shapes, orientation) on the visual screen.

Virtually, dynamic visual acuity (DVA), and retinal image stability (RIS), and foveal visual stability (FVS) testing can be used to determine the condition of a person's vestibulo-ocular reflex function. A DVA assessment can also include identifying a series of images or optotypes but with the addition of a head movement along an axis at a minimum rotational rate, engaging the vestibular system. The displayed images may also be dynamically moving in any direction, and can be random in position, appearance and presentation. Specifically, the image or visual element to be identified can be seen coming from any direction, randomly or with a specified pattern of motion, and may have different shapes, features, colors, sizes, orientation, patterns, or identifying characteristics, in a specific plane of axis or in variable plane, which the person must identify while the head in motion or rotating. The person can then provide feedback regarding what they see via an on-screen gesture, keyboard, smart device (e.g., defined as an electronic device, generally connected to other devices or networks via different wireless protocols such as Bluetooth, NFC, Wi-Fi, 3G/4G/5G cellular, etc., that can operate to some extent interactively and autonomously), eye or other physical response or by voice response. The comparison of the smallest image, visual image or optotypes correctly identified or the comparison of the correct numbers of images, visual elements or optotypes in both the DVA and SVA tests can determine if the person has a defect in his or her vestibulo-ocular reflex functions.

Visual pursuit testing can be performed with similar targets or visual elements of interest as have been described previously. Smooth pursuit testing has traditionally been performed with the head motionless and the eyes following a moving light or finger moving across a visual field. FIG. 23 shows a scene that can be used for scan path tracking in a virtual or augmented environment. An enhanced target visual element 940, can be sent across the scene along a specific path 942, while the measured eye movement follows the visual element. The path of these visual images or elements can assume any pattern, such as a zigzag, a saw toothed, or a square wave, or have a scan path that is snake-like, curved, circular, sinusoidal or rotational to provide a realistic and natural method of assessment of visual pursuit.

Figure 24:
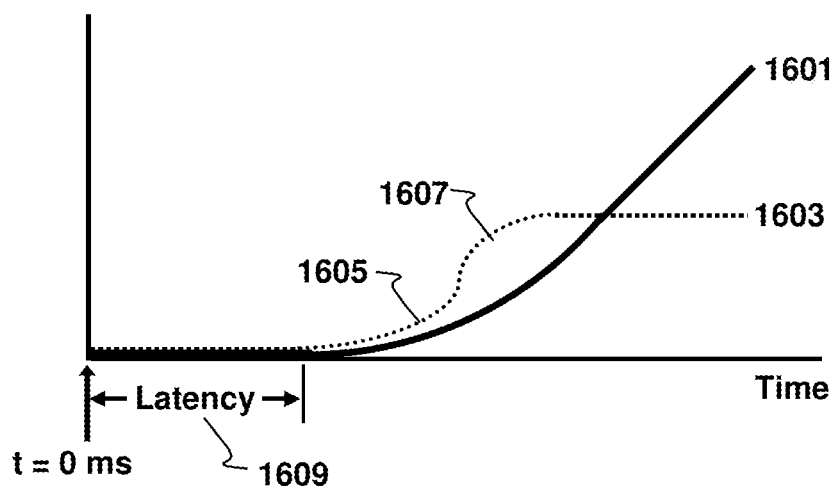
FIG. 24 shows the relationship between target movement, eye position, eye velocity, and eye acceleration for smooth pursuit.

FIG. 24 shows the relationship between target movement, eye position 1601, eye velocity 1603, and eye acceleration for smooth pursuit. The time when the target is moved is identified as t=0 ms. The eye position 1601, and eye velocity 1603, can then be tracked as a function of time. Latency 1609, is the delay from the time the target moves to the time the eye starts to move. Then the eye velocity 1603, will first accelerate 1605, and decelerate 1607, until the eye velocity 1603, matches the target velocity.

Figure 25A:
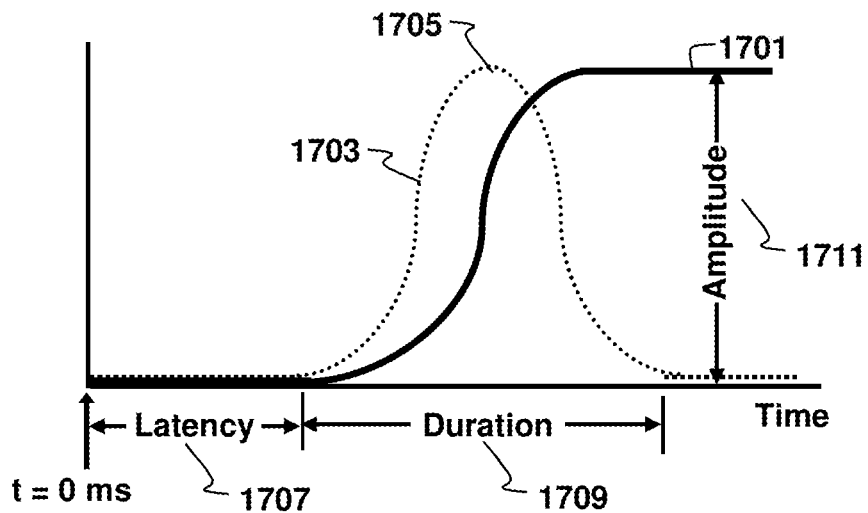
FIG. 25A shows the relationship between target movement, eye position, and eye velocity for a saccade.
Figure 25B:
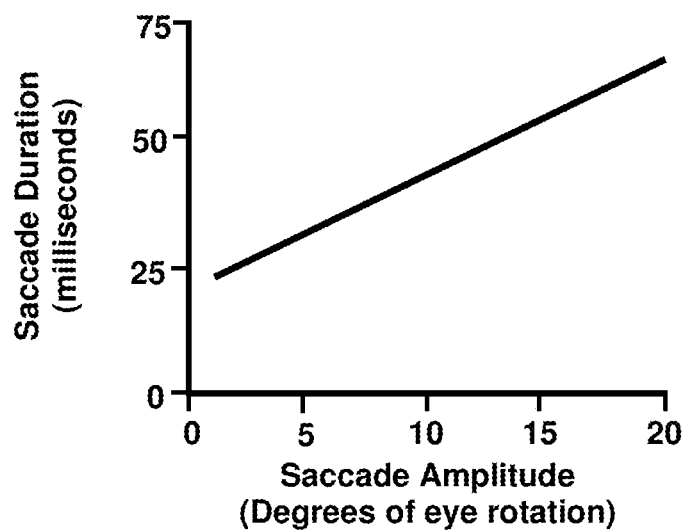
FIG. 25B shows the typical relationship between saccade amplitude and saccade duration.

FIG. 25A shows the relationship between target movement, eye position 1701, and eye velocity 1703, for a saccade. The time when the target is moved is identified as t=0 ms. The eye position 1701, and eye velocity 1703, can then be tracked as a function of time. Latency 1707, is the delay from the time the target moves to the time the onset of a saccade. As shown, the saccade eye velocity 1703, increases, reaches a peak velocity 1705, and then returns to zero. The length of time from the start to the end of this velocity curve is called the saccade duration 1709. The saccade eye position 1701, changes during this duration 1709 to reach a new position that differs from the initial eye position by a distance that can be defined as a saccade amplitude 1711. FIG. 25B shows the typical relationship between saccade amplitude and saccade duration.

Note that any of the testing described for any of these embodiments can be done with static targets or visual elements being viewed, or with dynamic targets or elements. The images or elements viewed may be familiar objects, such as balls, or objects more familiar to one's occupation. The visual target or visual elements may be displayed in a manner that is native or natural to the background.

Figure 26:
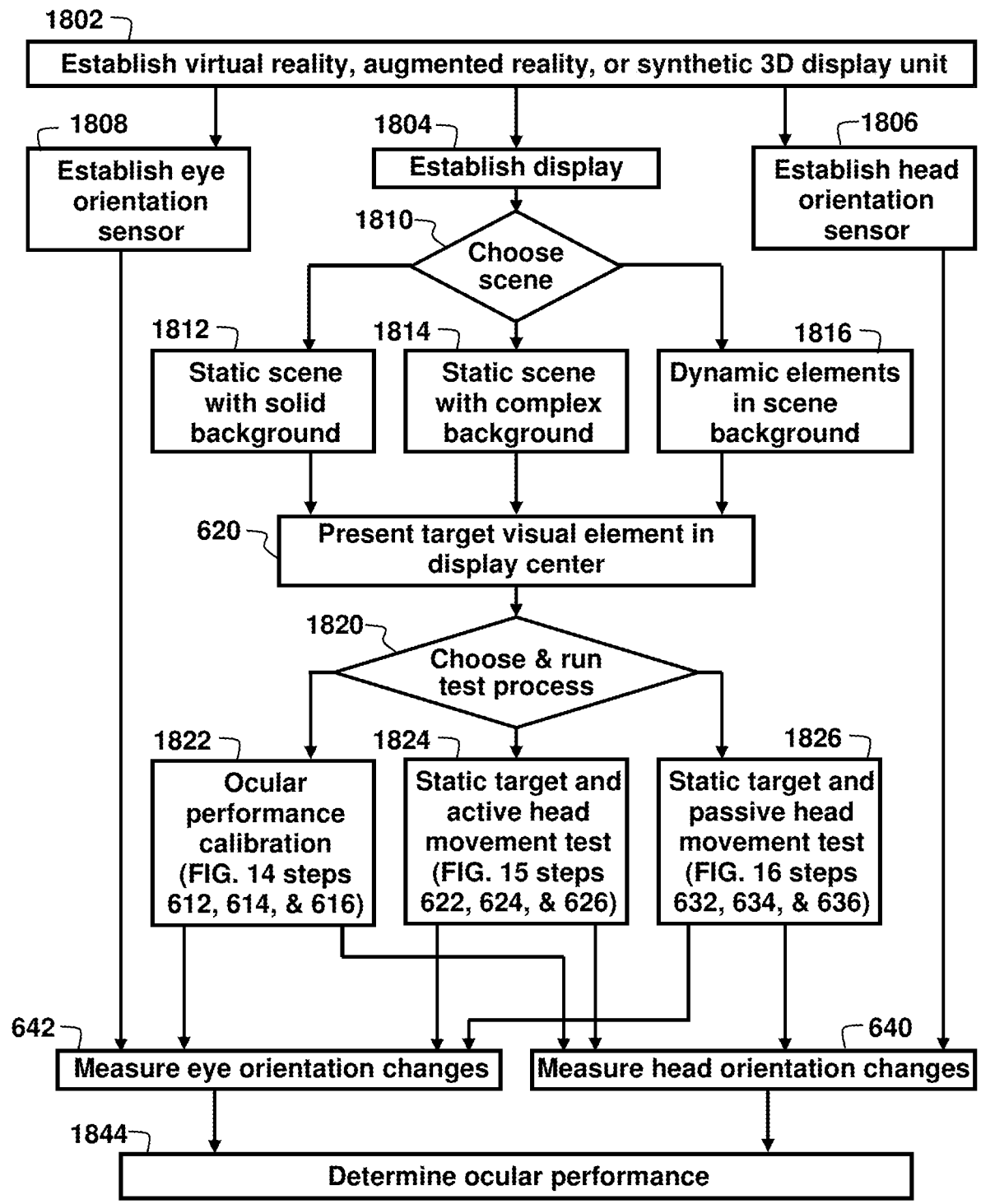
FIG. 26 shows a generalized method for ocular testing using virtual reality, augmented reality, or a synthetic 3-dimensional scene on a display.

FIG. 26 provides a more generalized embodiment of the system and method that was presented in FIG. 14, FIG. 15, and FIG. 16. Referring to FIG. 26, the head-worn virtual reality or augmented reality unit that was shown at 602, in FIG. 14, FIG. 15, and FIG. 16, can more generally also be a synthetic computer-generated 3D display unit and it does not necessarily need to be head-worn. Thus, it could be a VR/AR, or synthetic 3D display unit, as shown at 1802 in FIG. 26. The eye tracking video camera on the unit that was shown at 608, in FIG. 14, FIG. 15, and FIG. 16 can more generally be an eye orientation sensor and it does not need to be mounted as part of the unit. Thus, it could be simply an eye orientation sensor, as shown at 1808. Similarly, the display 604, and head orientation sensor 606, that were shown in FIG. 14, FIG. 15, and FIG. 16 do not necessarily need to be on the unit. They could be located somewhere else as shown at 1804, and 1806, in FIG. 26. As shown in FIG. 26, the process can further include the step of choosing a scene 1810, and the choices of scenes can comprise a static scene with a solid background 1812, a static scene with a complex background 1814, and/or scene with dynamic (i.e., moving) elements in the background 1816. The process shown in FIG. 26 includes the step of presenting a target visual element in the display center 610 and 620, just like the processes shown in FIG. 14, FIG. 15, and FIG. 16.

Further referring to FIG. 26, the method can comprise the step of choosing which ocular test to run on a subject as shown at 1820, and the choices can include ocular performance calibration 1822, static target and active head movement testing 1824, and/or static target and passive head movement testing 1826. Each of these three test processes (1822, 1824, and 1826) involves measuring eye orientation changes 642 and head orientation changes 640, just like the processes shown in FIG. 14, FIG. 15, and FIG. 16. The output of the process illustrated in FIG. 26 can be broaded (e.g., compared to FIG. 14, FIG. 15, and FIG. 16) and can comprise any ocular performance parameter discussed herein. These ocular performance parameters can include any of the following parameters that have been discussed in other parts of this disclosure, including but not limited to:

(a) vestibulo-ocular reflex;
(b) pupillometry;
(c) saccades (overt and covert);
(d) visual pursuit tracking;
(e) vergence (convergence and divergence)
(f) eyelid closure;
(g) dynamic visual acuity;
(h) dynamic visual stability;
(i) retinal image stability;
(j) foveal fixation stability;
(k) focused position of the eyes;
(l) visual fixation of the eyes at any given moment and
(m) nystagmus In an alternate embodiment to the configuration shown in step 1824 in FIG. 26, the visual target of interest can be dynamic and the head movement can also be dynamically moving in the same direction as the visual target movement. The process is repeated as many times as needed. This test can be conducted in the vertical, horizontal or any other direction.

Figure 27:
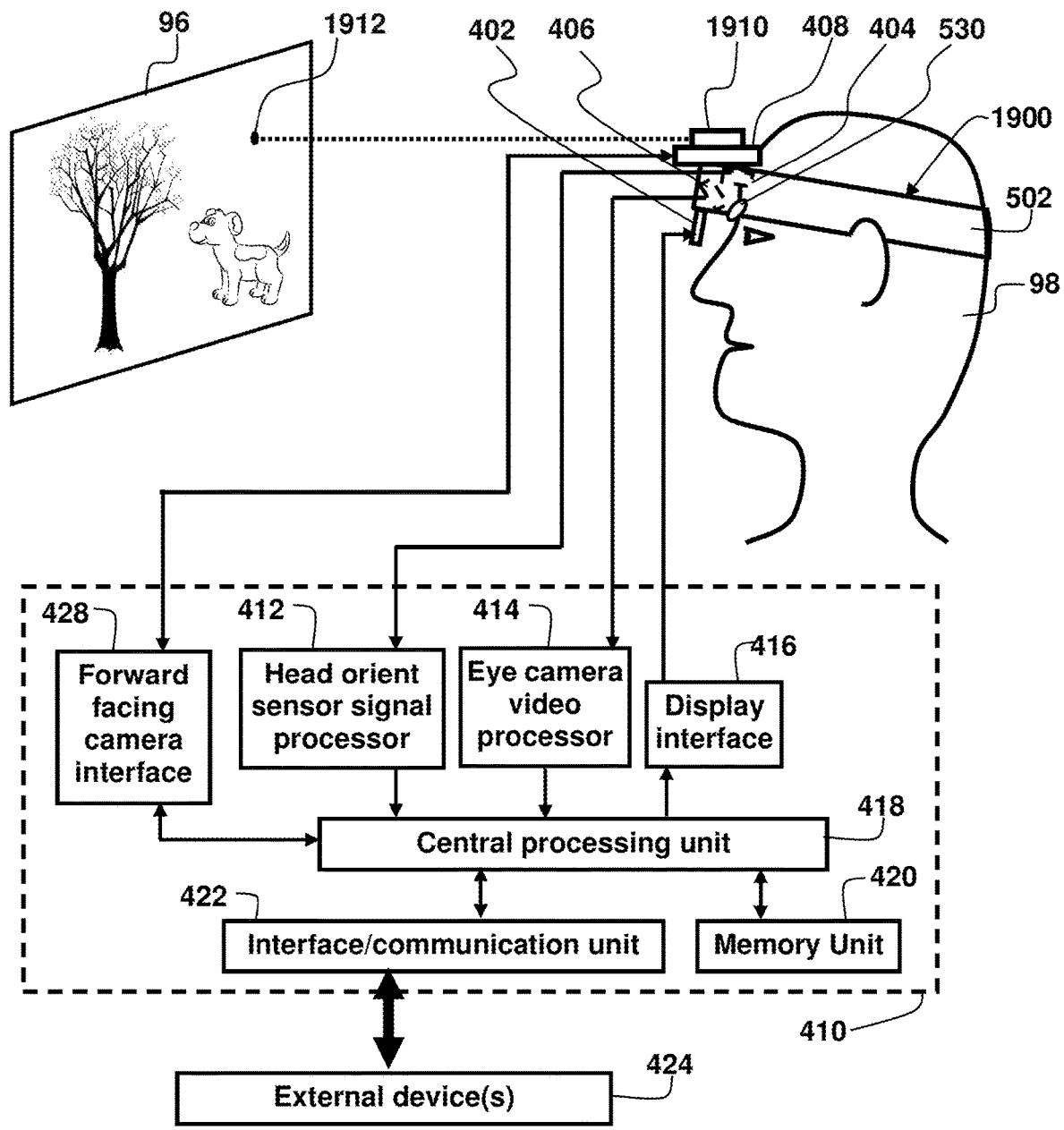
FIG. 27 shows an embodiment similar to that shown in FIG. 1 and FIG. 2, that further comprises a forward-facing camera and a light beam projector.
Figure 28:
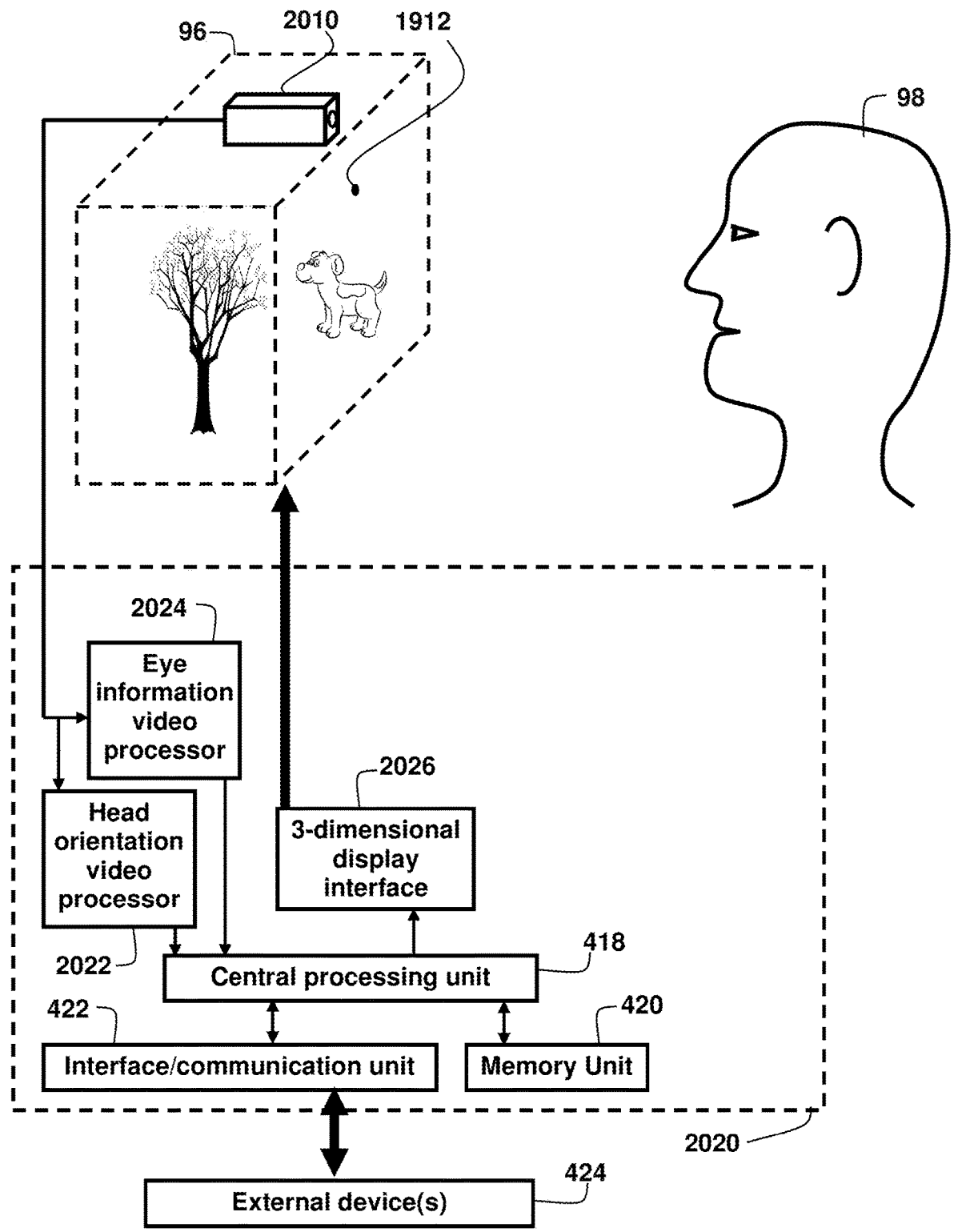
FIG. 28 shows an embodiment of a system similar to the ones described previously that requires no head-worn components.
Figure 29A:
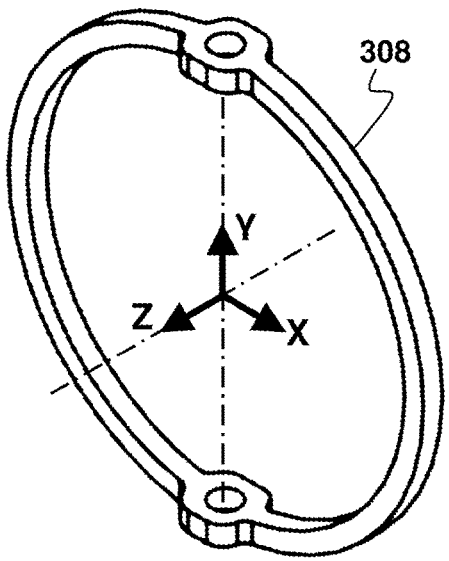
FIG. 29A, FIG. 29B, FIG. 29C, FIG. 29D, and FIG. 29E show ring-shaped leaf springs that can be used in alternate embodiment helmets.
Figure 29B:
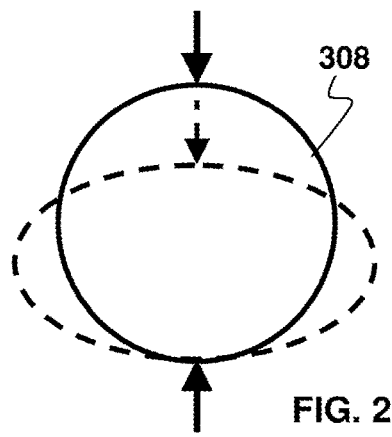
Figure 29C:
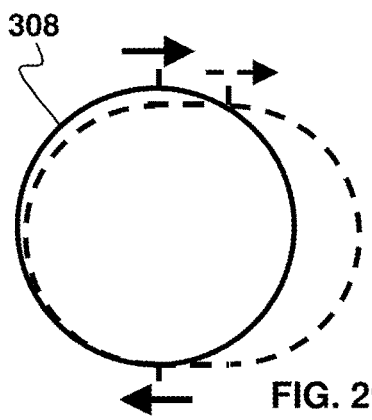
Figure 29D:
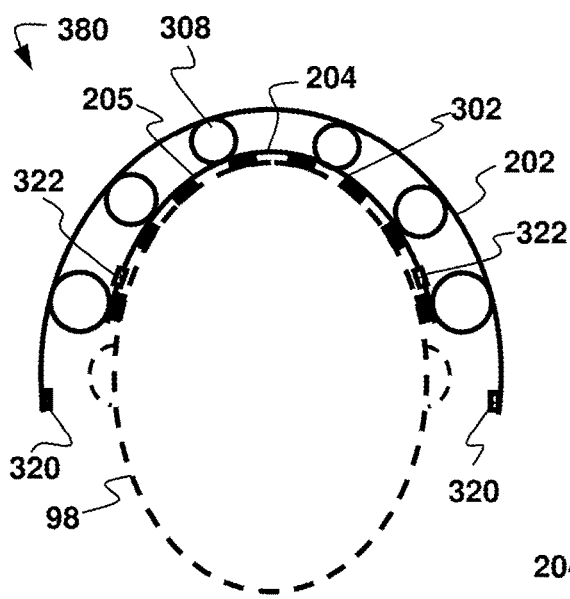
Figure 29E:
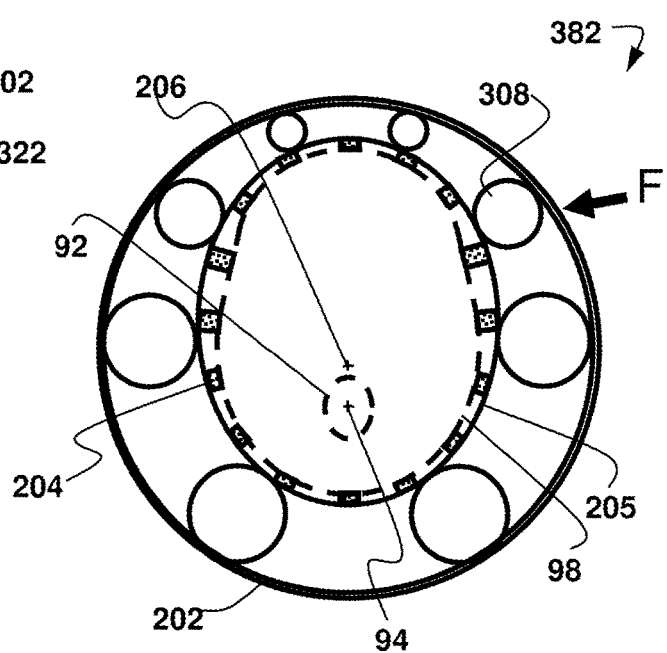

Embodiments of the invention can add an image or reference marker to a scene in order to measure ocular parameters of the types that have been discussed previously in this document. FIG. 27 and FIG. 28 show two configurations that can be used for doing this type of measurement. Other configurations for doing this type of measurement could be the Magic Leap TRADE system described in U.S. Pat. No. 10,191,294 and the HoloLens TRADE system described in U.S. Pat. No. 10,535,151. The Magic Leap TRADE system can be considered to be specialized glasses with augmented reality. The HoloLens TRADE system can be considered to be a specialized face shield with augmented reality.

FIG. 27 shows an augmented reality system at 1900. The augmented reality system 1900 is similar to the embodiments described with reference to FIG. 8, FIG. 11, and FIG. 13A. The embodiment shown in FIG. 27 uses a head band 502 as the structure for head attachment and has many other components similar to the systems described in FIG. 8, FIG. 11, and FIG. 13 with the same numbers in FIG. 27 referring to the same elements, features, or attributes. The augmented reality system 1900 shown in FIG. 27 can be used for ocular parameter tests as described in other parts of this document. FIG. 27 also shows a scene 96 that is visible to the user 98. The scene example 96 shows a tree and a dog. The scene 96 can be blank. The scene 96 could be comprised exclusively of static images, such as the tree. The scene 96 could include dynamic (i.e., moving) images, such as the dog.

In addition to all of the items described with regard to FIG. 8, FIG. 11, and FIG. 13, the embodiment of the augmented reality system 1900 shown in FIG. 27 further comprises a light beam projector, shown at 1910, and a forward-facing camera, shown at 408, responsive to eye sensors to measure various ocular parameters. The light beam projector 1910, can be a laser pointer or any other source of a light that can be projected from the head-worn device into the user's field of view, as depicted by the scene 96. The projected light can produce a spot or shape in the user's field of view that can serve as a reference point, a projected object that the user can focus on, as shown at 1912. The reference point or projected object generated by the light beam projector 1912, can be used as a target that the user is asked to follow or focus on as part of an ocular performance test. This reference point or projected object 1912, can be in addition to any information presented by the AR display 402, (also called a see-through display), or it can substitute for one or more of the functions of the AR display 402. For clarity, no connection has been shown between the light beam projector 1910, and the electronic module 410. However, it should be clear to anyone who understands the art that the light beam projector 1910 could be responsive to communication from the electronic module 410. Signals from the electronic module could travel to the light beam projector via a wired or a wireless connection. Such signals could control light intensity, size, shape, color, location, depth, and motion of the object 1912, generated by the light beam projector 1910, or any other parameter of the object capable of being understood by anyone skilled in the art.

Regarding the forward-facing camera, shown at 408 in FIG. 9, FIG. 11, FIG. 12A, and FIG. 27, it should be noted that this forward-facing camera 480 can be configured to record an image of what the user is seeing. In the embodiments discussed herein, the forward-facing camera 408, can be configured to determine, measure and log where the eyes of an individual, such as an athlete or military person, are looking during their play, occupational or military activities. This can be used to measure the duration of time an individual is visually focused on an object or target of interest. For example, this can measure if an athlete or military person can see an opponent or parts of an opponent (such as the hand or helmet) more quickly in time than others and how long the individual maintains focus on the visual object during the play or activity. This can be correlated with the eye tracking video camera 406, for measurement of reaction times. Individuals with highly focused ability on the object of interest can more accurately anticipate and more precisely predict the movements of their opponents. This data can be used in training and/or the selection process of individuals prior to performing the activities needed.

Further referring to FIG. 9, FIG. 11, FIG. 12A, FIG. 27, and other embodiments discussed herein, the forward-facing camera 408, can be configured to adjust its field of view, focal length, or to zoom in or out in response to an eye sensor. The electronic module 410, using the central processing unit 418, could control the forward-facing camera 408. This control of the forward-facing camera 408, could be through wired or wireless electronic signals. The forward-facing camera 408, could transmit video information to the electronic module 410, and this video information could analog or digital information and could be transmitted through a wired or a wireless connection. Any other component in the augmented reality system shown at 1900, could also be controlled through the forward-facing camera 408. The information collected and/or recorded by the forward-facing camera 408, can be responsive to the eye sensors 406, to measure ocular performance parameters. For VOR measurement, head rotation information would be measured using the head orientation sensor 404. The information collected and/or recorded by the forward-facing camera 408, could also be used, in conjunction with other information collected by the augmented reality system 1900 in FIG. 27, for capturing visual images of the user's surroundings, or activate a photo or video feature of the synthetic 3-D scene and determine the intended focal point of the use. As discussed previously, this determined intended focal point can be measured and correlated with the fixation accuracy of the eye tracking sensors. The user can also perform a predetermined action with the his/her eye(s) by focusing on a specific image or orienting the eye in a specific manner as an input control. Data collected can be uploaded and transmitted to a remote or external device.

FIG. 28 shows an embodiment of a system and method using AR/VR/3D simulation that is similar to the embodiments previously. In the embodiment shown in FIG. 28, the functions illustrated and described previously are performed without a head-worn device. In the embodiment shown in FIG. 28, the scene 96, is produced using an electronic module 2020, that comprises a 3-dimensional display interface (or device) 2026, for presenting the information. This 3D display interface/device 2026, could use any 3D display technology capable of being understood by anyone skilled in the art, including any of the 3D display technologies discussed in other parts of this document. Holography is one example of such a 3D display technology. Due to the realism available through the use of a 3D display device/technology, the person (or subject, or user), feels that they are immersed in the scene 96. Non-user-worn eye tracking can be accomplished using any of the technologies discussed in other parts of this document. The use of a video camera located above the scene 2010, is one example of such an eye tracking and head tracking technology. Non-user-worn head tracking could be accomplished using any of the technologies discussed in other parts of this document. The use of a video camera located above the scene 2010, is one example of such a head tracking technology. Note that in the embodiment shown in FIG. 28, the same video camera 2010, is used for both eye tracking and head tracking. This could also be accomplished using two separate cameras and any combination of any of the technologies discussed in this document. The video camera(s) 2010, could be connected to an eye orientation video processor 2024, and a head orientation video processor 2022, both of which can be connected to a central processing unit 418, in the electronic module 2020. The visual object 1912, that can serve as a target, as described with reference to FIG. 27 can be generated as part of the scene 96. This target 1912, could be stationary (static) or it could be dynamic (moving). The electronic module 2020, through the display interface 2026, can control the target 1912. The electronic module 2020, comprising a central processing unit 418 and a memory unit 420, can also be used to record display information, head orientation information, and eye information to keep a record of a test for subsequent analysis. The system shown in FIG. 28 can further comprise an interface and/or communication unit 422, which can be configured to communicate with an external device or remote devices 424. Any ocular performance measurements with the system shown in FIG. 28 can be done using any of the methods described in other parts of this document.

Further referring to FIG. 28, ocular parameters can be measured using static or dynamic images projected in the display scene 96, either with the head motionless or moving. The 3-dimensional scene can comprise a solid unobtrusive background or a background resembling typical natural activity. Any of the visual targets or visual elements previously discussed can be applied to this configuration. The 3-dimensional background scene, provided by the 3D display, can be limited or fully immersive with images that extend around 360-degrees around the subject as well as above the subject in a full hemispherical or spherical configuration that surrounds the subject. viewed images.

In one embodiment, the 3D image is generated using a hologram. The user has in his visual field a holographic scene, which as an example may resemble basketball court, occupied by other players and the stands are filled with fans. The holographic scene can be varied having static or dynamic features. The user's eye movements can be measured by the remote eye sensors 2010, while visually immersed within the scene. VOR testing, pursuit tracking and other ocular parameter measurements discussed herein can be performed while seemingly involved in the play activity. This type of measurement can also be performed in other environments more familiar to the user (e.g., a football field, tennis court, military activity). Alternatively, in another similar embodiment, the user can be wearing a device comprised of an eye tracker, head tracker, forward-facing camera and laser projector, while the human ocular performance is measured. A synthetic 3D display system can be used using holographic imaging or a volumetric display. In this embodiment, a light beam projector or a laser hologram can be used to project a target of interest or visual element into the 3-dimensional display scene. This target of interest can be an image of a white dot, or other enhanced visual target upon which the user can focus. The ocular performance can be measured similar to that previously described in FIGS. 14, 15, 16, and 26. The measured visual element being viewed can be projected from the laser projector while the user is seemingly immersed in the scene of the holographic imaging or a volumetric display. A forward-facing camera can be oriented to capture visual images of the user's surroundings, or activate a photo or video feature of the synthetic 3-D scene and determine the intended focal point of the use. This determined intended focal point can be measured and correlated with the fixation accuracy of the eye tracking sensors. The user can also perform a predetermined action with the his/her eye(s) by focusing on a specific image or orienting the eye in a specific manner as an input control.

FIG. 27 and FIG. 28 show two systems for measuring ocular parameters using a dot in a person's field of view. Similar ocular parameters could be measured using augmented reality. For example, when testing for the VOR the user may be presented with an augmented reality image of a baseball in the center of a field, which remains motionless while moving the head horizontally or vertically. In a similar manner, visual pursuit can be performed while the user's head is motionless, and the user is presented with an augmented reality image of a baseball in moving through space. Head tracking and ocular-based sensors can be separately located in the system in any of the locations described in this document. A forward-facing camera of the scene can also be in integrated into the system to ensure accuracy of eye fixation of an image. The sensors and forward-facing camera can all communicate with each other and the electronic circuit. The augmented reality image that is presented to the user can interact with the user, such that the user can appear part of the digital or synthetic scene during the testing. The use of augmented reality can also encompass any one of the embodiments in this document.

Embodiments for applications of ocular parameter measurement as described in this document can be done using Magic Leap, HoloLens and any other augmented reality systems. Such an embodiment would enable VOR testing to be done in a much more immersive manner. For example, the user could be physically in a natural scene such as in a field. A virtual image of a ball could be visualized by the user in the field and it could be suspended in space or static. The user could move the head horizontally and/or vertically and eye sensors and head orientation sensor can measure the VOR.

In another application of augmented reality, the user can again be located physically in a field. A digital virtual image of a ball can be seen in the field, for the user to focus upon and it can have dynamic activity (motion). Visual pursuit tracking can be measured with saccades, using at least one eye sensor as the virtual image moves across the natural scene of the field. The virtual image of the ball can assume any type of motion, such as a circular or sinusoidal motion.

In another application using augmented reality, vergence could be measured in a similar fashion with a digital virtual image moving in an anterior or posterior direction (e.g., in the Z axis) in the natural physical scene where the user is located. As an example, a virtual image of a baseball can be used as a visual element which the user can focus upon. The virtual image of the ball can appear as though it is thrown to the user. The ball would have a larger appearance as it got closer to the user and convergence could be measured as the virtual ball gets closer to the eyes. The virtual visual images can be a single image or multiple images and assume any form or character.

The augmented reality systems for measuring ocular parameters using a virtual image can also be configured with a forward-facing camera, which can be responsive to eye sensors and can also verify accuracy of the eye sensors regarding where the eyes are focused.

As an alternative to the helmet embodiments that were shown in FIG. 4A to FIG. 6F, one, or more, or all of the elastically resilient impressions shown at 304 and 306 in FIG. 4A to FIG. 6F could be replaced with a ring-shaped leaf spring shown at 308 in FIG. 29A, FIG. 29B, FIG. 29C, FIG. 29D, and FIG. 29E. By choosing the material, diameter, radial wall thickness, and axial thickness (in the Z-direction in FIG. 29A) of the ring-shaped leaf spring 308, it can be understood that it is possible to independently specify the stiffness in compression (shown in FIG. 29B), shear in the plane of the ring-shaped leaf spring (shown in FIG. 29C), and shear in the direction perpendicular to the plane of the ring-shaped leaf spring (not shown, but understandable by someone skilled in the art). By choosing the quantity and orientation of the ring-shaped leaf springs 308, as shown by the section views shown in FIG. 29D (which is similar to FIG. 5A) and FIG. 29E (which is similar to FIG. 4A), it can be understood that the compliance of the helmet outer shell 202 relative to the inner frame 205 can be adapted to whatever characteristics are being sought, such as the helmet embodiments shown at 380 in FIG. 29D or 382 in FIG. 29E. These helmet embodiments, 380 and 382, can use the same head confirming pads 204 to fit the person's head 98 as were shown previously. The rotational center of the helmet 206 can also be closely or exactly aligned with the rotational center of the wearer's head 94, which is located in the foramen magnum 92. These helmet embodiments 380 and 382 can also use the same sensors, shown at 320 and 322, that were discussed with reference to FIG. 5A and FIG. 5B.

Sensors

Embodiments of the invention(s) disclosed herein utilize sensors. These sensors are also referred to as sensing elements/transducers. In embodiments disclosed herein, these sensors can be used to detect and measure specific physical phenomena such as ocular parameters and head orientation. There can include sensors that measure physiologic, biochemical, and biometric values associated with the user. The face shield or other device can incorporate sensors or sensing elements/transducers to measure various properties of the impact, or other physical measures of the user.

Embodiments of the disclosed device can be comprised of sensing elements/transducers are located in the impact mitigation layer of a helmet to adjust the rotational and linear impact mitigation system to be centered circumferentially above the foramen magnum and around the pivot point at the upper spinal cord, and brainstem junction as seen in the horizontal plane, to reduce rotational acceleration with tangential blows to the head. These sensing elements/transducers can keep the configuration of more padding posteriorly to keep the center of the helmet, when viewed horizontally proximate to the foramen magnum. Further embodiments enable the sensing elements to change characteristics of the padding deployed in response to input signals. One example would be a pneumatic impact mitigating element (e.g., pneumatic/inflation bag, cushion, pad or device) from the external shell, other layer, an adjacent material or nearby worn padding, which can be altered, or changed in its characteristics prior to imminent impact to provide an additional air protection system to the head and or neck. The sensing elements, sensors, or transducers can exhibit artificial intelligence in response to imminent blow information detected and the measured threshold values to determine the abnormal value necessary to elicit a response in order to maintain health of the user. The sensing elements, sensors, or transducers can detect and respond to an imminent occurrence when two or more bodies come together or violent blows to head by making changes or adjustments in the impact material, by increasing the padding, altering the shape of the elastomeric properties or altering the characteristics of the impact reduction material within the helmet, to mitigate the force exerted upon the head. These sensing elements/transducers can be self-altering, self-adjust, change shape or characteristics after an impact and resume pre-impact status. Embodiments also comprise sensing elements, sensors, or transducers which also allow observers to remotely check the status any of the sensing elements/transducers described and can change the parameters of the sensing element/transducer measurement or sensitivity if needed. Sensing elements/transducers on the external shell of a helmet can record information of how many times a head receives hits before specific thresholds are reached indicating an abnormality. Other embodiments can also measure other impact information, including but not limited to linear acceleration, rotational acceleration, impact duration, impact location. Although current biomechanical measure of the severity of a single impact cannot predict concussions in football with a high positive predictive value. A composite variable that contains aspects of linear acceleration, rotational acceleration, impact duration, and impact location is more sensitive to the incidence of concussions. Artificially intelligent sensing elements/transducers can also change impact mitigation material characteristic shape and resistance, depending on the power of blow detected and the location of the blow to the head, consistent with an ideal force displacement ratio. The sensors and sensor locations described with regard to the helmet could instead be placed on the face shield to measure any of the parameters discussed.

These sensing elements/transducers can be pressure sensitive, ultrasonic, mechanic, electrical, electromagnetic, responsive to haptic, graphene, PVDF (polyvinylidene fluoride sensing, fluid-based sensing elements/transducers, microelectromechanical systems (MEMS)-based on accelerometers, silicon-based solid-state accelerometers, binary sensing elements of plastic housing and working fluids to detect instantaneous acceleration (impact).

Eye Tracking

Measuring eye muscle movement responses, related to eye fixation tasks, can be a reliable indicator of visual/vestibular functional health and can provide a rapid method to detect concussions/TBIs. This refers to such ocular parameters as the VOR, saccades, vergence, visual pursuit, pupillometry and the other characteristic previously defined.

The VOR allows for eye movements in the opposite direction of head movement to maintain steady gaze and prevent retinal image slip. Motion signals from the utricle, saccule, and/or semicircular canals in the inner ear travel through the utricular, saccular, and/or ampullary nerves to areas in the vestibular nucleus, which sends output to cranial nerve III, IV, and VI nuclei to innervate the corresponding muscles. Horizontal VOR involves coordination of the abducens and oculomotor nuclei via the medial longitudinal fasciculus. An abnormal VOR will involve catch-up saccades while the patient rotates his or her head, and it can indicate bilateral, complete, or severe (>90%) loss of vestibular function. VOR can be assessed in several ways. During the Doll's eye maneuver, the patient continuously fixates on an object while the examiner moves his or her head from side to side, and the examiner watches the patient's eyes for catch-up saccades. VOR can also be assessed with visual acuity testing, during which multiple visual acuity measurements are taken as the head oscillates. A loss of three or more lines of visual acuity is abnormal and indicative that the patient's VOR is grossly reduced. Caloric stimulation can also be used to examine the VOR. Irrigation of the external auditory meatus with ice water causes convection currents of the vestibular endolymph that displace the cupula in the semicircular canal, which induces tonic deviation of the eyes toward the stimulated ear. Examination of the VOR can be more accurately be performed using eye tracking and head tracking sensors, either dynamically (e.g., another person moves the head while the person being tested focuses on an image element) or actively (e.g., where the person moves their own head while focusing on the image element). If the VOR is abnormal, catch-up saccades will be measured. Saccades are quick, simultaneous movements of both eyes in the same direction. Humans do not look at a scene in fixed steadiness, the eyes move around, locating interesting parts of the scene and building up a mental, three-dimensional 'map' corresponding to the scene. We cannot consciously control the speed of movement during each saccade; the eyes move as fast as they can. After gazing on a moving target of interest, which was initially motionless, it takes about 200 ms for eye movement to begin. During this delay, the position of the target with respect to the fovea is computed (that is, how far the eye has to move), and the difference between the initial and intended position, or "motor error", is converted into a motor command that activates the extraocular muscles to move the eyes the correct distance in the appropriate direction. Saccadic eye movements are said to be ballistic because the saccade-generating system cannot respond to subsequent changes in the position of the target during the course of the eye movement. If the target moves again during this time (which is on the order of 15-100 ms), the saccade will miss the target, and a second saccade must be made to correct the error. While visual information is not processed during saccadic eye movements, they still can provide information about viewing behavior. According to the theory of visual hierarchy a stimulus is inspected by scanning it through a sequence of visual entry points. Each entry point acts like an anchor, which allows the user to scan for information around it. According to this perspective, longer duration of saccadic eye movements could indicate increased cognitive effort in finding a suitable entry point into a visual display. One reason for the saccadic movement of the human eye is that the central part of the retina (known as the fovea) plays a critical role in resolving objects. By moving the eye so that small parts of a scene can be sensed with greater resolution, body resources can be used more efficiently. The saccade that occurs at the end of a head turn with someone who has an abnormal VOR is usually a very clear saccade, and it is referred to as an overt saccade. An overt saccade is indicative of abnormal semicircular canal function on the side to which the head was rotated. Covert saccades are small corrective saccades that occur during the head movement of a person with abnormal inner ear function. Covert saccades reduce the need for overt saccades that the end of the head movement and are more difficult to identify than overt saccades. Covert saccades are very fast. This makes them almost impossible to detect by the naked eye, and therefore sensitive eye tracking measurements are typically required to detect covert saccades. There is a rapid deceleration phase as the direction of sight lands on the new target location. Following a very short delay, large saccades are frequently accompanied by at least one smaller corrective saccade to further approach a target location. Corrective saccades can occur even if the target has been made to disappear, further supporting the projected, ballistic nature of saccadic movements. However, corrective saccades are more frequent if the target remains visible. Saccade accuracy, amplitude, latency and velocity can be measured with oculomotor eye movements, most commonly with saccades, vergence, smooth pursuit, and vestibulo-ocular movements. Saccades can be elicited voluntarily, but occur reflexively whenever the eyes are open, even when fixated on a target. They serve as a mechanism for fixation, rapid eye movement, and the fast phase of optokinetic nystagmus. The rapid eye movements that occur during an important phase of sleep are also saccades. The latency, amplitude, accuracy and velocity of each respective corrective saccade and latency totals and accuracy can be calculated. For saccadic amplitudes up to 15 or 20°, the velocity of a saccade linearly depends on the amplitude (the so-called saccadic main sequence). Saccade duration depends on saccade amplitude. In saccades larger than 60 degrees, the peak velocity remains constant at the maximum velocity attainable by the eye. In addition to the kind of saccades described above, the human eye is in a constant state of vibration, oscillating back and forth at a rate of about 60 Hz.

Vergence eye movements are used to track objects that move in depth in one's binocular visual field to attain and maintain a fused and single percept. When we shift our gaze from a far object to a near object, our eyes converge, the lenses of our eyes modify their focus (accommodate), and our pupils often constrict. These three combined responses are termed the near triad. Convergence is the simultaneous inward movement of both eyes toward each other, usually in an effort to maintain single binocular vision when viewing an object. This is the only eye movement that is not conjugate, but instead adducts the eye. Divergence is the simultaneous outward movement of both eyes away from each other, usually in an effort to maintain single binocular vision when viewing an object. It is a type of vergence eye movement. The mechanism and control of vergence eye movements involves complex neurological processes that may be compromised in individuals with traumatic brain injury, thus frequently resulting in a wide range of vergence dysfunctions and related near-work symptoms, such as oculomotor-based reading problems. Vergence requires that the occipital lobes be intact, and the pathway involves the rostral midbrain reticular formation (adjacent to the oculomotor nuclei) where there are neurons that are active during vergence activities. It comprises a complex and finely tuned interactive oculomotor response to a range of sensory and perceptual stimuli. There is an important interaction between the vergence system and vestibular (inner ear balance) system. To keep the eyes focused on a visual element or object of interest, while the head is moving, the vestibular system senses head rotation and linear acceleration, and activates the eyes to counterrotate to keep gaze constant even though the head is moving. Vergence can be adversely affected not only by concussion and traumatic brain injury (TBI) but also by factors including aging and visual abnormalities.

It has been observed that concussions and mild traumatic brain injury adversely affects the pupillary light reflex suggesting an impairment of the autonomic nervous system. Quantitative pupillary dynamics can also serve as an objective mild traumatic brain injury biomarker and these pupillary measurements can be reliably replicated. Pupil diameter changes are controlled by the involuntary nervous system, can also serve as a reliable proxy of mental effort.

By tracking the movement of the visual target, the eyes maintain a focused image of the target on the fovea. A visual stimulus (the moving visual target) is required to initiate this eye movement. Pursuit gain, which is the ratio of eye velocity to target velocity, is affected by target velocity, acceleration and frequency. Visual pursuit tracking may be related to factors that are difficult to quantify, such as the degree of alertness present in persons, visual acuity or the visibility of the pursuit target. Visual pursuit tracking can be decayed with alcohol, centrally acting medications such as anticonvulsants, minor tranquilizers, preparations used for sleep. It is also clear that visual pursuit performance declines with age and can be adversely affected by vestibular dysfunction, central nervous system disorders and trauma, such as concussions and traumatic brain injury (TBI). Visual pursuit differs from the VOR, which only occurs during movements of the head and serves to stabilize gaze on a stationary object. Most people are unable to initiate pursuit without a moving visual signal. The pursuit of targets moving with velocities of greater than 30°/s tend to require catch-up saccades. Most humans and primates tend to be better at horizontal than vertical smooth pursuit, as defined by their ability to pursue smoothly without making catch-up saccades. Most humans are also better at downward than upward pursuit. Pursuit is modified by ongoing visual feedback. Smooth pursuit is traditionally tested by having the person follow an object moved across their full range of horizontal and vertical eye movements.

To measure some specific eye responses (such as VOR), both eye tracking and head tracking measurements are required. For measurement of other ocular parameters only eye sensors are needed. Eye tracking is the process of measuring either the point of gaze (where one is looking) or the motion of an eye relative to the head position. An eye tracker is a device for measuring eye positions and eye movement. Eye tracking and/or measurement of ocular parameters in embodiments of the device can include the following features:

a. Using sensors located in or attached to the framework of the face shield;
b. Using sensors embedded in the transparent face shield material;
c. Using sensors embedded in the transparent AR or other display system
d. Having sensors in the framework and in the transparent shield and/or display system in any combination
e. Projecting images onto a region of the face shield or display system visible to the wearer, using a variety of light sources to create the image seen by the user The eye tracking and/or measurement can also be done:
a. in a non-contact fashion with the use of a light source (invisible light, such as with the use of an infra-red camera or light, or visible light);
b. by using a video camera, image camera or other sensor system designed to visually capture and record the eye movement activity; and/or c. with a magnetic system such as one using magnetized contacts and an external detector.

If one or more video cameras are to be used for eye tracking, it is desirable to have a sampling rate at least 60 frames per second (60 Hz) and preferably at least 90-120 Hz. Many video-based eye trackers have sample rate of at least 30, 60, 90, 120, 250, 350 or even 1000/1250 Hz. In embodiments of the present invention, a sampling rate minimally of 60 Hz, may be used for eye tracking, but more typically at 120 Hz-350 Hz or higher may be needed to capture fixation of eye movements or correctly measure other saccade dynamics or capture the detail of the very rapid eye movement during reading, or during neurological evaluations, such as with concussions.

Modern cameras are capable of operating over a wide range of frame rates. Instantaneous frame rates can also be adjusted (i.e., governed by so-called "clock" circuitry) as frequently as on an image-by-image basis. Closely aligned with camera frame rate is the acquisition time required to collect each image. The maximum time a camera can take to acquire an image is the inverse of the frame rate (i.e., the total time of a frame=/frame rate). The key to accurately determining initial saccadic direction and speed is the acquisition of camera images at high frame rates (typically hundreds of frames per second). Several techniques are available to acquire a rapid sequence of images immediately following a saccadic launch: 1) Once a saccadic launch is detected when sampling at a lower frame rate, the camera is immediately switched to a higher frame rate. 2) Camera circuitry (only) can be constantly run at a high frame rate, storing images within a circular buffer. Not all images are transferred out of the camera buffer and processed during normal operations. When a saccade is detected, rapidly sampled images that had been stored in the camera buffer can be retrieved for processing. 3) Frame rate can be adjusted based on the "context" of eye signal control. High frame rates can be maintained throughout these sequences.

The eye tracking and/or measuring system may include hardware such as an infrared camera and at least one infrared light source, a video tracking system and recorder or data logging unit. The infrared camera may be utilized by the eye tracking system to capture images of an eye of the wearer. The video images obtained by the infrared camera regarding the position of the eye of the wearer may help determine where the wearer may be looking within a field of view of the head mounted display used in the system. The infrared camera may include a visible light camera with sensing capabilities in the infrared wavelengths. Infrared light or radiation is a longer-wavelength radiation than visible light. It exists just outside of the spectrum of visible light. Heat, or thermal energy, is a common source of infrared light. An infrared camera is a device specially designed to detect and display the sources of this kind of light. A thermal infrared camera converts the heat detected into electrical signals, which are then projected in an image. Many types of night vision cameras are based on infrared light. A human body will always emit heat, and infrared cameras will detect this radiation.

The infrared light source can include one or more infrared light-emitting diodes or infrared laser diodes that may illuminate a viewing location, i.e., an eye of the wearer. Thus, one or both eyes of a wearer of the system may be illuminated by the infrared light source. The infrared light source may be positioned along an optical axis common to the infrared camera, and/or the infrared light source may be positioned elsewhere. The infrared light source may illuminate the viewing location continuously or may be turned on at discrete times.

Eye sensors which track different locations on the surface of one or both eyes to determine gaze-tracking locations, utilizing multiple illumination sources and/or multiple cameras to generate and observe glint/reflections from multiple directions can be used improve the accuracy of gaze tracking. One or more of the illumination sources can be comprised of infrared, near infrared or visible light, such as a micro-LED or micro-OLED projector. Eye sensors can also obtain biometric information. Eye sensors can be used to obtain anatomic structures and features of the eye, movements of the eye and eyelids, responses and reflexes of the eyes and eyelids. Eye tracking data can also be collected using a multi-camera eye gaze tracker, which is based on one-camera gaze estimation algorithm. Using an algorithm, the 3D eyeball position can be estimated by the two corneal surface reflections (or glints) of the IR lights. Each camera can estimate the gaze independently and can allow large head movement. The accuracy of this system is less than 1 degree.

Eye sensor or image sensor data collection can be based on ambient/natural light, infrared, near infrared or non-traditional methods such as ultrasonic or by pulsed laser light. The software used to capture the data is often selected on the basis of the final image result needed or desired when viewing images in motion. One approach is the use of a global shutter which captures an entire frame all at once. Image sensors with a global shutter allow all of the pixels to accumulate a charge with the exposure starting and ending at the same time. At the end of the exposure time, the charge is read out simultaneously. In turn, the image has no motion blur on moving objects. A rolling shutter is much different and unlike a global shutter where the sensor is exposed all at once, a rolling shutter is exposed in a progressive motion. Image sensors with a rolling shutter do not expose all the pixels at the same time. Alternatively, they expose the pixels by row with each row having a different start and end time frame. The top row of the pixel array is the first to expose, reading out the pixel data followed by the 2nd, 3rd & 4th row and so on. Each of the rows, at the beginning and end point, have a delay as the sensor is fully read out. The result of this on moving objects is a skewed image. A camera can be used as a sensor for detecting light in high resolution. When tracking and/or measuring the eye activity or eye movement, such as the VOR, an IR or video camera may be used and can be comprised of a single camera system or a multiple camera system.

Other light sources in the device can be used to provide the visualized images in the transparent AR display screen. These light sources can guide light across multiple layers of the transparent display material to create multiple focal planes and providing digital holographic or 3D visual elements in a natural environment for the user to view.

A thin prism can be used between the eye and a camera system, which acts as a light-guide altering the imaging path between the camera and the eye. The use of a thin prism can also provide on-axis illumination. This arrangement can enable an eyeglass like eye tracking device, which captures a frontal (i.e., on-axis) or near frontal image of the eye to have a visually appealing form factor.

A beam splitter in a face shield, visor or accessory device can be used, of which an eye is imaged by a camera positioned out of a user's line of sight. A beam splitter is an optical device that separates a beam of light into two or more different beams of light. Beam splitters are available in various forms. These include cubes, pipes and plates. What happens with a beam splitter is that it accepts the input beam and then proceeds to divide the light depending on the specified requirements. The input beam could be polarized or non-polarized light. The most commonly used is the cube beam splitter although the plate beam splitter is typically used to produce lower cost non-polarized beam splitters. These typically provide a 50-50% split ratio. The reflected and transmitted light emerging from the beam splitters are at various angles, which often necessitates external mirrors to redirect the light. Embodiments of the present invention can utilize single prism beam splitters and/or compound beam splitters formed from combining one or more of the single prism beam splitters. The beam splitters can be configured to produce one or more split beams of light that emerge from the prism at angles other than 90° to one another. The prisms can be configured so that the light propagating through the prisms encounters one or more intermediate planar surfaces at various angles with respect to the path of the light. A certain number of the intermediate planar surfaces can be angled so that the light transmitted along a particular path undergoes total internal reflection (TIR) at these intermediate planar surfaces. A number of other intermediate planar surfaces can be positioned or angled so that the light transmitted along a particular path does not undergo TIR.

Eye tracking using binocular horizontal and vertical eye position estimates can be derived from the relative positions of multiple corneal reflections and the center of the pupil. By using two eye landmarks (corneal surface reflections and pupil center) whose relative position are invariant under translation, the angular position of the eye independently of lateral motion of the video system relative to the head is able to be estimated.

When using an eye-tracking camera, two general types of eye tracking techniques can be used: Bright Pupil and Dark Pupil. The dark and bright pupil tracking techniques are based on the iris-pupil boundary detection. Light sources in the near IR spectrum are often used for these two approaches. The difference between these eye-tracking techniques is based on the location of the illumination source with respect to the optics. In the bright pupil approach, the infrared source is placed near the optical axis, while in dark pupil it is placed farther away from this axis. Therefore, in the bright pupil approach, the video camera records the infrared beam reflected by the subject's retina, making the pupil brighter than the iris, while in the dark pupil approach, the reflected infrared beam is not recorded by the camera and the pupil becomes darker than the iris. For the bright pupil approach, the infrared illumination is coaxial with the optical path and the eye acts as a retro-reflector as the light reflects off the retina creating a bright pupil effect similar to red eye. If the illumination source is offset from the optical path, as described for the dark pupil approach, then the pupil appears dark because the retro-reflection from the retina is directed away from the camera. Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright. But bright pupil techniques are not effective for tracking outdoors as extraneous IR sources interfere with monitoring.

Video-based eye trackers typically use these corneal reflection (the first Purkinje image or often referred as glint) and the center of the pupil as features to track over time. A more sensitive type of eye tracker, the Dual-Purkinje eye tracker, can be used for reflections from the front of the cornea (first Purkinje image) and the back of the lens (fourth Purkinje image) as features to track. The fourth Purkinje image is formed by the light reflected from the rear surface of the crystalline lens and refracted by both cornea and lens itself. A still more sensitive method of tracking-can be used with image features from inside the eye, such as the retinal blood vessels, and follow these features as the eye rotates. Different factors can affect the pupil detection during eye tracking and eye trackers using multiple methods, such as dual-Purkinje or both bright and dark pupil methods can be more accurate in calculating the gaze position.

Regarding limbus tracking, the limbus is the boundary between the white sclera and the dark iris of the eye. Because the sclera is (normally) white and the iris is darker, this boundary can easily be optically detected and tracked. The limbus tracking technique is based on the position and shape of the limbus relative to the head. This means that either the head must be held still, or the apparatus must be fixed to the user's head. Due to the occasional covering of the top and bottom of the limbus by the eyelids, it is more helpful for precise horizontal tracking only. The advantages of this technique of pupil tracking over limbus tracking is that the pupil is far less covered by the eyelids than the limbus, and thus vertical tracking can be accomplished in more cases. Also, the border of the pupil is often sharper than that of the limbus, which yields a higher resolution. The disadvantage pupil tracking is that the difference in contrast is lower between the pupil and iris than between the iris and sclera, thus making border detection more difficult In a preferred embodiment, the system is configured to measure an eye parameter selected from bright pupil/dark pupil measurements in combination with Purkinje measurements, including dual Purkinje and/or first Purkinje image measurements.

Artificial neural networks (ANNs) for computation of eye-gaze tracking provides a digitized video image of the user, but this technique is based on a more wide-angled image of the user, so that the entire head is in the field of view of the camera. A stationary light is placed in front of the user, and the system starts by finding the right eye of the user by searching the video image for the reflection of this light-the glint, distinguished by being a small, very bright point surrounded by a darker region. It then extracts a smaller, rectangular part of the video image (typically only 40 by 15 pixels) centered at the glint, and feeds this to an ANN. The output of the ANN is a set of display coordinates. The ANN requires more than the simple calibration that is required by the other techniques; it must be trained by gathering images of the user's eye and head for at least three minutes while the user visually tracks a moving cursor on the display. This is followed by an automatic training session that uses the stored images lasting approximately 30 minutes using the current technology, but then the system should not require re-calibration on the next encounter. To improve the accuracy of an ANN-based system, the corneal/pupil-based calculations can be augmented with a calculation based on the position of the glint in the eye socket. The great advantage of ANN-based techniques is that due to the wide angle of the base image, user head mobility is increased.

Eye movement information from the eye tracker can be typically divided into fixations and saccades, when the eye gaze pauses in a certain position, and when it moves to another position, respectively. The resulting series of fixations and saccades can be called a called a scan path. Most information from the eye can be made available during a fixation, but not during a saccade. The central one or two degrees of the visual angle (the fovea) can provide the bulk of visual information; the input from larger eccentricities (the periphery) is typically less informative and analysis algorithms can be structured accordingly. Hence, the locations of fixations along a scan path show what information loci on the stimulus are processed during an eye tracking session.

Scan paths are useful for analyzing cognitive intent, interest, and salience. Other biological factors (some as simple as gender) may affect the scan path as well. As a participant looks at a page on the internet, the eye-tracking device can focus on the pupil of the user's eye and determine the direction and concentration of the gaze. Heat maps represent where the user concentrated their gaze and how long they gazed at a given point. Generally, a color scale moving from blue to red indicates the duration of focus. Saccade pathways trace the eye's movement between areas of focus.

Another capability of the eye tracking technology is eye movement analysis, which can provide valuable insight into users' overt visual behavior and attention. The most common method for determining the location of a user's observable visual attention is by identifying the fixations and saccades that best indicate where they are focusing on the stimulus in front of them.

Beyond the analysis of visual attention, eye data can be examined to measure fatigue, the cognitive state and workload of a person. Some techniques have been validated in multiple contexts as a reliable indicator of mental effort. Driving a car, reading a magazine, surfing the internet, searching the aisles of a grocery store, playing a video game, watching a movie or looking at pictures on your mobile device are such applications of eye tracking. With very few exceptions, anything with a visual component can be eye tracked.

Image Projection

Eye tracking, video recording, and specifically VOP measurement can be performed using an augmented reality display or holograph imaging in an embodiment. Another embodiment can be comprised of a virtual retinal display (VRD), also known as a retinal scan display (RSD) or retinal projector (RP), is a display technology that draws a raster display, or bitmap, directly onto the retina of the eye. The user sees what appears to be a conventional display floating in space in front of them. However, the portion of the visual area where imagery appears must still intersect with optical elements of the display system. It is not possible to display an image over a solid angle from a point source unless the projection system can bypass the lenses within the eye. In a conventional display a real image is produced. The real image is either viewed directly or, as in the case with most head-mounted displays, projected through an optical system and the resulting virtual image or visual element is viewed. The projection moves the virtual image or visual element to a distance that allows the eye to focus comfortably. No real image is ever produced with the VRD. Rather, an image is formed directly on the retina of the user's eye.

Although the VRD is an output device, the technology lends itself to augmentation with eye tracking or eye gaze systems for input. The VRD system scanning light into only one eye allows images to be laid over one's view of real objects. The VRD system also can show an image in each eye with an enough angle difference to simulate three-dimensional scenes with high fidelity. The eye tracking can enable the fovea on the retina to always maintain good focus ability and as the pupil changes position, eye tracking with movement of the eye follows. It is at the fovea, located in the back of the eye, where sharpest central vision occurs, (also called foveal vision). As the eyes move, the foveation point can also change to achieve better tracking. Using a refractive lens can be used to prevent distortion of eye tracking.

Head Tracking

Head tracking can be performed by using an inertial measurement unit (also called an IMU or 'tracker'). An IMU is an electronic device that measures one or more DOF (such as position, velocity, orientation, and/or gravitational force, as was described previously in this disclosure) by using one or more sensors. Sensors used in IMUs can include one or more accelerometers, gyroscopes, and magnetometers. A MEMS (micro electro-mechanical system) gyroscope, a MEMS accelerometer, and a MEMS magnetometer can be used as complementary and/or redundant sensors to accurately support a full range of motion in a three-dimensional space. Accelerometers work well for measuring five DOF: linear movements in three axes; and absolute tilt about the two axes perpendicular to gravity (i.e., pitch and roll). Accelerometers cannot easily measure rotation about an axis aligned with gravity (i.e., yaw). Magnetometers work well for measuring absolute yaw providing a sixth DOF. Gyroscopes provide a stable way to measure changes the three rotational DOF (pitch, roll, and yaw). Devices that measure these three displacements and measure each of the three rotations in two different ways are typically called nine DOF IMUs. The input signals from the accelerometer(s), magnetometer(s), and gyroscope(s) in these nine DOF IMUs are often processed using a Kalman or a Madgwick filter located in a sensor pre-processing unit to provide output signals that have been optimized for accuracy, stability, and response rate.

The head tracking inertial system can be mounted to the face shield in numerous configurations. Examples include: within the face shield material or display elements, attached to the face shield and configured to communicate with the face shield electronically or wirelessly. When used in AR or mixed platforms, the head tracking technology can normally refresh on-screen images 125-1250 frames per second (or Hz). Higher frame rates reduce movement lag. For specific applications, the refresh rate may be lower than 125 frames per second (fps) or higher than 250 (fps), depending upon the platform used, the application, and type of measurement or testing being performed. For performing some tests, such as the head impulse test a sample rate or refresh rate of 250 Hz or higher might be necessary to capture the subtle eye movements, such as overt and/or covert saccades. Reducing the lag between head movement and the headset response will mitigate symptoms of motion sickness or visually induced motion sickness. The resolution use can be variable depending on the application or platform used but may be chosen as 1080×1200 or 2160×1200-2560×1440 or higher and the latency between images should be short (20 milliseconds or less).

Fourier Analysis

A Fourier transform can be used to convert the relationship between an input (such as head motion) and an output (such as eye movement) in the time domain to a relationship in the frequency domain. By doing this, VOP can be measured for natural motion in a non-clinical environment. As described previously, one of the traditional ways of measuring VOR has been to oscillate a subject's head at a fixed frequency and then to measure how quickly the eyes respond. For this kind of testing, a frequency of 0.5 Hertz would correspond to one cycle every 2 seconds. A cycle corresponds to the combination of one movement to the right and one movement to the left. These movements are typically in the form of a sine wave. The gain at this frequency would be the amount of compensation that the eyes make to the movement of the head. A gain of −1 (also often written as a gain of 1) is perfect because the eyes have rotated exactly the same angle as the head, but in the opposite direction. A gain of −0.75 (often written as 0.75) means that the eyes only compensated for 75% of the head rotation. The phase or phase lag describes how much later the eyes moved than the head. A phase or phase lag of 0 would mean the eyes followed exactly. A phase or phase lag of 45 degrees at a frequency of 0.5 Hertz means that the eyes were delayed by $\frac{1}{8}^{th}$ of 2 seconds (or 250 milliseconds) because 45 degrees corresponds to $\frac{1}{8}^{th}$ of a full 360-degree cycle. To determine gain and phase at a variety of frequencies using the traditional approach of oscillating the head in a clinical environment one would repeat the above test at a variety of frequencies and record the results. This method requires control over each input frequency and measuring the gain and phase of the eye response separately for each frequency, which will not work in a non-clinical setting having natural motion.

A time-varying signal (such as the natural motion of an object in one dimension) can be converted to a series of sine waves. This conversion from a time-varying signal to a series of sine waves is called a Fourier transform. Fourier transforms can be discrete or continuous. A continuous Fourier transform is one in which the time-varying signal is converted to an entire range of frequencies with no gaps between the frequencies. A discrete Fourier transform is one in which the time-varying signal is converted to a specific set of frequencies, such as the series 0.125 Hz, 0.25 Hz, 0.5 Hz, 1.0 Hz, and 2.0 Hz. Discrete Fourier transforms are easier to calculate using digital electronics. By converting the observed natural yaw of the head as a function of time using a Fourier transform, one can generate a graph showing the amplitude of the input signal that the eyes would need to compensate for in order to follow a stationary image or visual element. By converting the sensed horizontal movement of the eyes at this same time using a Fourier transform, one can generate a second graph showing the amplitude of the eye signal that compensates for the head movement. By comparing these two graphs mathematically, it is possible to determine gain at various frequencies directly from the natural head yaw movement. Similar mathematical calculations can be made to determine phase. The same method can be used to determine gain and phase in other dimensions such as pitch of the head versus the sensed vertical movement of the eyes, etc. Discrete Fourier transform calculations of this type can be performed by a microprocessor that receives the time-varying orientation signals from a head orientation sensor and the time-varying signals from an eye orientation sensor using mathematical calculations capable of being understood by anyone skilled in the art.

Further Embodiments

Embodiments of this invention can also use sensing elements/transducers on the innermost layer of the helmet, adjacent to the scalp, to more accurately measure information regarding violent impacts to the head (such as linear and rotational acceleration data).

In another embodiment, to enhance the safety of the wearer, following occurrences of violent blows to the head, the measured physical aspects of the impact data can be displayed to an observer and/or provide a local, adjacent or remote response, alert or warning. This response to an abnormal impact value can be in the form of an optically perceptible response, such as photofluoresence, or can be a haptic, vibratory, or an acoustic response either to the user and/or the device of the observer. In an embodiment, the helmet or specific portion of the helmet may change colors, emit a light, display or generate another signal response when a user receives a critical impact to the head, exhibits abnormal oculomotor findings, reaches an abnormal physiological or biochemical pre-determined value. In another embodiment, adjacent clothing may change color when the abnormal values have been reached. Where desired, the impact sensing element/transducer data can be used to activate an associated intervention system, human or automated, to prevent injury to the user. As an example, flexible sensing elements/transducers within the helmet layers can detect a mechanical stimulus (e.g., compressions or blows) and emit mechanoluminescence or triboluminescence (e.g., light emissions) when a preset abnormally harmful impact value is reached, which can be visualized by observers. This visual response to a violent impact to the head which has exceeded a specific preset threshold value, or abnormal physiologic or biochemical value can also include other responses including but not limited to: flexible terahertz imagers with tunable multi-arrayed carbon nanotube materials or other photonic devices. This can include Internet-of-Things (IoT) sensing element/transducer applications, which can connect the sensing system of the device or components of the device to the internet.

In another embodiment, at least one impact sensor can also be configured on the face shield in one or more specific locations to detect both linear and rotational or tangential impacts.

In an embodiment, the present invention is comprised of an ocular performance measuring system with head tracking and ocular-based sensors integrated into a face shield. The system described is configured for measuring eye muscle movement responses and/or eye reflexes and is comprised of at least one eye sensor, a head orientation sensor and electronic circuit. This system is responsive to a human generated input signal from the group of but not limited to an auditory human input signal, a haptic human input signal, a manual input signal. In another embodiment, the system can also be responsive to input signals including a remote input signal, external wireless signal, accelerometer-based measures with pre-set impact thresholds, a digital auditory input signal, a digital haptic input signal, human eye muscle movement, head/eye/or other body movement, or a human gesture. As an example, a bone conducting sensor incorporated in the framework can provide auditory/acoustic signals to issue an input signal to a controller to operate the camera system. The controller could communicate with other parts of the system to support the commands.

In an embodiment of the device, the system may include the user interface for providing information to the wearer or receiving input from the wearer. The user interface may be associated with displayed images, a touchpad, a keypad, multiple cameras, buttons, a microphone, a haptic device, and/or other peripheral input devices. The processor may control functions of the system based on input received through the user interface. The system and/or testing function controls and input connections can be in a head-worn device and/or in a remote device. The computing system could be a distributed computing system. The computing system could comprise cloud computing.

In an embodiment of the device, one or more of the described functions or components of the system may be separated into additional functional or physical components or combined into fewer functional or physical components. For example, the infrared camera may be mounted on a helmet or wearer separate from the system. Thus, the system may be part of a portable/wearable computing device in the form of separate devices that can be worn on or carried by the wearer. Separate components that make up the wearable computing device may be communicatively coupled in either a wired or a wireless fashion. In some further examples, additional functional and/or physical components may be added.

In an embodiment, the face shield system can include a gyroscope, a global positioning system (GPS), magnetometer, and an accelerometer. The face shield display tracking system may be configured to provide information associated with a position and an orientation to the processor. The gyroscope may include a micro-electromechanical system (MEMS) gyroscope or a fiber optic gyroscope as examples. The gyroscope may be configured to provide orientation information to the processor. The GPS unit can include a receiver that obtains clock and other signals from GPS satellites. The GPS unit can be configured to provide real-time location information to the processor. The face shield system may further include an accelerometer configured to provide motion input data to the processor.

In one embodiment, the face shield system is comprised of an eye-tracking and measuring sensor, a head motion sensor and compares the gain and phase of each (e.g., an electronic circuit generates a comparison of the three axes from the head orientation sensing element with eye movement signals from the eye sensor to calculate a gain and phase of the eye movement response to head rotation, in the opposite direction). The eye orientation sensor senses vertical movement and horizontal movement of at least one eye. A visual target is provided in the display. The device or method can present this visual target to one eye (monocular) or both eyes (binocular). A power source can be attached to the face shield and can be rechargeable by a wireless interface.

In an embodiment, the face shield device can measure the relationship between motion of the head in this environment and VOP being tested. The data acquired can be uploaded to a remote position from the user for display and interpretation or transmitted wirelessly to a smart phone, wearable display device, other hand-held device or other computer source. The head orientation sensor senses pitch and yaw of the person's head in a range of frequencies that comprises at least one frequency greater than 0.01 Hertz and less than 15 Hertz. The head orientation sensor can comprise an IMU. The head orientation sensor can comprise one or more accelerometer(s), magnetometer(s), and/or gyroscopes.

In another embodiment, the face shield display system can include an eye tracking and measuring system, a connected head mounted display tracking and measuring system, an optical system, peripherals, a power supply, a micro-processor, a memory, and a user interface. Components of the system may be configured to work in an interconnected fashion with each other and/or with other components coupled to respective systems. For example, the power supply may provide power to all the components of the system. The processor may receive information from and control the eye tracking system; the head mounted tracking system, the optical system, and peripherals. The processor may be configured to execute program instructions stored in the memory unit and to generate a display of images on the user interface. The display to the user can be presented as a 2D or 3D (3 dimensional) virtual display.

In another embodiment, the face shield is attached to a helmet and has an aperture allowing the user to visualize the surrounding natural environment or scene. The structural elements can be rigid to protect the face and others may have some flexibility components to help mitigate the impacts to the facial structure. Although the face shield is firmly attached to the helmet, in another embodiment, the face shield can be attached to an adjustable interface, between the face shield and helmet. This would allow the face shield to be used with different helmets or head worn devices.

Embodiments of the invention could be ocular sensor-based modules that are attached to a face shield or other device of any configuration. Such ocular-sensor-based modules could also be attached directly to a head without using an intermediate device. The ocular sensor-based modules can also be comprised of a hand-held device, such as a smart phone, programmed for measuring ocular parameters for the use discussed in this document.

In another embodiment, the ocular sensor-based modules can be located within the face shield or attached in a manner to track and measure the eye movements easily and accurately. The head tracking sensor can also be attached to the face shield.

In another embodiment, the face shield system can have a manual control operating switch with an active and inactive mode. It can provide real-time feedback on the display screen, has the capability to display time and can be adjusted to fit users of different statures. It is comprised of eye sensors, a head orientation sensor, an electronic circuit comprising a central processing unit with memory unit and a display system which can project visual elements for the user to focus upon for measuring various ocular parameters. It can also comprise an auditory input for testing instruction, signaling randomized head movement and serving as an auditory distractor for some visual cognitive tests. Collected data can be transmitted to a small Droid-like hand-held device where easily understandable results can be seen.

In the embodiments discussed herein, a forward-facing camera, forward-facing visual cue projector eye, eye tracking sensors and head tracking sensors and components of the electronic circuit can be activated or controlled haptically, auditorily, remotely, wirelessly, with gestures or movement of the eyes, head, hands or manually with a power switch on the face shield. Alternatively, the system can have a local/sideline mode (e.g., where the device remains on for testing while the player is off the field) and a field mode (e.g., where the device is listening for pre-define triggers alerts, at which time it will be turned on for measurement of ocular parameters).

In embodiments of the invention, the optical system can include components configured to provide images to a viewing location (e.g., eye of the wearer.) The components may include a display pane, a display light source, and optics, such as mirrors or refractive lenses. These components may be optically and/or electrically-coupled or connected to one another and may be configured to provide viewable images at a viewing location. One or two optical systems may be provided in the system. In other words, the face shield display may allow the wearer to view images in one or both eyes, as provided by one or more optical systems. Also, the optical system(s) may include a transparent or translucent display connected to the display panel, which may allow a view of the real-world environment while providing superimposed virtual images. The infrared camera or video camera, using visible light, coupled to the eye tracking system may be integrated into the optical system with a data storage and logging recorder.

In another embodiment, the eye tracking system can include a camera attached to or incorporated in the face shield that is positioned in front of the eye of a user. In another embodiment, an array of optical detection elements can be placed directly onto the surface, or within the face shield lens located in front of an eye.

In an embodiment, the eye-imaging camera or video camera elements can be comprised within the face shield material (either in the center of the visual field or off axis of the center of the visual field), on the framework around the face shield or attached to the face shield and can capture the image of the eye through reflection off of the lens. In order to properly capture the eye image through reflection off of lens, there must be sufficient clearance between the user's face and the lens surface to avoid the obstruction of the eye image by user's face or the imaging optics.

In another embodiment, two or more eye image sensors are configured in a complementary fashion to increase sensor accuracy. Image sensors can be configured from the following group: image sensors of the same type across different focal lengths, image sensors of the same type across different angular locations and/or image sensors of differing types to provide composite images.

In another embodiment, the eye sensor(s) is/are attached to or mounted within the structural member(s) of the face shield. At least one of the eye sensors is positioned at a sight plane below the inferior margin of the upper eyelid. It is below the upper eyelid in order to more easily visualize the pupil, cornea, iris or other features of the eye used for eye tracking. Above this plane of sight, the eye sensor would have difficulty tracking the eye muscle movements, due to obstruction of the upper lid and eyelashes.

In an embodiment, the human ocular performance measuring system is comprised of eye sensors, attached to the face shield unit, and configured to measure eye muscle movement responses using different techniques of eye sensor measurement including, but not limited to use of one or multiple cameras, or simultaneous use of different types of cameras for eye tracking. In another embodiment, at least one eye sensor can track one or more different locations simultaneously on the surface of one or both eyes (e.g., cornea, pupil, limbus, sclera) or image features from the retina. In an embodiment, the head orientation sensor comprises the same video camera as the eye sensor. In another embodiment, the eye sensor(s) measure more than one corneal reflection or other eye feature using one or more different types of illumination sources simultaneously. In one embodiment, different types of illumination sources can also alternate or combine the type of illumination, depending on the light needed.

In another embodiment, eye sensors, attached to the face shield unit can be located in different positions to acquire different focal points of the eyeball, to achieve more accuracy with eye tracking. Eye sensors can also be configured to merge eye movement responses from different image sensors for more accurate measurement. For example, an eye sensor tracking the bright pupil can be merged with the same sensor, or another eye sensor, attached to different location on the face shield, which is tracking the dark pupil response. In another example, an eye sensor tracking the dark pupil can be merged with the same or different sensor which is tracking the limbus. The merged data can provide more information regarding gaze and eye muscle movement responses. In embodiments described, eye sensors can have multiple functions which enable different measurement or features of the eyeball.

In one embodiment, a single camera system is used for the eye tracking. In another embodiment, a multi-camera system is used and the cameras can be located in the lens, framework or eye or head worn device and can be located in different sight planes or at different distances from the measured area of the eye or in a device attached to the face shield, such as an iPhone or other electronic device remotely located. The camera can have a resolution of at least five megapixels and could be capable of recording at 720p or 1080p resolutions. The camera could have a microphone for voice commands, and at least 12 GB of usable storage. The camera could support Bluetooth and/or Wi-Fi. The camera could be part of, or work with an Android or iOS smartphone. The camera can have in excess of 25° field of view. The camera system could also comprise an onboard OMAP (Open Multimedia Applications Platform) processor running the Android or iOS operating system. In another embodiment, the entire system could be a smartphone that includes an embedded eye camera sensor with a head motion sensor. Providing direct image overlay over the wearer's main line-of-sight, coupled with the motion sensors and camera, it can enable true augmented reality capability. A smartphone or similar device (such as a tablet computer) could also be used to provide wireless remote control.

Another embodiment of the face shield system described involves dynamic control of the frame rate (i.e., number of images acquired per unit of time) of the one or more cameras that view regions of one or both eyes. Camera frame rate is a major determinant of the ability to determine and measure rates and directions of movement (i.e., velocities) of objects within images of an eye. The muscles within the eye are capable of movements that are the most rapid of all muscles within the human body. Thus, increased camera frame rate can be critical in some cases to more accurately and robustly measure dynamic movements of an eye and/or its components.

Embodiments of the invention can use miniature video cameras. The image of the eye can be tracked and allow the person's horizontal, vertical, and/or torsional (rotary) vestibulo-ocular responses to be measured. A moving visual target or visual element can provide a method for tracking, for optokinetic (OPK) testing, for saccade detection and measurement, for gaze fixation testing, for DVA measurement and for VOR testing. In the Active Head Rotation (AHR) horizontal test, the subject moves their head left and right randomly to the auditory signal and visual presentation. The speed of the signals increases through 1 Hz up to a maximum of at least 5-6 Hz. The person will attempt to keep moving the head back and forth at the speed of the beeps. For AHR Vertical, this test is conducted in the same manner as the horizontal test above, except that the head motion is up and down rather than left and right In further embodiments, the system can include at least one digital camera trained on the person's eyes and which the camera can have auto-tracking. The camera may allow for digital centering of the person's pupil at least in one direction through concentrating on the region of interest and can be in multiple directions. The use of digital centering eliminates the need for a mechanical adjustment mechanism in the given direction.

In another embodiment, the eye sensor can be comprised of an array of transparent light detectors based on graphene. In another embodiment, the system can include an illuminator that is configured to provide illumination in a visible, LED or infrared light spectral band for the eye sensor to capture the 3D image of the iris. In further embodiments, the eye sensor can be a microlens array light field camera (LFC) or plenoptic camera. In another embodiment, a hologram can be used to blend the digital world with the real world in the attached AR system, to aid in the testing and measurement of the eye movement. This can enable a more immersive see-through multi-dimensional method for all of the visual or oculomotor tests described in this disclosure.

In embodiments of the invention, the light source can be infrared, near infrared, and/or visible light, such as LED, can be directed toward one or both eyes. The camera can be used to track the reflection of the light source and visible ocular features such as the pupil features, cornea reflection features, iris registration features, limbus features or retinal data imaging. The collected data from the eye tracking system can be used to measure the movement features of the eyes or eyelids or rotation of the eye, acceleration/velocity of the eye movement, duration of the eyelid closure, rate of the eyelid closure and the direction of gaze. Additional information such as blink frequency and changes in pupil diameter can also be detected by the eye tracker. Aggregated eye tracker data can be written to a file for later analysis. Stored eye tracker data can be used to analyze the visual path across an interface such as a computer screen. In this case, each eye data observation is translated into a set of pixel coordinates. From there, the presence or absence of collected eye data points in different screen areas can be examined. This type of analysis is used to determine which features are seen, when a particular feature captures attention, how quickly the eye moves, what content is overlooked and virtually any other gaze-related data. Eye position is extracted from video images and graphics are often generated to visualize the findings. Beyond the analysis of visual attention, stored eye data can be examined to measure the cognitive state, fatigue, alertness or other information.

In other embodiments of the present invention, two or more of the single prism beam splitters can be combined to form compound beam splitters that split a single beam of light into three or more different beams of light. A beam splitter can have an optical multi-layer thin film, formed by laminating numerous layers in sequence. The numerous laminated layers can each be comprised of having a different refractive index.

In other embodiment multiple prisms can be used which can use a corrective optical element to eliminate any deviation or aberrations in the see-though viewing path, such that a user of the device can comfortably see through the eye-tracker normally. For example, in one of its aspects, the invention may include a wedge prism having only planar surfaces. This prism acts as a light guide to supply illumination light to the eye, as well as providing imaging light to the camera from the illuminated eye. In this embodiment a complementary prism can be arranged with respect to the thin prism such that the two prisms appear to the eye as a plane-parallel plate, or as a weakly powered optic.

In an alternative embodiment, an eye-tracker can use a free-form prism between the eye and a sensor. The freeform prism includes one or more surfaces with optical power, which are used both for imaging of the eye onto the sensor, and for optical aberration control. In certain embodiments, the freeform prism is used in conjunction with, or exclusive of, additional focusing optics such as a camera In other embodiments, the head tracking can be done from sensors in a hand-held smart phone, smart pad, from another sensor system attached to a body part, or from a remote device viewed by the user.

In another embodiment, the face shield with eye camera attached to the helmet covering the head is configured for measuring and correcting slippage offsets. The measurement and correction of slippage offsets is carried out by one or more sensor selected from the group of: the existing multi-axis IMU, the existing imaging sensor, an additional IMU, and a wider field of view image sensor.

In one embodiment, the device can be calibrated before it is used. Calibration can be performed by focusing on a distant target, such as a laser light which is projected to the wall, or a holographic image projected from an embedded AR display. The image or visual element moves horizontally, vertically and then is center located. Typically, several trials are performed to establish reproducible results. During this test, the person is instructed to rotate the head from side to side horizontally or vertically to an auditory cue at frequencies ranging from 2 to 6 Hz. Eye movements are recorded including: direction, amplitude, and velocity of eye movements. Head inertial movements are recorded by the velocity rate sensor attached to the head. Tracking eye movement from spot to spot in this way is called "active tracking". Testing of this type allows gain, phase, and asymmetry to be measured separately at each frequency. In another embodiment, which is a more sophisticated approach would be to ask the subject to follow an object that is not necessarily moving at one specific frequency, but at a combination of frequencies ("natural tracking") and then using a Fourier transform to convolve the gain, phase, and asymmetry at various frequencies directly from the complex waveform that was being followed by the subject. Natural test method testing in the horizontal plane could utilize focusing on a target moving across the horizontal visual field. Watching a moving object ascend and descend in the air can serve as a natural vertical test.

Any combination of the discussed embodiments of head inertial trackers and eye tracking systems can be used to measure the ocular muscle movement or reflex response with head movement. Alternatively, in another embodiment, the visualized target required to focus upon for the ocular parameter being tested may be displayed, in the natural environment, as an AR, 3D image, hologram or some other light source image from the attached display screen. Video camera eye orientation tracking, using invisible or visible light, simultaneously can be used with head tracking. As the head moves, the ocular responses can be tracked and measured by a variety of modalities. A Fourier transform can be used to compares the inertial head movement and eye movement response at various frequencies in a complex waveform and software can analyze the data. The stored data can be displayed remotely and abnormalities of the related ocular response to the head movement can then predict the performance of the user when performing an occupational activity.

Embodiments of the invention can incorporate other impact mitigation elements and sensing elements/transducers for detecting any abnormal physiological or biochemical properties of the user.

Sensors within the helmet, should be strategically placed, based on the position of human anatomical structures and the parameter they were designed to detect and measure. As an example, when measuring the pulse rate or blood pressure the sensing elements/transducer are not positioned randomly but placed over a major artery (such as superficial temporal or occipital artery). Among many bodily fluids, sweat provides a significant amount of information about a person's health status and is readily accessible, making it suitable for wearable, noninvasive biosensing. Sweat contains important electrolytes, metabolites, amino acids, proteins and hormones, which allows monitoring of metabolic diseases, physiological conditions, or a person's intoxication level. Some areas of the body have a higher concentration of eccrine sweat glands (e.g., the major sweat glands, which are sometimes called merocrine glands which open directly onto the skin surface), such as on the forehead. Eccrine glands secrete a sterile, dilute electrolyte solution with primary components of bicarbonate, potassium, and sodium chloride, glucose, pyruvate, lactate, cytokines, hormones such as cortisol and immunoglobulins. It has the same components as plasma but in a more dilute concentration. Stress plays an important role in the overall health of a person, when under stress, the adrenal gland releases cortisol and adrenaline into the bloodstream. Cortisol can be detected in the sweat. Increased levels of cortisol have a detrimental effect on the regulation of physiological processes such as blood pressure glucose levels, and carbohydrate metabolism.

In the following embodiment of the inventions discussed herein, sensors or sensing elements/transducers, used to detect and measure physiologic or biochemical properties of the user, can be anatomically positioned for the physiologic or biochemical parameter measures for the intended design of the sensor and placed adjacent to the skin. For example, sensors to measure pulse rate, blood pressure and oxygen saturation are placed over arteries. Sensors measuring chemicals or specific hormones, such as sodium (for measuring hydration) or cortisol (for measuring stress) can be placed over areas of large concentration of sweat glands, such as on the forehead or temporal area. These sensors or sensing elements/transducers can detect abnormal physiologic measures not limited to but including: arterial pressure (which is exerted by the blood upon the walls of the blood vessel, and varies with the muscular efficiency of the heart, blood volume, viscosity, age, health of the individual, and the state of the vascular wall), hypotension (defined as systolic arterial pressure less than 100 mm of mercury), hypertension (defined as systolic arterial pressure 140 mm of mercury or greater); thermal changes including hypothermia (below 95 degrees) and hyperthermia or hyperpyrexia (significantly above 98.6 F), changes in cardiac activity including bradycardia (below 60 bpm), and tachycardia (above 100 bpm at rest), arrythmia (irregular rhythm), atrial fibrillation, atrial flutter, cardiac arrest, rate of inhalation and expiration as well as the ocular parameters discussed previously. As noted above, the sensing elements/transducers over the head would be positioned over the temporalis region, just anterior and superior to the tragus and pinna to measure the superficial temporal systolic arterial pressure exerted by the blood upon the walls of the blood vessel or pulse rate and the abnormal changes in cardiac activity. Sensing elements/transducers for measuring abnormal thermal changes of wearer would be located over the temporal skin, as measurements are closer to true (core) body thermal value.

In another embodiment, the sensing elements/transducers can also detect and measure any abnormal changes in cranial, motor or sensory function, mental status, nervous system status, non-focal and focal neurologic changes, conscious intellectual activity, and specifically any abnormal measurement of cerebration, abnormal waveform frequency of the cerebral cortex, spike analysis, electrophysiologic measurement of cerebral activity with sensing elements/transducers in contact with the scalp or using evoked Potentials (EP) to detect and measure topographic cerebral mapping. Specifically, abnormal waveform patterns associated with concussions can be detected and measured including: a decrease in alpha and beta relative power & mean frequencies, increase in temporal lobe slowing (Delta, Theta or Alpha); significant Alpha Asymmetries; significant coherence and/or phase issues either hypo or hyper with phase lag usually being slower; temporal lobe or all frontal lobe or front/back issues; excessive Delta and Theta (associated with recent injury); more power in faster Alpha bands, 10-11 Hz (consistent with an older injury) or evidence of epilepsy. The sensing elements/transducers for measurement also requires strategic placement and accuracy is dependent on the number of sensing elements. Conventionally 21 electrodes may be used over specific scalp locations, and dense array with 32-64 miniature sensors can provide a more accurate map of scalp voltage distribution than the conventional array.

In another embodiment, the sensing elements/transducers can detect abnormal biochemical measures not limited to but including simple monosaccharides (sugar) or dextrose, metabolites, proteins, electrolyte abnormalities including detection and measurement of hypokalemia (below 3.5 mM) and hyperkalemia (above 5.5 mmol/L), hyponatremia (below 135 mmol/L), hypernatremia (above 145 mmol/L), acidosis, alkalosis, osmolality, cortisol level, and evidence of depletion of body fluids/hypohydration.

Sensing elements/transducers can detect and measure chloride, including hyperchloremia (above 110 mEq/L), hypochloremia (below 98 mEq/L), amount of oxygen bound to hemoglobin in the blood, expressed as a percentage of the maximal binding capacity, including hypoxia, hypoxemia (e.g., low partial pressure of oxygen in the arterial blood with less than 90 percent), hyperventilation/tachypnea, which can result in hypocapnia; hypoventilation, hypopnea, bradypnea; hypocapnia (less than 35 mHg for partial CO2 pressure); hypercapnia (blood CO2 level over 45 mmHg) or ventilatory failure. The sensing elements/transducers can also detect volatile organic compounds through skin sensing elements/transducers or different gases/organic molecules as a biomarker for human detection. In another embodiment the eye sensor/video camera can detect retinal vessels and measure O2 saturation, pulse, EKG. Any abnormalities of these physiologic properties described can be logged and transmitted remotely.

In another embodiment, this sensing element/transducer can be specifically placed on the buccal side of a dental structure, in contact with buccal mucosa, as it is a source of bodily fluids) for: chemical/biochemical analysis (e.g., Sodium/potassium/glucose/cortisol/proteins/electrolytes/hydration status) as well as identity information of an individual. These sensing elements/transducers can communicate with other sensors within the helmet system in such a way that if any abnormal physiologic or biochemical parameter is detected, a transdermal drug can be released to permeate across the skin to treat the abnormal condition.

In another-embodiment, other sensing elements/transducers in the helmet system can also communicate with other sensing elements/transducers in such a way that if any abnormal physiologic or biochemical parameter is detected, a transdermal drug can be released to permeate across the skin to treat the abnormal condition.

In another embodiment, these sensing elements/transducers can be implantable for measuring physiologic, chemical or biochemical abnormalities and abnormal parameters can communicate with other worn sensor elements and data can be transmitted remotely. Any of the sensors or sensing elements/transducers listed here, or others capable of being understood by anyone skilled in the art may also provide a user with information about his or her own biometric data changes.

In an embodiment of the face shield described herein, the head tracking sensor and eye sensor can be configured to use such a sensor fusion algorithm to provide more accurate information regarding measurement of eye fixation with head movement. Alternatively, different eye sensors measuring eye features at different points can be configured for sensor fusion to obtain more accurate data regarding the eye muscle movement responses. The sensors can be of the same type (such as cameras for a stereoscopic image) or of differing types (such as combining accelerometer and gyroscopic data in a Kalman Filter). They can also be complementary (independent sensors measuring different properties combined to give a more complete view), competitive (independent sensors measuring the same property for fault tolerance or redundancy), or cooperative (using multiple sensor measures to derive information not available to any single sensor).

In another embodiment a camera and machine learning in conjunction with computer vision can be used to measure the ocular parameters discussed without the aid of infra-red lights.

In another embodiments, a computer learning process can detect and measure any of the described ocular parameters in this document and provide classification of raw gaze data, belonging to fixations, saccades, or other eye muscle movement or eye reflex responses. The eye tracking sensor and/or head tracking sensor can be configured for use with a classifier to train the classifier to detect any abnormal parameter measured, transmit this information remotely and provide visual a visual rehabilitation program to specifically address the abnormality detected.

In an alternative embodiment, the present invention not only measures VOP (such as the VOR or DVA with head movement), but also can visually rehabilitates/retrain the user when a specific ocular parameter abnormality is present, to enhance the parameter visual accuracy with specific visual stimulation and head movements. This can be used to help a person improve his or her balance by challenging, exercising, enhancing, and/or retraining the VOR (fixation/refixation) used during activities in daily living, routine exercise, and high level athletic/vocational activities and therefore improving the DVA and accuracy of the fovea to remain fixed on the visual element. This visual rehabilitation can be done for specific vestibulo-ocular pathologic findings. As an example, when there is an abnormal VOR in the horizontal plane, specific algorithms of eye fixation on a target object, while the head is moving horizontally can be used to visually rehabilitate the abnormality. When the abnormal VOR is seen in the vertical plane, specific algorithms of eye fixation on a target object, while the head is moving in a vertical manner can be used to visually rehabilitate the abnormality.

Other embodiments of the face shield with use of visual displays can provide an effective method for any detected eye muscle movement deficits and cognitive rehabilitation therapy. Effective cognitive rehabilitation interventions initiated early after a TBI has been shown to enhance the recovery process and minimize the functional disability. The return of normal ocular parameters can provide a precise risk assessment to guide the determination for return to deployment (RTD) or return to play activities with high performance predictability. Tracking, analyzing and monitoring the eye movement measurements with rehabilitation can provide a key strategy to the decision timing for extraction from the field or operative environment to return to the user's previous activities, based on the ability for the return of measured eye movement responses to achieve normal values.

In another embodiment, an interactive ocular parameter program can be provided that uses image-based interactivities for testing and management of concussions/traumatic brain injury with periodic assessment to analyze the progress of cognitive deficits. A cognitive rehabilitative program can be used with specific identified cognitive conditions. The cognitive testing can also be used for assessing the neurologic status, alertness, fatigability, return to play readiness, situational awareness, unhealthy status, predicting human performance, stress and managing any deficits detected with a visually interactive cognitive program designed to correct those deficits.

In another embodiment, an interactive ocular parameter program can be provided that uses image-based interactivities for testing and management of concussions/traumatic brain injury with periodic assessment to analyze the progress of cognitive deficits. A cognitive rehabilitative program can be used with specific identified cognitive conditions. The cognitive testing can also be used for assessing the neurologic status, alertness, fatigability, deployment readiness, situational awareness, unhealthy status, predicting human performance, stress and managing any deficits detected with a visually interactive cognitive program designed to correct those deficits.

In an embodiment, eye-tracking sensors, measuring ocular parameters including visual search, navigation, memory and attention can be used to provide an objective and qualitative measure of the initial perception component of situational awareness. As it encapsulates awareness of one's immediate surroundings, their context, meaning, and the possible progression of events, and is a cognitive process that involves In another embodiment, this face shield technology can be used in gaming activities where multi-use players rely on visual accuracy to compete against each other in the game in which they are engaged.

In another application embodiment, the face shield system can be used for gambling sports, fantasy football as well as other fantasy sports. The ocular performance measures discussed herein can provide information about user's health condition, including concussion, traumatic brain injury, neurologic status, cognition, fatigue, alertness, impairments and/or oculomotor parameter measurements to participants viewing the data transmitted. Information acquired from the face shield system can be transmitted to a mobile device, computer, or other electronic device in a variety of communication methods including a dedicated SMS text service. Users of the devices can track athlete injuries, measure and/or predict human performance of the athlete or team using the face shield system. This data received can be used for draft assistance, measurement of play performance, predictions, injury assessments and as a measure for duration of play.

In another embodiment of the face shield system, the detection of abnormal ocular parameter and/or abnormal physiological parameter data can be configured to be transmitted to computer controller systems of vehicles or other devices. Reception of this abnormal sensing data can control the operating systems of vehicles or devices, through AI and/or machine learning.

In another embodiment, other protection systems such as a window shield, attached to a vehicle, can be comprised of eye tracking sensors within the window shield which can detect abnormal ocular parameters. If an abnormality is detected and measured, the data can be transmitted to the control operating system of the vehicle through AI and/or machine learning. The eye tracking sensors can be fixed in a position within the window shield for eye tracking or alternatively the eye tracking sensors, after "locking on the eyes" with starting the vehicle, can continuously move to different locations to maintain the locked tracking feature of ocular parameters, while the vehicle is being operated by the user.

Embodiments of the inventions described herein can provide supernormal enhancement of these same systems where no balance disorder exists, as in the case for enhancement of athletic and vocational abilities. Embodiments can enable individuals to reach a higher level of performance in their occupation, enable them to have increased ocular performance functions when participating in their usual occupational or play activities as well as enabling cognitive training and rehabilitation. Such an enhancement methodology can be used in athletic/vocational enhancement or training.

In an embodiment, this face shield device can function as a provider extender and potentially mitigate the long-term physical and psychological sequelae of traumatic brain injuries by delivery of early visual rehabilitation. This device can provide a portable and novel augmented reality eye worn device to rapidly and accurately provide optimal triage and early intervention with effective treatment as long as required for users subjected to head trauma. It can transmit the collected head sensor and eye camera data information to Droid-type hand-held device remotely and to the injured user and can provide a key treatment method of early visual rehabilitation, provide a more accurate strategy to guide return to previous activities decision making. Because measured ocular parameters, such as the VOR, can also be adversely affected by fatigue and alertness, both also a sequalae of concussions, this can provide a measure of potential performance ability.

The data obtained from the devices and methods described here can be used for wireless communications. The data can be embedded GIS or geographic information system of the eyes or a digital map of where the eyes are located relative to the head movement.

In another embodiment, the face shield system can be integrated with wireless systems and software, allowing the collection and analyzing of real-world eye tracking data from athletes, on the field playing a sport, from military personnel in an operative environment or from law enforcement users in other locations. Mobile data logging allows the physiology data to be collected. Eye tracking metrics can also include gaze path, pupil diameter, blink frequency, heat map, areas of interest (AOI), moving areas of interest, fixations, fixations sequence, and dwells.

In an alternative embodiment, the system can be tethered to smart phone or computer and use their display or push response to these devices Embodiments described herein can be used with a protective sport helmet including those designed for football, lacrosse, hockey, multi-sport, horse-back riding, cycling, motor-cross, whitewater, climbing, and baseball helmets. Various embodiments can also be used for safety helmets, such as construction or industrial helmets, and helmets used by law enforcement, security and/or military forces.

Areas of Application

Embodiments of the systems and methods described herein could be used in a variety of areas, including but not limited to the military, law enforcement, sports, medical, and commercial businesses. Eye movement, eye position, visual acuity, pupil function, peripheral and central vision testing can all be easily performed with this technology in these platform systems. These eye activities can be correlated with movement of the extremities to assess hand eye coordination.

Sports. Embodiments of the present invention, using ocular performance measurements, can be used in sports/athletic environments where ocular parameter measurement can help predict player performance, player fatigue and early detection of abnormalities such as concussions and traumatic brain injury. Additionally, if an athlete had such an abnormality and could be given some rehabilitation methods prior to play, this could correct the abnormality and increase performance in that activity. Embodiments of the present invention can be an accurate method to determine when the athlete is ready to return to play activities, based on improvement of the VOR or DVA. It therefore can be utilized in TBI/concussion evaluation/assessment and management for return to play. Some ocular performance measurements, including VOR, can also be adversely affected by alcohol and drug use. Potential use of this testing can also provide a drug screen for those individuals suspected of having suboptimal performance.

Military personnel functioning in a high-level environment and requiring target fixation of their eyes, while performing other activities such as with head or body movement, require a normal VOR and normal DVA. If the VOR/DVA is abnormal, the individual will not demonstrate peak human performance. Embodiments of the present invention can be used by the military in places such as the pilot selection process or special operations community to aid in the selection of individuals without a VOR/DVA abnormality. VOP measurement could enable other individuals, who had normal foveal fixation ability to be chosen for a particular task that has better predictable performance for a particular duty of the day.

Medical. Similarly, any person with a motion sensitivity disorder (such as motion sickness, vection induced motion sickness, or visually induced motion sickness) or a balance problem, either of a central or peripheral origin, will have a VOR/DVA abnormality. Individuals with such an abnormality will express symptoms of dizziness, disorientation, difficulty with focusing, nausea, fuzziness, and such other complaints as not being clear headed. Embodiments of the present invention can be useful to people who have experienced a vestibular insult, vestibular dysfunction or labyrinthine dysfunction. It also can be utilized other centers which perform vestibular rehabilitation and athletic/vocational enhancement environments. Embodiments can be used as an objective tool for assisting in the diagnosis of traumatic brain injury (TBI), concussion and other degenerative cerebellar disorders that cause highly abnormal results.

Commercial. Embodiments can also be used in other industries where individuals are expected to perform in high activity levels, or provocative environments.

Vestibular Rehabilitation. VOR scoring can also be beneficial in determining who is likely to benefit with vestibular rehabilitation therapy. VOR scoring can also be used more objectively in determining the benefit or improvement with such therapy. Although vestibular rehabilitation therapy can improve the ocular responses, this scoring can accurately quantify the improvement and more ably predict who is able to return to their normal activity without loss of human performance. Having a VOP score can also provide feedback that helps to control abnormal VOR responses. When an ocular response is abnormal with head rotation (a VOR abnormality, for example), such a finding can also determine a need for improvement with rehabilitation. Repetitive head movement in the abnormal plane of rotation, while the eye remains fixed on a target of interest, can provide a means for improving or enhancing the VOR or other eye responses.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

A number of variations and modifications of the disclosed embodiments can also be used. The principles described here can also be used for applications other than sports. While the principles of the disclosure have been described above in connection with specific apparatuses and methods, it is to be clearly understood that this description is made only by way of example and not as limitation on the scope of the disclosure.

What is claimed is:

1. A human ocular parameter measuring device wherein:
the device is configured for measuring an ocular parameter selected from the group of:
vestibulo-ocular reflex;
ocular saccades;
pupillometry;
pursuit tracking during visual pursuit;
vergence;
eye closure;
focused position of the eyes;
dynamic visual acuity;
kinetic visual acuity;
virtual retinal stability;
retinal image stability;
foveal fixation stability; and
nystagmus; and
the device comprises a face shield, configured to be worn by a human, and the face shield comprises:
an eye sensor wherein:
the eye sensor is configured for eye tracking; and
the eye sensor senses eye information selected from the group of:
horizontal eye movement;
vertical eye movement;
pupil size; and
eyelid movement;
a head orientation sensor wherein:
the head orientation sensor senses a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
an electronic circuit, wherein:
the electronic circuit comprises a central processing unit, and a memory unit;
the electronic circuit is responsive to the eye movement information received from the eye sensor; and
the electronic circuit is responsive to head movement information received from the head orientation sensor.

2. The device of claim 1 wherein:
the device measures vestibulo-ocular reflex.

3. The device of claim 1 wherein:
the device measures ocular saccades.

4. The device of claim 1 wherein:
the device measures pupillometry.

5. The device of claim 1 wherein:
the device measures pursuit tracking during visual pursuit.

6. The device of claim 1 wherein:
the device measures vergence.

7. The device of claim 1 wherein:
the device measures eye closure.

8. The device of claim 1 wherein:
the device measures focused position of the eyes.

9. The device of claim 1 wherein:
the device further measures an ocular parameter selected from the group of dynamic visual acuity and kinetic visual acuity.

10. The device of claim 1 wherein:
the device further measures an ocular parameter selected from the group of virtual retinal stability and retinal image stability.

11. The device of claim 1 wherein:
the device further measures an ocular parameter selected from the group of foveal fixation stability and nystagmus.

12. The device of claim 1 wherein:
the device further comprises a display wherein the display is configured for presenting augmented reality information.

13. The device of claim 1 wherein:
the eye sensor senses eye movement information selected from the group of horizontal eye movement and vertical eye movement.

14. The device of claim 1 wherein:
the head orientation sensor senses pitch of the person's head and yaw of the person's head
the eye sensor senses eye horizontal eye movement and vertical eye movement;
the electronic circuit uses a Fourier transform to generate a vertical gain signal and a vertical phase signal in response to the vertical eye movement information and the pitch information; and
the electronic circuit uses a Fourier transform to generate a horizontal gain signal and a horizontal phase signal in response to the horizontal eye movement information and the yaw information.

15. The device of claim 1 wherein:
the eye sensor further senses the position of at least one eye;
the device further comprises a forward-facing camera; and
the forward-facing camera is responsive to the eye sensor.

16. A human ocular parameter measuring system wherein:
the system is configured for measuring an ocular parameter selected from the group of:
vestibulo-ocular reflex;
ocular saccades;
pupillometry;
pursuit tracking during visual pursuit;
vergence;
eye closure;
focused position of the eyes;
dynamic visual acuity;
kinetic visual acuity;
virtual retinal stability;
retinal image stability;

foveal fixation stability; and
nystagmus; and
the system comprises:
  an eye sensor wherein:
    the eye sensor comprises an image sensor; and
    the eye sensor senses eye movement information selected from the group of:
      horizontal eye movement;
      vertical eye movement;
      pupillometry; and
      eyelid movement;
  a head orientation sensor wherein:
    the head orientation sensor senses a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
  an electronic circuit wherein:
    the electronic circuit comprises a central processing unit, and a memory unit;
    the electronic circuit is responsive to the eye movement information received from the eye sensor; and
    the electronic circuit is responsive to head movement information received from the head orientation sensor; and
  a face shield, wherein:
    the face shield is configured to be worn by a human; and
    the eye sensor, head orientation sensor, and the electronic circuit are attached to the face shield.

17. The system of claim 16 wherein:
the head orientation sensor comprises a head-worn micro-electro-mechanical system integrated circuit comprising a module selected from the group consisting of an accelerometer, a magnetometer, and a gyroscope.

18. The system of claim 16 wherein:
the head orientation sensor comprises a video camera; and
the system further comprises a display wherein the display is configured for presenting augmented reality information.

19. The system of claim 16 wherein:
the electronic circuit is configured for wireless communication in response to the eye movement information and the head movement information.

20. A method for measuring a human ocular parameter comprising the steps of:
  establishing a device that comprises:
    an eye sensor configured for sensing eye movement information selected from the group of:
      horizontal eye movement;
      vertical eye movement;
      pupillometry; and
      eyelid movement;
    a head orientation sensor configured for sensing a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis;
    an electronic circuit; and
    a face shield, wherein:
      the face shield is configured to be worn by a human; and
      the eye sensor, the head orientation sensor, and the electronic circuit are part of the face shield;
  using the electronic circuit to:
    receive eye movement information from the eye sensor;
    receive head movement information from the head orientation sensor; and
    measure an ocular parameter selected from the group of:
      vestibulo-ocular reflex;
      ocular saccades;
      pupillometry;
      pursuit tracking during visual pursuit;
      vergence;
      eye closure;
      focused position of the eyes;
      dynamic visual acuity;
      kinetic visual acuity;
      virtual retinal stability;
      retinal image stability;
      foveal fixation stability; and
      nystagmus.

* * * * *